US012648892B2

(12) United States Patent
Lebrun et al.

(10) Patent No.: US 12,648,892 B2
(45) Date of Patent: Jun. 9, 2026

(54) EMERGENCY EYE WASH

(71) Applicant: Lebrun Labs LLC, Anaheim, CA (US)

(72) Inventors: Stewart Lebrun, Anaheim, CA (US);
Linda Nguyen, Orange, CA (US)

(73) Assignee: Lebrun Labs LLC, Anaheim, CA (US)

( * ) Notice: Subject to any disclaimer, the term of this patent is extended or adjusted under 35 U.S.C. 154(b) by 0 days.

(21) Appl. No.: 18/994,433

(22) PCT Filed: Sep. 24, 2024

(86) PCT No.: PCT/US2024/048093
§ 371 (c)(1),
(2) Date: Jan. 14, 2025

(87) PCT Pub. No.: WO2025/174421
PCT Pub. Date: Aug. 21, 2025

(65) Prior Publication Data
US 2025/0262123 A1 Aug. 21, 2025

Related U.S. Application Data

(60) Provisional application No. 63/553,989, filed on Feb. 15, 2024.

(51) Int. Cl.

| | |
|---|---|
| A61H 35/02 | (2006.01) |
| A61K 9/00 | (2006.01) |
| A61K 9/08 | (2006.01) |
| A61K 31/375 | (2006.01) |
| A61K 47/36 | (2006.01) |
| A61K 47/42 | (2017.01) |

(52) U.S. Cl.
CPC ........... *A61H 35/02* (2013.01); *A61K 9/0048* (2013.01); *A61K 9/08* (2013.01); *A61K 31/375* (2013.01);
(Continued)

(58) Field of Classification Search
CPC .............. A61H 35/02; A61H 2201/105; A61H 2201/1253; A61K 31/375
(Continued)

(56) References Cited

U.S. PATENT DOCUMENTS

| | | | | |
|---|---|---|---|---|
| 7,857,795 B2 * | 12/2010 | Perrin | .................... | A61H 35/02 |
| | | | | 604/294 |
| 2005/0065091 A1 | 3/2005 | Peyman | | |

(Continued)

FOREIGN PATENT DOCUMENTS

| | | |
|---|---|---|
| CN | 116617354 A | 8/2023 |
| WO | 2011088833 A2 | 7/2011 |
| WO | 2023004124 A2 | 1/2023 |

OTHER PUBLICATIONS

International Search Report and Written Opinion dated Jan. 10, 2025, issued in PCT International Appln. No. PCT/US2024/048093.
(Continued)

*Primary Examiner* — David P Angwin
*Assistant Examiner* — William R Klotz
(74) *Attorney, Agent, or Firm* — Amster, Rothstein & Ebenstein LLP

(57) ABSTRACT

Immediate (e.g., within 10 minutes) high volume (e.g., more than 10 mls, 100-1000 mls preferred) washing of the eye for 1-15 minutes or more with a low concentration (e.g., 5-17 mM) of a freshly made ascorbate solution with a pH between 6 and 6.99 after chemical exposure, for example after accidental or malicious splash or spray, results in significantly reduced eye damage. Products, devices and methods are provided.

8 Claims, 27 Drawing Sheets

2A. Duration of Washing - Average TUNEL Positive

(52) U.S. Cl.
CPC .............. *A61K 47/36* (2013.01); *A61K 47/42* (2013.01); *A61H 2201/105* (2013.01); *A61H 2201/1253* (2013.01)

(58) Field of Classification Search
USPC .......................................................... 4/620
See application file for complete search history.

(56) References Cited

U.S. PATENT DOCUMENTS

| | | | | |
|---|---|---|---|---|
| 2008/0141454 | A1* | 6/2008 | Blomet .................. | A61H 35/02 |
| | | | | 4/620 |
| 2009/0288251 | A1* | 11/2009 | Strandberg ............. | A61H 35/02 |
| | | | | 4/620 |
| 2012/0310184 | A1* | 12/2012 | Pedersen ................ | A61H 35/02 |
| | | | | 604/296 |
| 2016/0095794 | A1* | 4/2016 | Eveleigh ................ | A61H 35/02 |
| | | | | 4/620 |
| 2019/0388607 | A1* | 12/2019 | Pontecorvo ......... | A61M 3/0279 |
| 2022/0000838 | A1 | 1/2022 | Lebrun et al. | |

OTHER PUBLICATIONS

Lebrun et al., "An In Vitro Depth of Injury Prediction Model for a Histopathologic Classification of EPA and GHS Eye Irritants," Toxicol. In Vitro, vol. 61, No. 104628, Dec. 19, 2019, 26 pages.

* cited by examiner

1B. Immediate Washing for 15-Minutes

2A. Duration of Washing - Average TUNEL Positive

2B. Duration of Washing – Average Depth of Injury

3B. Time Until Wash: 10-Minutes

4A. Time Until Wash – Average TUNEL Positive

On-Site Eyewash Station

Radians Visionaid Emergency Eyewash Station

Eye Wash Pack

Single Bottle Personal Eyewash

Personal Eyewash Bottle

Portable Eyewash Station

Example of Dosing and eye wash bottle flow or pool seal around an eye socket nozzle, valve, spray, squeeze or handheld inversion nozzle first compartment

EMERGENCY EYE WASH

CROSS-REFERENCE TO RELATED APPLICATIONS

This application is a U.S. national stage entry under 35 U.S.C. § 371 of PCT International Patent Application No. PCT/US2024/048093, filed Sep. 24, 2024, which claims benefit of U.S. Provisional Application No. 63/553,989, filed Feb. 15, 2024, the contents of each of which are hereby incorporated by reference.

STATEMENT OF GOVERNMENT SUPPORT

This invention was made with government support under grant numbers EY033713 and ES031881 awarded by the National Institutes of Health. The government has certain rights in the invention.

BACKGROUND

Chemicals can irritate or damage the eye. Irritation includes transient redness, swelling, and corneal opacity, while eye damage includes scarring, irreversible corneal opacity, and blindness. Previously, we have shown that a depth of injury (DoI) of less than 20% into the stroma of the cornea correlates with chemicals shown to be irritants with effects that reverse in vivo within 21 days, and a DoI of greater than or equal to 20% correlates with chemicals shown to cause eye damage in vivo (Lebrun et al., 2019; UN, 2021).

A high percentage of household cleaning products and industrial chemicals are strong oxidizers (Bello et al., 2009; Čejka and Čejková, 2015; Dumas et al., 2017). When strong oxidizers come into contact with the eye, they can cause damage to the cornea (Shoham et al., 2008; Čejka and Čejková, 2015; Čejková and Čejka, 2015) and even blindness (Kaluzhny et al., 2020). Widely used strong oxidizers include chlorine bleaches ("bleach"), which consist of various forms of hypochlorite including sodium hypochlorite (CASRN 7681-52-9), various stabilizers, and additives including sodium hydroxide (CASRN 1310-73-2) that may impact the concentration of free chlorine (Rutala et al., 1998; Krishnan et al., 2017). Current treatments for the eye after contact with bleach include immediate washing of the eye with lukewarm water for no less than 15 minutes (Ingram, 1990; Racioppi et al., 1994; Chung et al., 2022).

While numerous hazardous chemicals are or can form reactive oxygen species (ROS) and injure the eye (Banin et al., 2003; Corrales et al., 2017; Ung et al., 2017), what may be less widely recognized is that a number of chemicals associated with oxidation and ROS do not injure the eye in vivo (Lebrun et al., 2021a, 2022). During the development of the OptiSafe Eye Irritation Test (OS EIT), an in chemico eye safety test used to classify ocular irritants (Lebrun et al., 2021a, 2023a, 2023b), we found that a high percentage of OS EIT false-positive (FP) results were associated with chemicals identified by database searches as oxidizers that generate ROS (Lebrun et al., 2021a, 2022). Based on this observation, we hypothesized that the addition of tear anti-oxidants to nonanimal eye safety tests might lower the FP rate (Lebrun, 2021, 2022; Lebrun et al., 2021b). To test this hypothesis, tear-related antioxidants were systematically titrated, and their effects on FP chemicals were assessed (Lebrun et al., 2021a). A screen of the five most abundant antioxidants found in human and rabbit tears (Rose et al., 1998; Chen et al., 2009; Choy et al., 2011) was performed.

Antioxidants were added directly to the OS EIT test matrix. The tear antioxidants evaluated included tyrosine, uric acid, ascorbic acid (AA), cysteine, and glutathione (Lebrun et al., 2021a). Based on this evaluation, we found that AA results in a specific reduction of the FP rate (FPR) with no change in the false-negative rate (FNR) (Lebrun et al., 2022, 2023a, 2023b). This effect of ascorbic acid was pronounced at the approximate mean human physiological tear concentration of 0.1 mg/mL (0.01%) (Chen et al., 2009; Lebrun et al., 2021a, 2022), supporting the hypothesis that AA in tears reduces corneal damage by inactivating chemicals that cause ROS generation before they have a chance to damage the eye (Lebrun et al., 2021a, 2022).

We hypothesized that the addition of AA at higher-than-tear concentrations to a washing solution might reduce eye damage caused by strong chemical oxidants. The purpose of the current study is to test the hypothesis that the tear antioxidant AA reduces corneal cell death caused by the strong oxidizer sodium hypochlorite.

As used herein, "toxicity" is used to refer to a substance's ability to damage, irritate, or otherwise negatively affect an eye. Toxicity may be evidenced by pain, irritation, swelling, opaqueness, redness, and discharge. Such effects may be temporary or permanent. Accordingly, the word "toxicity" is defined broadly to include any discomfort or unfavorable experience associated with the presence of a substance contacting an eye.

SUMMARY

A method for reducing extent and depth of keratocyte injury in a stroma of a cornea of a mammal, which cornea has been exposed to a strong oxidizing and/or corrosive chemical, comprising, within 10 minutes or less from exposure, administering to the cornea for a period of 1 minute to 15 minutes a buffered eye wash solution of 0.2% ascorbic acid buffered to a pH of 6.99±0.5 and in an amount of 100 mL to 500 mL as a flow or as a pool in contact with said cornea.

A shelf-stable device or product for effecting the method of claim 1 and producing a buffered eye wash solution of 0.2% ascorbic acid buffered to a pH of 6.99±0.5 and in an amount of 100 mL to 500 mL, the device or product comprising at least a first compartment and a second compartment, wherein the first compartment holds a liquid portion comprising a predefined amount of water or aqueous solution, and wherein the second compartment holds a solid portion comprising an amount of ascorbate powder within a premeasured range; and an activatable mechanism which, when activated, brings the solid portion of the second compartment and the liquid portion of the first compartment into contact, such that the liquid portion mixes, or is capable of being mixed, with the solid portion so as to make 100 mL to 500 mL of a ready-to-use eyewash of 0.2% ascorbic acid solution, wherein the eyewash 0.2% ascorbic acid solution also contains a pH buffer, effecting a pH of 6.99±0.5 in the eyewash 0.2% ascorbic acid solution;

and a nozzle, valve, spray, squeeze or handheld inversion nozzle for delivery to an eye or both eyes of a subject the eyewash 0.2% ascorbic acid solution, wherein the nozzle, valve, spray, squeeze or handheld inversion nozzle allows application of a laminar flow across the eye or both eyes of a user subject when the eye or eyes are positioned within a predetermined range of distance from the nozzle, valve, spray, squeeze or handheld inversion nozzle, so as to wash the eye or eyes or wherein the device comprises an inverted rubber or rubber-like material eye gasket that permits incubation and/or bathing the eye or eyes of the user subject in a pool of the eyewash 0.2% ascorbic acid solution by holding the device or product over the eye or eyes to form a seal around the eye socket with the eye gasket and raising the container up so that the eyewash 0.2% ascorbic acid solution contacts the eye by gravity and stays in contact with a cornea of the eye or eyes, so as to wash the eye or eyes.

A device or product for effecting the method of claim 1 and producing a buffered eye wash solution of 0.1% to 0.3% ascorbic acid buffered to a pH of 6.0 to 6.99±0.5 and in an amount of 100 mL to 1000 mL, the device or product comprising at least a first compartment and a second compartment,
wherein the first compartment holds a liquid portion comprising a predefined amount of water or aqueous solution, and wherein the second compartment holds a solid portion comprising an amount of ascorbate powder within a premeasured range, and
an activatable mechanical mechanism which when activated transfers the solid portion of the second compartment into the liquid portion of the first compartment, such that the liquid portion mixes, or is capable of being mixed, with the solid portion so as to make 100 mL to 1000 mL of a ready-to-use eyewash of 0.1% to 0.3% ascorbic acid solution, and wherein the eyewash 0.2% ascorbic acid solution also contains a pH buffer, effecting a pH of 6.0 to 6.99±0.5 in the eyewash 0.1% to 0.3% ascorbic acid solution;
and a nozzle, valve, spray, squeeze or handheld inversion nozzle for delivery to an eye or both eyes of a subject the eyewash 0.1% to 0.3% ascorbic acid solution.
wherein the nozzle, valve, spray, squeeze or handheld inversion nozzle allows application of a laminar flow across the eye or both eyes of a user subject when the eye or eyes are positioned within a predetermined range of distance from the nozzle, valve, spray, squeeze or handheld inversion nozzle and so as to wash the eye or eyes or wherein the device comprises an inverted rubber or rubber-like material eye gasket that permits incubation and/or bathing the eye or eyes of the user subject in a pool of the eyewash 0.1% to 0.3% ascorbic acid solution by holding the device or product over the eye or eyes to form a seal around the eye socket with the eye gasket and raising the container up so that the eyewash 0.1% to 0.3% ascorbic acid solution contacts the eye by gravity and stays in contact with a cornea of the eye or eyes.

A device or product for reducing eye damage after chemical exposure "emergency eye wash", comprised of a container that has a single compartment that holds a solid portion, and water can be quickly added to the container, and mixed by shaking, inversion transfers or a rotary or other mixing apparatus has been preinstalled, and the solid and liquid can be mixed quickly and then the container facilitates eye washing either by having sufficient volume and capability to deliver lateral flow washing across the eye or holding over the eye for a period of 1-15 minutes and the solid portion contains a contains a powder form of a pH buffer and premeasured ascorbate powder and, whereupon mixing the solid goes into solution to form a ready to use eye wash and a pH between 6-6.99 is achieved prior to washing or incubating the eye, as disclosed by the specification figures of bottles and containers.

A device or product or container that allows immediate (within 10 minutes) high volume (more than 10 mls, 100-1000 mls preferred) washing of the eye for 1-15 minutes with a low concentration (5-17 mM) of a freshly made ascorbate solution with a pH between 6 and 6.99 for use after chemical exposure, for example after accidental or malicious splash or spray, results in significantly reduced eye damage.

A product or device to make readily available ascorbic acid wash and procedure, which will overcome the inherent decay and loss of activity with time of ascorbic acid in solution, by keeping ascorbate as a powder that will quickly dissolve an form a wash solution, and the product or device ingredients including buffers prevent the inherent toxicity of ascorbate due to very high acidity by buffering the pH from a toxic acid range that can cause acid burn to the cornea, to a pH range that is nontoxic, for example pH 6-8.

A method of treating or reducing damage to an eye of a subject user comprising activating the eye wash solution of any of the devices or products of the present invention and irrigating and/or bathing the eye with said eye wash solution so as to thereby treat or reduce damage to the eye of a subject user.

A method for treating a cornea of a mammal, which cornea has been exposed to an strong oxidizing and/or corrosive chemical, comprising, administering to the eye a buffered eye wash solution of 0.1-0.3% ascorbic acid buffered to a pH of 6.0 to 6.99±0.5.

BRIEF DESCRIPTION OF THE DRAWINGS

FIG. 1A depicts the immediate washing for 1-minute. FIG. 1B depicts the immediate washing for 15-minutes. FIG. 1C depicts the immediate washing for 30-minutes. FIG. 1D depicts the immediate washing for 60-minutes.

FIG. 2A depicts the average TUNEL positive nuclei (dead cells). FIG. 2B depicts the average depth of injury (dead regions).

FIG. 3A depicts the results of immediate washing after exposure to sodium hypochlorite. FIG. 3B depicts the results of waiting 10-minutes to wash after exposure to sodium hypochlorite. FIG. 3C depicts the results of waiting 120-minutes to wash after exposure to sodium hypochlorite.

FIG. 4A depicts the average TUNEL positive nuclei (dead cells). FIG. 4B depicts the average depth of injury (dead regions).

FIG. 5A shows example images and FIG. 5B shows quantification with results are for the average of three eyes, three sections per eye. Error bars are the SE. Quantification of all sections is shown in Table 3.

FIG. 5A, Eye 3 Section C has poor staining and this section was not used for data analysis. Eye 1, 2 or 3=The number assigned to each repeat; Section A, B or C=the 3 sections stained for each eye; NaOCl=Sodium Hypochlorite.

DETAILED DESCRIPTION

Figure 1A:
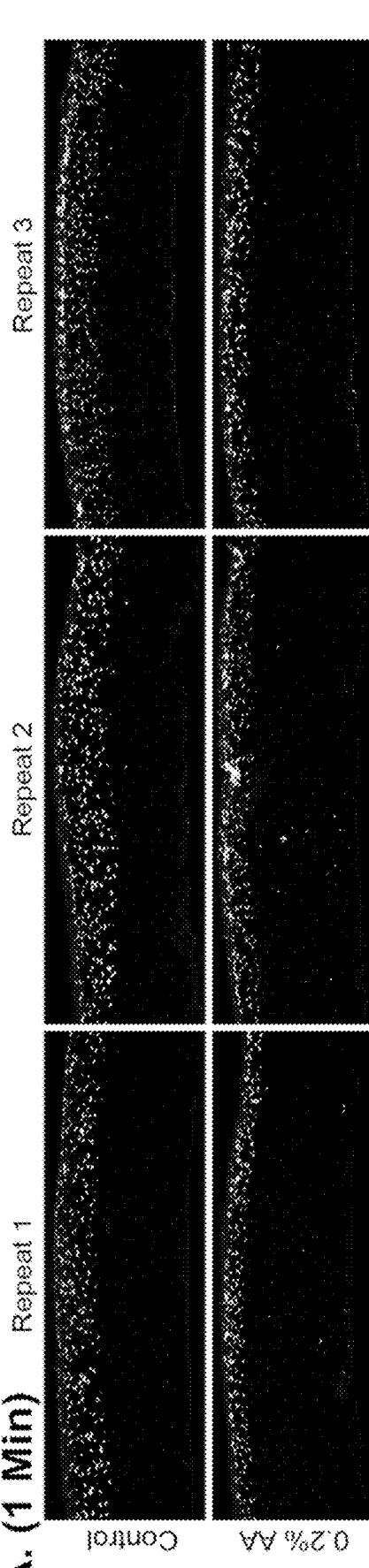
FIGS. 1A-1D: depicts results for different washing durations with a control and 0.2% Ascorbic acid after the eye was exposed to sodium hypochlorite. White=dead cells of the cornea. Blue=live cells of the cornea.

A method for reducing extent and depth of keratocyte injury in a stroma of a cornea of a mammal, which cornea has been exposed to a strong oxidizing and/or corrosive chemical, comprising, within 10 minutes or less from exposure, administering to the cornea for a period of 1 minute to 15 minutes a buffered eye wash solution of 0.2% ascorbic acid buffered to a pH of 6.99±0.5 and in an amount of 100 mL to 500 mL as a flow or as a pool in contact with said cornea.

In embodiments, a line of demarcation of keratocyte damage in the cornea is less deep after being administered the buffered eye wash solution than if administered an otherwise identical buffered eye wash solution containing 10% ascorbic acid or 0% ascorbic acid.

In embodiments, the method results in a depth of damage in the stroma of the cornea of less than 20%.

In embodiments, a line of demarcation of keratocyte cell death in the cornea is less deep after being administered the buffered eye wash solution than if administered water only.

A shelf-stable device or product for effecting the method of claim 1 and producing a buffered eye wash solution of 0.2% ascorbic acid buffered to a pH of 6.99±0.5 and in an amount of 100 mL to 500 mL, the device or product comprising at least a first compartment and a second compartment, wherein the first compartment holds a liquid portion comprising a predefined amount of water or aqueous solution, and wherein the second compartment holds a solid portion comprising an amount of ascorbate powder within a premeasured range; and an activatable mechanism which, when activated, brings the solid portion of the second compartment and the liquid portion of the first compartment into contact, such that the liquid portion mixes, or is capable of being mixed, with the solid portion so as to make 100 mL to 500 mL of a ready-to-use eyewash of 0.2% ascorbic acid solution, wherein the eyewash 0.2% ascorbic acid solution also contains a pH buffer, effecting a pH of 6.99±0.5 in the eyewash 0.2% ascorbic acid solution;

and a nozzle, valve, spray, squeeze or handheld inversion nozzle for delivery to an eye or both eyes of a subject the eyewash 0.2% ascorbic acid solution, wherein the nozzle, valve, spray, squeeze or handheld inversion nozzle allows application of a laminar flow across the eye or both eyes of a user subject when the eye or eyes are positioned within a predetermined range of distance from the nozzle, valve, spray, squeeze or handheld inversion nozzle, so as to wash the eye or eyes or wherein the device comprises an inverted rubber or rubber-like material eye gasket that permits incubation and/or bathing the eye or eyes of the user subject in a pool of the eyewash 0.2% ascorbic acid solution by holding the device or product over the eye or eyes to form a seal around the eye socket with the eye gasket and raising the container up so that the eyewash 0.2% ascorbic acid solution contacts the eye by gravity and stays in contact with a cornea of the eye or eyes, so as to wash the eye or eyes.

In embodiments, the activatable mechanical comprises a mechanical mechanism.

In embodiments, the activatable mechanical mechanism comprises a lever or twist action mechanism which brings the contents of the first and second compartment into contact.

In embodiments, the liquid portion mixes with the solid portion by shaking, inverting the device or product or portion thereof, or by an automatic device with a rotating blade within the container that initiates upon use, or an automatic device for mixing via a stir bar, shaking, vibration, vortex, or rotary paddle.

A device or product for effecting the method of claim 1 and producing a buffered eye wash solution of 0.1% to 0.3% ascorbic acid buffered to a pH of 6.0 to 6.99±0.5 and in an amount of 100 mL to 1000 mL, the device or product comprising at least a first compartment and a second compartment, wherein the first compartment holds a liquid portion comprising a predefined amount of water or aqueous solution, and wherein the second compartment holds a solid portion comprising an amount of ascorbate powder within a premeasured range, and an activatable mechanical mechanism which when activated transfers the solid portion of the second compartment into the liquid portion of the first compartment, such that the liquid portion mixes, or is capable of being mixed, with the solid portion so as to make 100 mL to 1000 mL of a ready-to-use eyewash of 0.1% to 0.3% ascorbic acid solution, and wherein the eyewash 0.2% ascorbic acid solution also contains a pH buffer, effecting a pH of 6.0 to 6.99±0.5 in the eyewash 0.1% to 0.3% ascorbic acid solution;

and a nozzle, valve, spray, squeeze or handheld inversion nozzle for delivery to an eye or both eyes of a subject the eyewash 0.1% to 0.3% ascorbic acid solution.

wherein the nozzle, valve, spray, squeeze or handheld inversion nozzle allows application of a laminar flow across the eye or both eyes of a user subject when the eye or eyes are positioned within a predetermined range of distance from the nozzle, valve, spray, squeeze or handheld inversion nozzle and so as to wash the eye or eyes or wherein the device comprises an inverted rubber or rubber-like material eye gasket that permits incubation and/or bathing the eye or eyes of the user subject in a pool of the eyewash 0.1% to 0.3% ascorbic acid solution by holding the device or product over the eye or eyes to form a seal around the eye socket with the eye gasket and raising the container up so that the eyewash 0.1% to 0.3% ascorbic acid solution contacts the eye by gravity and stays in contact with a cornea of the eye or eyes.

In embodiments, the solid portion is 5.7 mM-17 mg/ml ascorbic acid.

In embodiments, the solid portion is about 11.4 mM ascorbic acid.

In embodiments, the buffering capacity of the liquid, is such that the mixture pH achieved is between 6 and 6.99.

In embodiments, the liquid portion is stored in a bottle that allows for rapid mixing and eye irrigation or washing, for example any one of the bottle types shown in FIGS. 5-9.

In embodiments, the device or product has a shelf life of at least 6 months, optionally verified by 1) lack of a precipitate or discoloration and/or 2) chemical analytical technique demonstrating at least 80% of the ascorbic acid is in the biologically active "reduced" form, or 3) a functional test at 6 months or longer that demonstrates the product reduces corneal keratocyte death after a toxic chemical exposure to the eyes.

In embodiments, eye damage caused by a ocular corrosive chemicals is reduced by 50% or more after using the eye wash of the device or product on the eye.

In embodiments, the pH buffering system is comprised of one of the following: sodium acetate (CASRN: 127-09-3), acetic acid (CASRN: 64-19-7), ammonium acetate (CASRN: 631-61-8), ammonium bicarbonate (CASRN: 1066-33-7), ammonium sulfate (CASRN: 7783-20-2), bicine (CASRN: 150-25-4), ACES (CASRN: 7365-82-4), ADA (CASRN: 26239-55-4), Bis-tris (CASRN: 6976-37-0), Boric acid (CASRN: 10043-35-3), sodium tetraborate (CASRN: 1330-43-4), sodium bicarbonate (CASRN: 144-55-8), sodium carbonate (CASRN: 497-19-8), sodium citrate dihydrate (CASRN: 6132-04-3), citric acid (CASRN: 77-92-9), diethanolamine (CASRN: 111-42-2), magnesium chloride hexahydrate (CASRN: 7791-18-6), sodium phosphate dibasic dihydrate (CASRN: 10028-24-7), glycine (CASRN: 56-40-6), hydrochloric acid (CASRN: 7647-01-0), sodium hydroxide (CASRN: 1310-73-2), imidazole (CASRN: 288-32-4), sodium phosphate dibasic heptahydrate (CASRN: 7782-85-6), sodium phosphate monobasic monohydrate (CASRN: 10049-21-5), potassium phosphate monobasic (CASRN: 7778-77-0), potassium phosphate dibasic (CASRN: 7758-11-4), sodium acetate (CASRN: 127-09-3), Tris base (CASRN: 77-86-1), or similar.

In embodiments, the liquid portion includes one or more of the following: salts, which may be any one of the following: sodium chloride (CASRN: 7647-14-5), potassium chloride (CASRN: 7447-40-7), calcium chloride (CASRN: 10043-52-4), sodium nitrate (CASRN: 7631-99-4), potassium sulfate (CASRN: 7778-80-5), potassium chlorate (CASRN: 3811-04-9), calcium phosphate (CASRN: 7758-87-4), potassium perchlorate (CASRN: 7778-74-7), sodium carbonate (CASRN: 497-19-8), sodium hydrogen sulfate (CASRN: 7681-38-1), sodium phosphate monobasic (CASRN: 7558-80-7), disodium hydrogen phosphate (CASRN: 7558-79-4), potassium bisulfate (CASRN: 7646-93-7), ammonium sulfate (CASRN: 7783-20-2), potassium cyanide (CASRN: 151-50-8), ammonium iron (II) sulfate hexahydrate (CASRN: 7783-85-9), magnesium sulfate (CASRN: 7487-88-9), calcium sulfate (CASRN: 7778-18-9), lithium hydroxide (CASRN: 1310-65-2), lithium fluoride (CASRN: 7789-24-4) or similar.

In embodiments, the solid portion is composed of powdered or dry solid, formulated such that it rapidly dissolves within part 1 upon shaking, and wherein the solid may consist of any of the following ascorbic acids, ascorbates or similar: sodium ascorbate (CASRN: 134-03-2), calcium ascorbate (CASRN: 5743-28-2) ascorbic acid, (CASRN: 50-81-7), potassium ascorbate (CASRN: 15421-15-5), magnesium L-ascorbate (CASRN: 15431-40-0), dehydro-L-(+)-ascorbic acid dimer (CASRN: 72691-25-9), ascorbic acid 6-palmitate (CASRN: 137-66-6), 5,6-Isopropylidene-L-ascorbic acid (CASRN: 15042-01-0), 2-Phospho-L-ascorbic acid trisodium salt (CASRN: 66170-10-3), 2-O-a-D-Glu-copyranosyl-L-ascorbic acid (CASRN: 129499-78-1), 5,6-O-benzylidene-2,3-dideoxy-L-ascorbic acid (CASRN: 1217498-73-1), oxalic acid (CASRN: 144-62-7), ascorbic stearate (CASRN: 10605-09-1), erythorbic acid (CASRN: 89-65-6), glyceryl ascorbate (CASRN: 1120360-13-5), 3-O-Ethyl-L-ascorbic acid (CASRN: 86404-04-8), L-ascorbic acid 2-phosphate sesquimagnesium salt hydrate (CASRN: 1713265-25-8), (L)-Dehydroascorbic acid (CASRN: 490-83-5), 2,6-Dichlorophenol-indophenol sodium salt dihy-drate (CASRN: 620-45-1), L-ascorbyl 2,6-Dibutyrate (CASRN: 4337-04-6), L-ascorbic acid-2-13C (CASRN: 178101-89-8) or similar.

A device or product for reducing eye damage after chemi-cal exposure "emergency eye wash", comprised of a container that has a single compartment that holds a solid portion, and water can be quickly added to the container, and mixed by shaking, inversion transfers or a rotary or other mixing apparatus has been prein-stalled, and the solid and liquid can be mixed quickly and then the container facilitates eye washing either by having sufficient volume and capability to deliver lat-eral flow washing across the eye or holding over the eye for a period of 1-15 minutes and the solid portion contains a contains a powder form of a pH buffer and premeasured ascorbate powder and, whereupon mixing the solid goes into solution to form a ready to use eye wash and a pH between 6-6.99 is achieved prior to washing or incubating the eye, as disclosed by the specification figures of bottles and containers.

In embodiments, the chemical damage to the stroma of the cornea is reduced, but damage to the epithelium of the cornea is not reduced.

In embodiments, the device or product when used cor-rectly chemical damage to the stroma is reduced from greater than 20% to less than 20%.

In embodiments, the chemical damage to the stroma is reduced from an injury associated with eye damage to an injury associated with eye irritation.

In embodiments, the device or product when used the number of dead corneal keratocytes is reduced after chemi-cal damage to the cornea, compared to not using the product.

In embodiments, the device or product when used, chemi-cal damage to the cornea is reduced.

In embodiments, the device or product when used, dam-age to the corneal stroma is reduced from 30% or greater after chemical exposure to 10% or less after washing with the eye wash device.

In embodiments, the device or product includes enough solution to allow for continuous washing for at least 1 minute and up to 15 minutes.

A device or product or container that allows immediate (within 10 minutes) high volume (more than 10 mls, 100-1000 mls preferred) washing of the eye for 1-15 minutes with a low concentration (5-17 mM) of a freshly made ascorbate solution with a pH between 6 and 6.99 for use after chemical exposure, for example after accidental or mali-cious splash or spray, results in significantly reduced eye damage.

A product or device to make readily available ascorbic acid wash and procedure, which will overcome the inherent decay and loss of activity with time of ascorbic acid in solution, by keeping ascorbate as a powder that will quickly dissolve an form a wash solution, and the product or device ingredients including buffers prevent the inherent toxicity of ascorbate due to very high acidity by buffering the pH from a toxic acid range that can cause acid burn to the cornea, to a pH range that is nontoxic, for example pH 6-8.

In embodiments, the device or product is supplied as a ready to use packet, to use in a do it yourself container to reduce or reverse eye damage by the therapeutic application after an accidental or malicious splash or spray of a toxin to the eye, where the formulation is reconstituted and the eye is irrigated after exposure to an ocular toxin.

In embodiments, the device or product is intended to be used within 10 minutes after an eye to prevent blindness or severe eye damage caused by chemical weapons.

In embodiments, the device or product is intended to be used within 10 minutes after an eye to prevent blindness or severe eye damage caused by industrial chemicals.

In embodiments, the device or product is intended to be used within 10 minutes after an eye to prevent blindness or severe eye damage caused by laboratory chemicals.

In embodiments, the device or product is intended to be used within 10 minutes after an eye to prevent blindness or severe eye damage caused by household chemicals.

A method of treating or reducing damage to an eye of a subject user comprising activating the eye wash solution of any of the devices or products of the present invention and irrigating and/or bathing the eye with said eye wash solution so as to thereby treat or reduce damage to the eye of a subject user.

In embodiments, the eye has been contacted with a corrosive substance.

A method for treating a cornea of a mammal, which cornea has been exposed to an strong oxidizing and/or corrosive chemical, comprising, administering to the eye a buffered eye wash solution of 0.1-0.3% ascorbic acid buff-ered to a pH of 6.0 to 6.99±0.5.

In embodiments, the buffered eye wash solution is admin-istered in an amount of 100 mL to 1000 mL.

In embodiments, the buffered eye wash solution amount is administered to the eye within a period of 1 minute to 15 minutes.

In embodiments, the buffered eye wash solution is admin-istered as a flow or as a pool in contact with said cornea.

In embodiments, the buffered eye wash solution is admin-istered within 10 minutes or less from exposure to the oxidizing and/or corrosive chemical.

In embodiments, a line of demarcation of keratocyte damage in the cornea is less deep after being administered the buffered eye wash solution than if administered an otherwise identical buffered eye wash solution containing 10% ascorbic acid or 0% ascorbic acid.

In embodiments, the method results in a depth of damage in the stroma of the cornea of less than 20%.

In embodiments, a line of demarcation of keratocyte damage in the cornea is less deep after being administered the buffered eye wash solution than if administered water only.

Section #1

As disclosed herein, the inventors have discovered that immediate high volume washing of the eye with a low concentration (5-17 mM) of a freshly made ascorbate solu-tion with a pH between 6 and 6.99 protects the eye from chemical damage.

The Unique Redox Environment of the Eye

The majority of the cornea consists of a stroma, which is comprised of a unique transparent collagen organized as lamella and maintained by highly specialized corneal resi-dent fibroblast cells named the corneal keratocytes. The stroma is protected by a 5-7-layer thick corneal epithelium. This epithelium is stratified, nonkeratinized squamous tissue. The conjunctiva is composed of 3-5 cell layers of stratified, nonkeratinized cells. The cornea and conjunctiva function as barriers to protect the eye from exposure to environmental insults including foreign bodies, microbes, and irritating chemicals.

Tear film consists of three layers—mucin, aqueous, and lipid (inner to outer) that contribute to the health and maintenance of the ocular surface (Conrady et al., 2016). Lacrimal glands produce the aqueous layer of the tear film, which is produced at a basal rate of up to 2 microliter per minute (Kim et al., 2019) and up to 100-fold higher in response to mechanical, thermal, or chemical exposure (reflex rate). These increased aqueous tears dilute, clear, and detoxify chemicals.

The human eye contains the mucosal surface of body that is most exposed to the surrounding environment, including atmospheric oxygen, toxic chemicals, and radiation/ROS produced in situ from light-induced oxidative damage. A significant effect on ocular surface inflammation, corneal epithelium lesions, and ocular discomfort is related to dry eye and increased tear film osmolarity. The tear film has significant levels of antioxidants.

In particular, the cornea can be exposed to reactive oxygen species (ROS) that include superoxide anion ($O_2^-$), hydrogen peroxide ($H_2O_2$), hydroxyl radical (HO*), hydroperoxides (ROOH), peroxyl radicals (ROO*), and singlet oxygen ($O_2$) (Nita and Grzybowski, 2016; Ung et al., 2017). ROS can be the direct product of toxic chemicals or generated by cells during bursts of metabolism. Cellular phospholipid bilayers are susceptible to ROS-induced damage via lipid peroxidation, which occurs when free radical species including oxyl radicals, peroxyl radicals, and hydroxyl radicals remove electrons from lipids and subsequently produce reactive intermediates that can cause massive damage via redox cycling (Njie-Mbye et al., 2013; Babizhayev, 2016; Tangvarasittichai, 2018; Su et al., 2019). The oxidation of nucleotides and proteins may lead to changes in gene expression, mutations, and the formation of insoluble protein aggregates.

The eye is protected against oxidative stress by antioxidants in the cornea, aqueous humor, and tear film. As shown in Table 1, human tear film and aqueous humor have a similar concentration of antioxidants. Tear film is the first biological fluid to interact with and potentially detoxify chemicals that contact the eye. Nonetheless, nonanimal tests do not model tears or the tearing process. Likewise, the aqueous humor is continuously generated and drained and has a composition similar to tear film (Chen, et al; 2009). Aqueous humor production and turnover is a dynamic process, which like tearing, is not modeled by nonanimal tests. In human tears, ascorbic acid and uric acid account for approximately 50% of the total antioxidant activity, with ascorbic acid being the most abundant. Other small molecules, including reduced glutathione, L-cysteine, and L-tyrosine, make up the rest. Enzymes of the aqueous humor include superoxide dismutase (SOD), which has an activity around 3.5 U/mL (Behndig et al., 1998). In the order of abundance in human aqueous humor, nonenzymatic antioxidants include ascorbic acid (530 µM), L-tyrosine (78 µM), uric acid (43 µM), L-cysteine (14.3 µM), and glutathione (5.5 µM). SOD activity is not believed to contribute significantly to the antioxidant defense mechanisms of the aqueous humor (Chen et al., 2009).

Table 1. Antioxidants Present in Aqueous Humor and Tear

| Antioxidant | Aqueous Humor[a] | Tear Film[a] |
|---|---|---|
| L-Tyrosine | 78 µM | 45 µM |
| Uric acid | 43 µM | 328 µM |
| Ascorbic acid | 530 µM | 665 µM |
| L-Cysteine | 14.3 µM | 48 µM |
| Glutathione | 5.5 µM | 107 µM |
| Superoxide dismutase | ~5.1 U/mL[b] | 3.5 U/mL[b] |

[a] Chen et al., 2009
[b] Behndig et al., 1998

Even though scientists in the area of ophthalmology have characterized the importance of protective antioxidant effects on the eye in disease, current procedures after chemical splash into the eye only involve washing the eye with water or, as discussed below, in a few laboratory studies the application of a few drops (~40-80 µL) of 10% AA solution starting 2 hours after chemical injury.

In the 1970s, Pfister et al. identified a reduction in aqueous humor AA concentrations following severe alkali burns in rabbits (35-second eye exposure to 1 N NaOH). They hypothesized that restoring aqueous humor levels of AA would reduce this damage. They compared the subcutaneous injection of a 15% AA solution (within 3 h of the burn) once daily compared with a topical 10% AA eye drop (hydroxyethylcellulose with polyvinylpyrrolidone, thimerosal, and EDTA) adjusted to pH 7.2 administered 2 h after the burn and at hourly intervals for 14 h per day. They found that the eye drops reduced corneal ulceration but subcutaneous injections were not effective (Levinson et al., 1976; Pfister and Paterson, 1977; Pfister et al., 1978, 1980). Pfister et al. propose that the observed AA-related reduction in corneal ulceration was based on its involvement in proline and lysine hydroxylation and fibroblast collagen extrusion (Levinson et al., 1976, Lee and Chung, 2012). However, in some studies, AA did not seem to have much effect on epithelial migration/wound closure (Levinson et al., 1976). It has been proposed that AA may suppress fibroblast growth factor and matrix metalloproteinase-9 (Lee and Chung, 2012).

A topical eye drop (TED) formulation of four FDA-approved drugs including AA [25 µM suberoylanilide hydroxamic acid (vorinstat), 25 µM enalapril, 0.5% ketorolac, and 10% vitamin C] has been tested on rabbit eyes after exposure to the alkylating agent, sulfur mustard (SM). In this study, two drops of the TED solution were applied to the eye, two times a day, starting 2 hours after SM exposure (Tripathi et al., 2020). The authors concluded that TED treatment after SM exposure improves clinical symptoms by reducing corneal edema, central corneal thickness, corneal haze, and inflammatory and profibrotic marker levels, such as those of transforming growth factor (TGF)-β1 and cyclooxygenase-2 (Tripathi et al., 2020).

In another study, eye drops formulated with 10% AA combined with TRAM-34, a selective inhibitor of intermediate-conductance calmodulin/calcium-activated K+ channels, was shown to reduce markers of corneal fibrosis/haze and downregulation of various fibrotic markers associated with TGF-β-mediated fibrosis was observed (Fuchs et al., 2022; Mohan et al., 2022).

As discussed above, past studies on the therapeutic effects of AA after chemical injury evaluated 10% AA eye drop solutions (alone and in combination with drugs). For eye-drop studies, typically several drops are applied 2 hours after injury and regularly thereafter (Tripathi et al., 2020; Fuchs et al., 2022; Mohan et al., 2022).

Ascorbic acid and ascorbate are water-soluble essential nutrient and is more highly concentrated in the tear film than in the serum. Its main functions are as an electron donor/antioxidant and cofactor for certain dioxygenases in epigenetic regulation (Han et al., 2021). Other roles in the human body include cell-signaling, as a hormone growth factor, and cytokine, including possibly via sodium-dependent vitamin C transporter 2 (SVCT) mediation of Janus kinase 2 (JAK), which s promotes regulation of vitamin C in epigenetic modifications, and complex effects related to the regulation of cell pluripotency and differentiation (Han et al., 2021). Other functions include immune system modulation (Carr and Maggini, 2017).

Ascorbic acid induces collagen secretion and formation of cell sheets in the eye (human corneal cell culture; Grobe and Reichl, 2013). Ascorbic acid is a required cofactor for the hydroxylation of the amino acids proline and lysine required for collagen triple helix formation and stabilization, including in tissue repair (Levene and Bates, 1975; Grobe and Reichl, 2013; Peterkofsky, 1972). Collagen is critical to maintaining eye health and function; including the stroma (collagen I) and the basement membrane (collagen IV).

Because cell and excised eye assays could respond to ascorbic acid by altering cell growth, repair or other metabolic responses or possibly as a "nutritional response" (impacting the collagens etc.), as discussed above, it has been unclear (variables left undefined) if the ascorbic acid in tear, or added ascorbic acid, specifically inactivates reactive molecules and this prevents damage from occurring in the first place (versus the other types of responses mentioned above). However, in our experiments, a cell free macromolecular test system that we used to specifically measures the level of molecular damage. By using a cell free test system, one can rule out effects on cell growth and repair, nutrition and possibly other complex yet to be defined variables related to cells and tissues; and more specifically determine if the mechanism of action is specific to the inactivation of ROS by direct chemical reduction (provides an electron to stabilize ROS). Therefore, the antioxidant provides immediate protection against ROS and other toxins. The response of a complex biological system is not required. However, because antioxidants such as ascorbic acid can buffer to extreme pH, and extreme pH in itself is damaging to the eye, these must be highly buffered (to between pH 6.5-7.5) before coming into contact with the eye. In our experience, HEPES, Tris and bicarbonate (for $CO_2$ systems) are all effective buffers.

We found that washing the eye with 100-500 ml of a buffered 0.2% AA within 10 minutes of chemical exposure to the eye is particularly effective at reducing cell death after an accidental spill or other eye exposure to strong g corrosives or oxidizers.

Ascorbic Acid (AA) and Ascorbate

Ascorbic acid and ascorbate are commonly used interchangeably to describe any one of the mineral salts of ascorbic acid. To those familiar with the state of the art, mineral salts of ascorbic acid are commonly used interchangeably because positively charged counter ions of salt often dissociate in solution and the biologically active ascorbic acid is the same in solution—regardless of the counter ion that forms the dry salt. In embodiments, the purpose of this invention is served by all salts of ascorbic acid because they have the same intended biological function of stopping damage to the cornea by donating an electron and functioning as an antioxidant. This reduces chemical oxidation and ROS damage of biologically important molecules critical for cell viability (important molecules for viability include membranes, proteins and nucleotides). This activity includes all of the ascorbic acids, ascorbates or similar: sodium ascorbate (CASRN: 134-03-2), calcium ascorbate (CASRN: 5743-28-2), ascorbic acid, (CASRN: 50-81-7), potassium ascorbate (CASRN: 15421-15-5), magnesium L-ascorbate (CASRN: 15431-40-0), dehydro-L-(+)-ascorbic acid dimer (CASRN: 72691-25-9), ascorbic acid 6-palmitate (CASRN: 137-66-6), 5,6-Isopropylidene-L-ascorbic acid (CASRN: 15042-01-0), 2-Phospho-L-ascorbic acid trisodium salt (CASRN: 66170-10-3), 2-O-a-D-Glucopyranosyl-L-ascorbic acid (CASRN: 129499-78-1), 5,6-O-benzylidene-2,3-dideoxy-L-ascorbic acid (CASRN: 1217498-73-1), oxalic acid (CASRN: 144-62-7), ascorbic stearate (CASRN: 10605-09-1), erythorbic acid (CASRN: 89-65-6), glyceryl ascorbate (CASRN: 1120360-13-5), 3-O-Ethyl-L-ascorbic acid (CASRN: 86404-04-8), L-ascorbic acid 2-phosphate sesquimagnesium salt hydrate (CASRN: 1713265-25-8), (L)-Dehydroascorbic acid (CASRN: 490-83-5), 2,6-Dichlorophenol-indophenol sodium salt dihydrate (CASRN: 620-45-1), L-ascorbyl 2,6-Dibutyrate (CASRN: 4337-04-6), L-ascorbic acid-2-13C (CASRN: 178101-89-8) or similar.

Antioxidant Formulations

Because metals may promote oxidation and/or generation of reactive oxygen species, the antioxidant formulation should have no metals in any valance state, including metal complexes (such as zinc ascorbate complexes). Accordingly, preferred embodiments of the formulation do not comprise any metals, including in particular, iron, silver, magnesium, zinc, and copper. Antioxidants, such as ascorbate, serve the purpose of reducing oxidative injury within biological systems through quenching of free radicals (Gulcin, 2020). In contrast, metals cause reduction-oxidation cycling reactions which causes damaged. Through the Fenton reaction, metals, such as iron, promote oxidation and the production of free radicals; ultimately, this results in biological injury (Winterbourn, 1995). Specifically, the Fenton reaction produces hydroxyl radicals from hydrogen peroxide and an Iron (II) catalyst. While the inclusion of antioxidants is aimed to target this oxidative stress, there is a point in which the "increased formation of reactive oxygen species (ROS) overwhelms body antioxidant protection and subsequently induces DNA damage" (Jomova and Valko, 2011). These metals include iron (Fe), copper (Cu), chromium (Cr), cobalt (Co) and other metals (Jomova and Valko, 2011). Furthermore, the addition of metals is counterproductive to the initial objective. The point of interest is oxidative stress mediation; the disclosed embodiments do not align with the addition of metals, and indeed, we teach away from this.

As electron donors, ascorbic acid and the ascorbates are highly unstable in solution. In solution ascorbates have shelf life of hours to days. Such a short shelf life would not be useful for an emergency eye wash product, which needs to sit for months or years until there is an emergency and in this case still have sufficient activity to be of use.

The antioxidant formulation is dissolved in a salt buffer system, adjusted to a neutral pH, preferably between about pH 6 and pH 7.5. The buffer may be any buffer used in the art, such as HEPES, Tris or bicarbonate buffer, all of which work well in this pH range. Sodium chloride should be added to provide osmolarity mirroring that of physiologic tears, typically normal saline; 6 mg/ml NaCl was used in these studies.

Other ingredients, might include thickening agents, such as carboxymethyl cellulose, moisturizer/humectant/emollient, such as glycerin, and preservatives (although antioxidants are also useful as preservatives against oxidative damage), such as benzoic acid, benzyl alcohol, benzalkonium chloride, etc., may also be added, particularly if an antioxidant formulation is formulated for sale and storage at room temperature.

EXPERIMENTAL DETAILS AND EXAMPLES

Sodium Hypochlorite Exposure and Rinsing

Immediately prior to each experiment (<1 hour), sodium hypochlorite (CASRN 7681-52-9, Sigma-Aldrich, St. Louis, USA) was freshly diluted in sterile deionized (DI) water, mixed by five tube inversions prior to each application, and applied directly to the eyes (corneas) by transferring 100 μL with a micropipette into the dosing ring; the corneas were then exposed to this solution for exactly 1 minute. Immediately after exposure, corneas were rinsed by forcefully dispensing 20 mL of either saline (0.9 g/L NaCl) or a wash solution (as described below) from a syringe fitted with an 18-gauge, blunt-tip needle.

Washing

After sodium hypochlorite exposure, eyes were washed with 100 mL of wash solution for a defined duration using a device filled with a buffered ascorbic acid solution similar to devices shown in FIG. 5-9, as described:

Since ascorbate is unstable in solution but very stable as a dry powder, 2 part wash solutions were developed:

Part 1 (to a Predissolved Liquid):

a. a pH buffering system, which may be any of the following: sodium acetate (CASRN: 127-09-3), acetic acid (CASRN: 64-19-7), ammonium acetate (CASRN: 631-61-8), ammonium bicarbonate (CASRN: 1066-33-7), ammonium sulfate (CASRN: 7783-20-2), bicine (CASRN: 150-25-4), ACES (CASRN: 7365-82-4), ADA (CASRN: 26239-55-4), Bis-tris (CASRN: 6976-37-0), Boric acid (CASRN: 10043-35-3), sodium tetraborate (CASRN: 1330-43-4), sodium bicarbonate (CASRN: 144-55-8), sodium carbonate (CASRN: 497-19-8), sodium citrate dihydrate (CASRN: 6132-04-3), citric acid (CASRN: 77-92-9), diethanolamine (CASRN: 111-42-2), magnesium chloride hexahydrate (CASRN: 7791-18-6), sodium phosphate dibasic dihydrate (CASRN: 10028-24-7), glycine (CASRN: 56-40-6), hydrochloric acid (CASRN: 7647-01-0), sodium hydroxide (CASRN: 1310-73-2), imidazole (CASRN: 288-32-4), sodium phosphate dibasic heptahydrate (CASRN: 7782-85-6), sodium phosphate monobasic monohydrate (CASRN: 10049-21-5), potassium phosphate monobasic (CASRN: 7778-77-0), potassium phosphate dibasic (CASRN: 7758-11-4), sodium acetate (CASRN: 127-09-3), Tris base (CASRN: 77-86-1), or similar.

b. salts, which may be any one of the following: sodium chloride (CASRN: 7647-14-5), potassium chloride (CASRN: 7447-40-7), calcium chloride (CASRN: 10043-52-4), sodium nitrate (CASRN: 7631-99-4), potassium sulfate (CASRN: 7778-80-5), potassium chlorate (CASRN: 3811-04-9), calcium phosphate (CASRN: 7758-87-4), potassium perchlorate (CASRN: 7778-74-7), sodium carbonate (CASRN: 497-19-8), sodium hydrogen sulfate (CASRN: 7681-38-1), sodium phosphate monobasic (CASRN: 7558-80-7), disodium hydrogen phosphate (CASRN: 7558-79-4), potassium bisulfate (CASRN: 7646-93-7), ammonium sulfate (CASRN: 7783-20-2), potassium cyanide (CASRN: 151-50-8), ammonium iron (II) sulfate hexahydrate (CASRN: 7783-85-9), magnesium sulfate (CASRN: 7487-88-9), calcium sulfate (CASRN: 7778-18-9), lithium hydroxide (CASRN: 1310-65-2), lithium fluoride (CASRN: 7789-24-4) or similar. dextran (CASRN 9004-54-0), and BSA (CASRN 9048-46-8) Can also be included to improve the viscosity and osmotic properties.

The pH is then adjusted to around 7.65 1 N or 0.1 N NaOH or 0.1 N HCl, such that after the addition of ascorbate the final pH is about 6.9-7.35. The solution is stored in 100 ml-1000 ml dispense bottle to allow easy eye washing. The Part 1 (liquid) bottle, can also have a spray top suitable for administering a laminar flow across the eye to allow washing for at least 1 (100 ml) minutes and preferably 15 minutes (1 liter). The bottle top of the bottle may have a compartment with a twist aperture to hold the second component (ascorbate) or the ascorbate may be attached to the bottle or a separate packet.

Part 2 is composed a granular ascorbate solution, formulated such that it rapidly dissolves within part 1 upon shaking. The ascorbate powder may consist of any of the following: sodium ascorbate (CASRN: 134-03-2), calcium ascorbate (CASRN: 5743-28-2), ascorbic acid, (CASRN: 50-81-7), potassium ascorbate (CASRN: 15421-15-5), magnesium L-ascorbate (CASRN: 15431-40-0), dehydro-L-(+)-ascorbic acid dimer (CASRN: 72691-25-9), ascorbic acid 6-palmitate (CASRN: 137-66-6), 5,6-Isopropylidene-L-ascorbic acid (CASRN: 15042-01-0), 2-Phospho-L-ascorbic acid trisodium salt (CASRN: 66170-10-3), 2-O-a-D-Glucopyranosyl-L-ascorbic acid (CASRN: 129499-78-1), 5,6-O-benzylidene-2,3-dideoxy-L-ascorbic acid (CASRN: 1217498-73-1), oxalic acid (CASRN: 144-62-7), ascorbyl stearate (CASRN: 10605-09-1), erythorbic acid (CASRN: 89-65-6), glyceryl ascorbate (CASRN: 1120360-13-5), 3-O-Ethyl-L-ascorbic acid (CASRN: 86404-04-8), L-ascorbic acid 2-phosphate sesquimagnesium salt hydrate (CASRN: 1713265-25-8), (L)-Dehydroascorbic acid (CASRN: 490-83-5), 2,6-Dichlorophenol-indophenol sodium salt dihydrate (CASRN: 620-45-1), L-ascorbyl 2,6-Dibutyrate (CASRN: 4337-04-6), L-ascorbic acid-2-13C (CASRN: 178101-89-8) or similar.

Examples

Sodium Hypochlorite Exposure and Rinsing

Immediately prior to each experiment (<1 hour), 32% sodium hypochlorite (CASRN 7681-52-9, Sigma-Aldrich, St. Louis, USA) was prepared by freshly diluting in sterile deionized (DI) water, mixed by five tube inversions prior to each application, and applied directly to the eyes (corneas) by transferring 100 μL with a micropipette into the dosing ring and the eyes were then exposed to this solution for exactly 1 minute. Immediately after exposure, corneas were rinsed by forcefully dispensing 20 mL of either saline (0.9 g/L NaCl) and washed with control or ascorbate solution (as described below).

Wash Solution Preparation

Wash solution was made in a device filled similar to devices shown in FIG. 5-9, as described:

1) Liquid Portion

The liquid portion of the wash solution was made days-months in advance and stored in wash container. In this example the liquid formulations included: potassium chloride (CASRN 7447-40-7, 2.7 mM), potassium phosphate monobasic (CASRN 7778-77-0, 1.5 mM), sodium chloride (CASRN 7647-14-5, 137.9 mM), sodium phosphate dibasic (CASRN 7782-85-6, 8.1 mM) and DI water.

2) Solid Portion

The solid portion was premeasured into 0.5 ml dispersion tubes which are part of the wash station. In this example, L-ascorbic acid powder was weighed in the tubes above the chamber that houses the bottle of liquid portion. When the handle is lifted, the solid portion dumps into the liquid and the battery operated rotating paddle begins mixing the solution in the wash station. (the later step performed right before washing, as described below:

Corneas were then exposed to 32% sodium hypochlorite for 1 minute. After exposure, the wash station was activated by lifting the handle, and the eyes were washed with the battery operated lateral flow jet of eye wash that comes from the eye nozzle when it is lifted up towards the eye. This wash solution is called "AA". In a second condition, no powder was loaded into the machine, and this is identified below as control. This wash solution is called Control (C). Bothe AA and C are used to compare the efficacy of the ascorbate solution in reducing eye damage. The eyes were each washed for a defined period of time (described below).

2.7 Postexposure

After washing, eyes were placed in fresh postexposure wells (Lebrun Labs LLC, Anaheim, CA) containing approximately 1.2 mL of OM added to the level of the limbus. Eyes were then placed back into a humidified, 5% $CO_2$, 37° C. incubator for 24 hours. The next day, corneas were removed, placed in 4% paraformaldehyde in PBS (Boston BioProducts, Inc., Milford, USA) fixative, and stored at 4° C.

Tissue processing and TUNEL labeling, After a minimum of 24 hours in fixative, corneas were cut in half and infiltrated with 30% sucrose (Capella et al., 1965), and the tissues were then embedded in Tissue-Tek® O.C.T. Compound (Sakura Finetek, Torrance, CA), snap frozen in liquid nitrogen, and stored in an ultralow freezer (−80° C., New Brunswick Scientific, Hamburg, Germany). Using a cryostat (Leica CM 1900 UV, Leica Biosystems, Deer Park, USA), nine 8-μm-thick tissue sections were collected at 100-μm intervals and placed onto glass slides (Superfrost Plus Microscope Slides White Tab, Fisher Scientific, Pittsburgh, USA), alternating between slides so that the greatest depth of sampling was achieved (three sections/slide).

Sections were then stained for apoptosis- and necrosis-related DNA fragmentation (Stadelmann and Lassmann, 2000) with endonuclease terminal deoxynucleotidyl transferase dUTP nick-end labeling (TUNEL) of the 3'-hydroxyl termini of double stranded DNA breaks by TUNEL part of the IVD™ kit (Lebrun Labs LLC, Anaheim, CA). Images were counterstained for DAPI. DAPI binds A-T rich regions of double stranded DNA and forms a fluorescent complex and indicates the locations live or dead cell nuclei. Prior to imaging, coverslips were applied to the slides using a mounting solution (Lebrun Labs LLC, Anaheim, CA).

Data Collection and Analysis

Figure 1B:
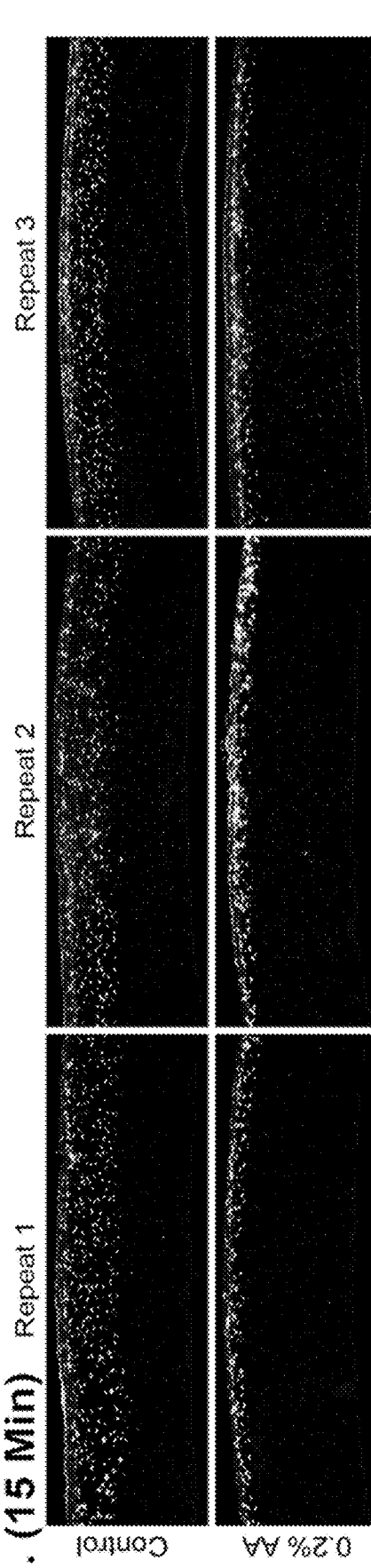
Figure 1C:
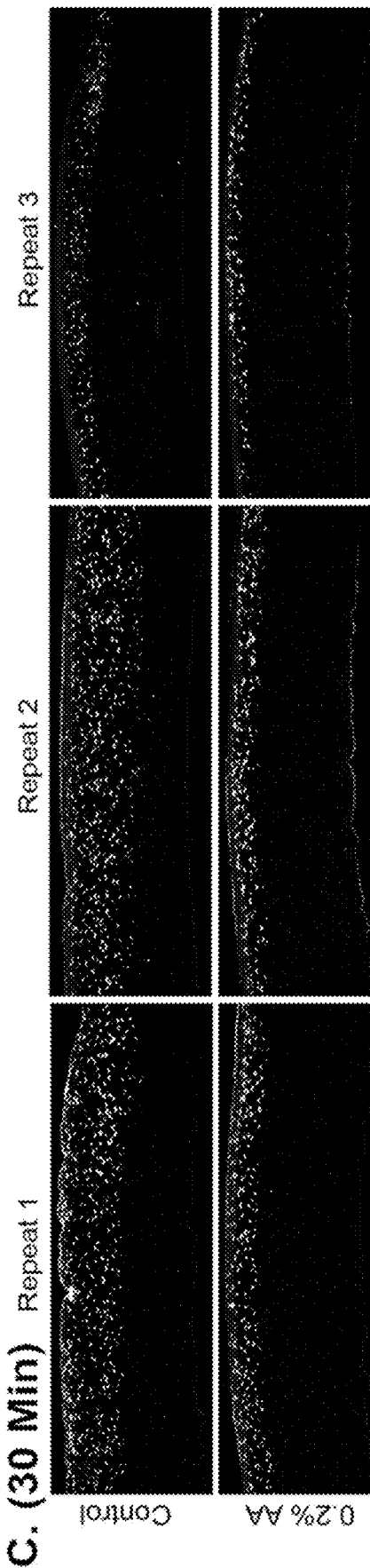
Figure 1D:
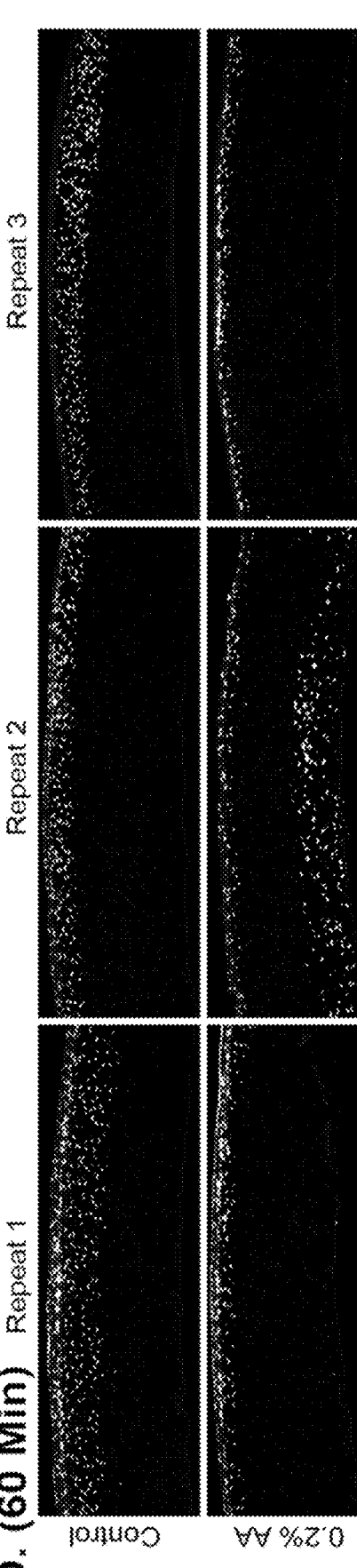

Stained sections were viewed using a Leica DMRE fluorescence microscope (Leica Microsystems Inc., Buffalo Grove, IL). Images were collected using a low-light-level camera (Kiralux 2.3 MP Monochrome CMOS Camera, Thorlabs, Newton, NJ) and Leica 5x/0.15 HC PL Fluotar objective. An L5 Fluorescence Filter Cube (Leica Microsystems Inc., Buffalo Grove, IL) was used for TUNEL imaging, and an A4 Fluorescence Filter Cube (Leica Microsystems Inc., Buffalo Grove, IL) was used for DAPI imaging. Images were processed and analyzed using ImageJ software, version 1.54. TUNEL and DAPI images were combined using the "Merge Channels" feature to form a composite image with TUNEL represented in white and DAPI represented in blue. ImageJ software was also used to process and analyze the images (Schneider et al., 2012). Three corneal cryosections (each approximately 13 mm long and 1 mm wide) were measured for each eye. To count TUNEL-positive nuclei, the number of discrete TUNEL-positive nuclei were recorded for each section. For DoI calculations, the thickness of the entire stroma from the end of the corneal epithelium (Epithelium) to the beginning of the corneal endothelium (Endothelium) was measured. Stromal depth of injury was determined by calculating the depth of the TUNEL-positive stroma by the total stromal thickness. The average number of dead cells and average stromal DOI were then calculated for each section, and the averages of three sections were recorded for each eye. As discussed further in the results section (FIG. 1B), for TUNEL-positive analysis, measurements were limited to assessing the stroma since there is a concern that epithelial injury caused by 32% NaOCl was confounded by dead epithelial cell sloughing and/or epithelial cell disintegration that obscures the identification of discrete TUNEL-positive nuclei.

Statistics

Data were statistically analyzed using Excel software. TUNEL-positive and DoI averages and standard deviations were calculated using the built-in functions found in Excel. Differences between groups were assessed for significance with ANOVA, and P values are shown for each comparison to quantify the significant differences between the treatment and control groups. For each study, P values were determined by selecting the lowest P value where each specific comparison between the control group and the AA group were significantly different. Throughout the text, numbers are represented as averages±the standard deviation.

Corneas were exposed to 32% sodium hypochlorite for 1 minute, rinsed, and washed for 15 minutes. Washing in wash buffer with or without 0.2% AA was either initiated immediately or the eyes were placed in incubation dishes with OM up to the limbus and placed in the incubator (with 37° C., 5% $CO_2$, humidity) for a 10- or 120-minute incubation prior to a 15-min wash in wash buffer with or without 0.2% AA. After "washing," eyes were processed following the "postexposure" steps described below.

Postexposure After washing, eyes were placed in fresh postexposure wells (Lebrun Labs LLC, Anaheim, CA) containing approximately 1.2 mL of OM added to the level of the limbus. Eyes were then placed back into a humidified, 5% $CO_2$, 37° C. incubator for 24 hours. The next day, corneas were removed, placed in 4% paraformaldehyde in PBS (Boston BioProducts, Inc., Milford, USA) fixative, and stored at 4° C.

Tissue processing and TUNEL labeling. After a minimum of 24 hours in fixative, corneas were cut in half and infiltrated with 30% sucrose (Capella et al., 1965), and the tissues were then embedded in Tissue-Tek® O.C.T. Compound (Sakura Finetek, Torrance, CA), snap frozen in liquid nitrogen, and stored in an ultralow freezer (−80° C., New Brunswick Scientific, Hamburg, Germany). Using a cryostat (Leica CM 1900 UV, Leica Biosystems, Deer Park, USA), nine 8-μm-thick tissue sections were collected at 100-μm intervals and placed onto glass slides (Superfrost Plus Microscope Slides White Tab, Fisher Scientific, Pittsburgh, USA), alternating between slides so that the greatest depth of sampling was achieved (three sections/slide).

Sections were then analyzed for corneal cell death by staining apoptosis- and necrosis-related DNA fragmentation (Stadelmann and Lassmann, 2000) with endonuclease terminal deoxynucleotidyl transferase dUTP nick-end labeling (TUNEL) of the 3'-hydroxyl termini of double stranded DNA breaks using a commercially available TUNEL labeling kit (TUNEL Assay Kit—FITC, Abcam, Cambridge, United Kingdom) (Gavrieli et al., 1992; Gorcyca et al., 1993) supplemented with TUNEL enzyme (Sigma-Aldrich, St. Louis, USA) and ChromaTide Alexa Fluor 488-5 UTP (Thermo Fisher Scientific, Waltham, USA). Images were counterstained for DAPI. DAPI binds A-T rich regions of double stranded DNA and forms a fluorescent complex and indicates the locations live or dead cell nuclei. Prior to imaging, coverslips were applied to the slides using a mounting solution (Lebrun Labs LLC, Anaheim, CA).

Data Collection and Analysis

Stained sections were viewed using a Leica DMRE fluorescence microscope (Leica Microsystems Inc., Buffalo Grove, IL). Images were collected using a low-light-level camera (Kiralux 2.3 MP Monochrome CMOS Camera, Thorlabs, Newton, NJ) and Leica 5x/0.15 HC PL Fluotar objective. An L5 Fluorescence Filter Cube (Leica Microsystems Inc., Buffalo Grove, IL) was used for TUNEL imaging, and an A4 Fluorescence Filter Cube (Leica Microsystems Inc., Buffalo Grove, IL) was used for DAPI imaging. Images were processed and analyzed using ImageJ software, version 1.54. TUNEL and DAPI images were combined using the "Merge Channels" feature to form a composite image with TUNEL represented in white and DAPI represented in blue. ImageJ software was also used to process and analyze the images (Schneider et al., 2012). Three corneal cryosections (each approximately 13 mm long and 1 mm wide) were measured for each eye. To count TUNEL-positive nuclei, the number of discrete TUNEL-positive nuclei were recorded for each section. For DoI calculations, the thickness of the entire stroma from the end of the corneal epithelium (Epithelium) to the beginning of the corneal endothelium (Endothelium) was measured. Stromal depth of injury was determined by calculating the depth of the TUNEL-positive stroma by the total stromal thickness. The average number of dead cells and average stromal DoI were then calculated for each section, and the averages of three sections were recorded for each eye.

Statistics

Data were statistically analyzed using Excel software. TUNEL-positive and DoI averages and standard deviations were calculated using the built-in functions found in Excel. Differences between groups were assessed for significance with ANOVA, and P values are shown for each comparison to quantify the significant differences between the treatment and control groups. For each study, P values were determined by selecting the lowest P value where each specific comparison between the control group and the 0.2% AA group were significantly different. Throughout the text, numbers are represented as averages±the standard deviation.

Results

TUNEL staining indicates the locations of dead cells, whereas DAPI staining indicates the locations of all cells (live and dead).

Figure 3A:
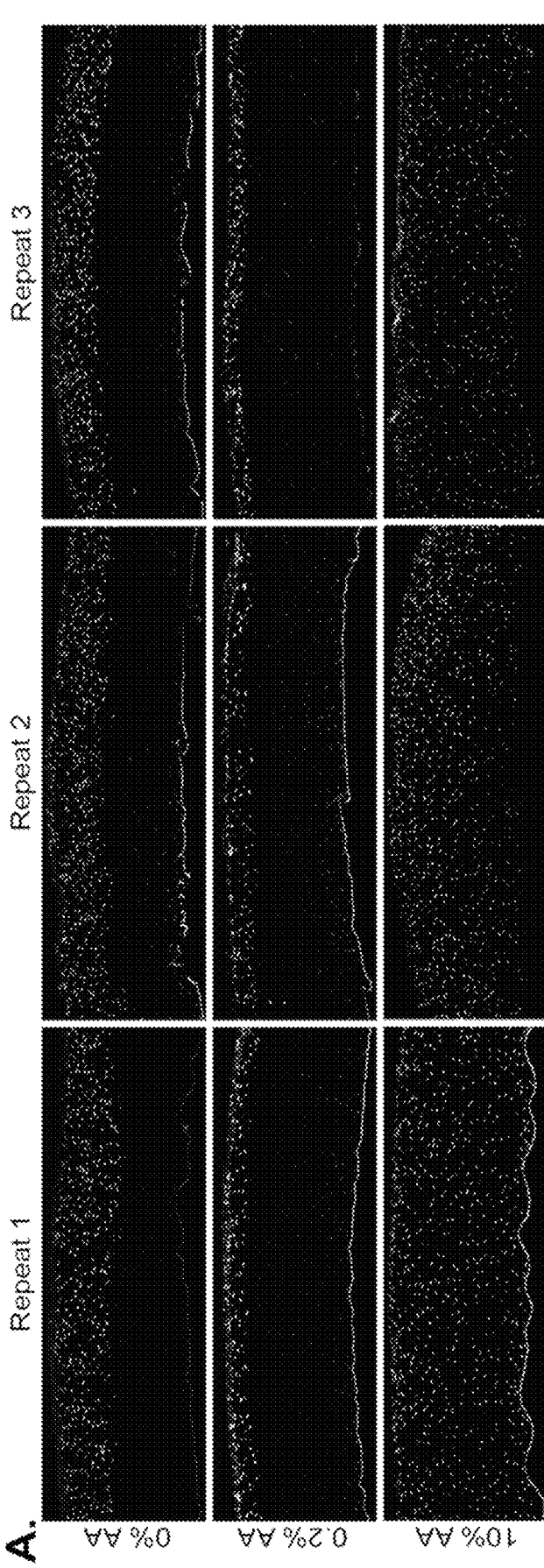
FIGS. 3A-3C: depicts the time until washing is initiated after the rabbit eye is exposed to sodium hypochlorite. White=dead cells of the cornea. Blue=live cells of the cornea

FIG. 1 shows triplicate results for eyes exposed to 32% NaOCl followed by immediate washing for 1,15, 30, and 60 minutes with either wash buffer or wash buffer with 0.2% AA. Corneas washed with AA have significantly less dead cells as indicated by the white TUNEL staining (shown in white) at each wash duration. For example, FIG. 1B shows that eyes washed with AA for 15 minutes had considerably less TUNEL staining than controls. In fact, even a 1-minute wash resulted in a considerable reduction in TUNEL staining (FIG. 3A). While in each case, the three-eye average TUNEL staining was less for the AA condition at each time point, after 60 minutes of washing, TUNEL results appear more varied. Also, Repeat 2 of the 0.2% AA group at 60 minutes showed anomalous TUNEL staining on the endothelial side of the cornea section (believed to have resulted from a bubble during the fixation step); thus, this region was excluded from the data analysis. While a technical error is believed to be the cause of the abnormal staining pattern, additional repeats of this treatment condition would be necessary to verify this.

Figure 2A:
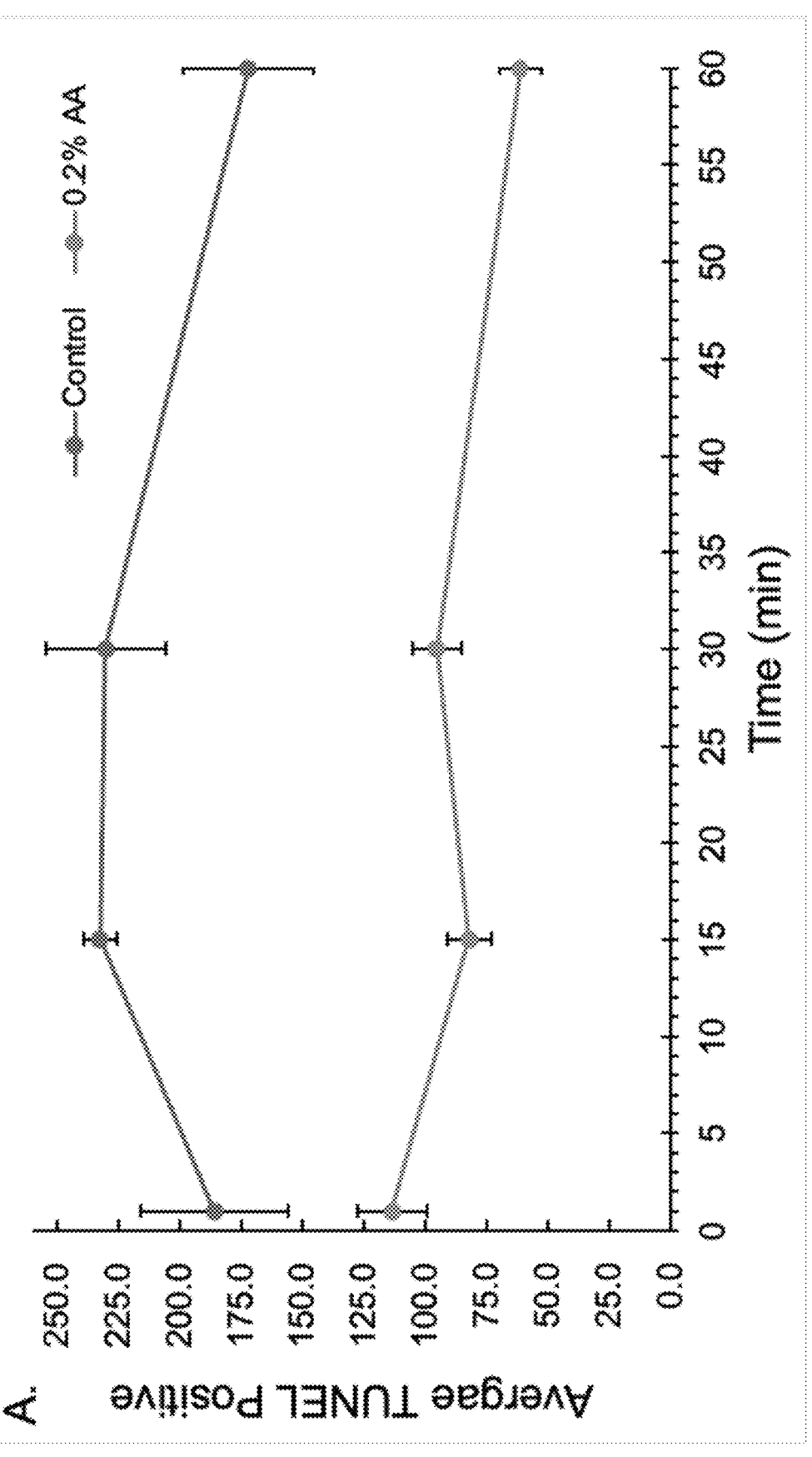
FIGS. 2A-2B: depicts the results from FIGS. 1A-1D and compares the control wash with the 0.2% Ascorbic acid wash.
Figure 2B:

As shown in FIGS. 2A and 2B, with 1 minute washing, the number of TUNEL-positive nuclei (dead cells) decreased significantly from 186.0±14.6 in the control group to 113.8±9.2 in the 0.2% AA group (P<0.001). Likewise, the stromal DoI was higher in the control group with an average of 27.3±2.9 compared to an average of 12.7±1.2 in the 0.2% AA group with just 1 minute of washing (P<0.001). With a 15-minute wash, the 0.2% AA group had an average number of TUNEL-positive nuclei of 82.2±10.9, which was significantly less than the control of 232.6±15.7 (P<0.001). These findings coincide with the average stromal DoI of 8.0±0.6 in the 0.2% AA group and 34.8±4.1 in the control after a 15-minute wash (P<0.001). With a 30-minute wash, the number of TUNEL-positive nuclei significantly decreased between the control corneas with an average of 230.3±79.2 and corneas treated with 0.2% AA with an average of 95.6±32.0 (P<0.001). Corneas treated with 0.2% AA had an average DoI of 10.9±3.4, which was significantly less than that of control corneas with an average DoI of 35.6±13.0 at 30 minutes (P<0.001). After a 60-minute wash, the average number of TUNEL-positive nuclei significantly decreased from 172.2±18.2 in the control group to 61.5±1.0 in the 0.2% AA group (P<0.001), and the stromal DoI is higher in the control group with an average of 23.3±7.1 compared to an average of 7.0±2.1 in the 0.2% AA group (P<0.001).

Wait before wash study.

Figure 5:
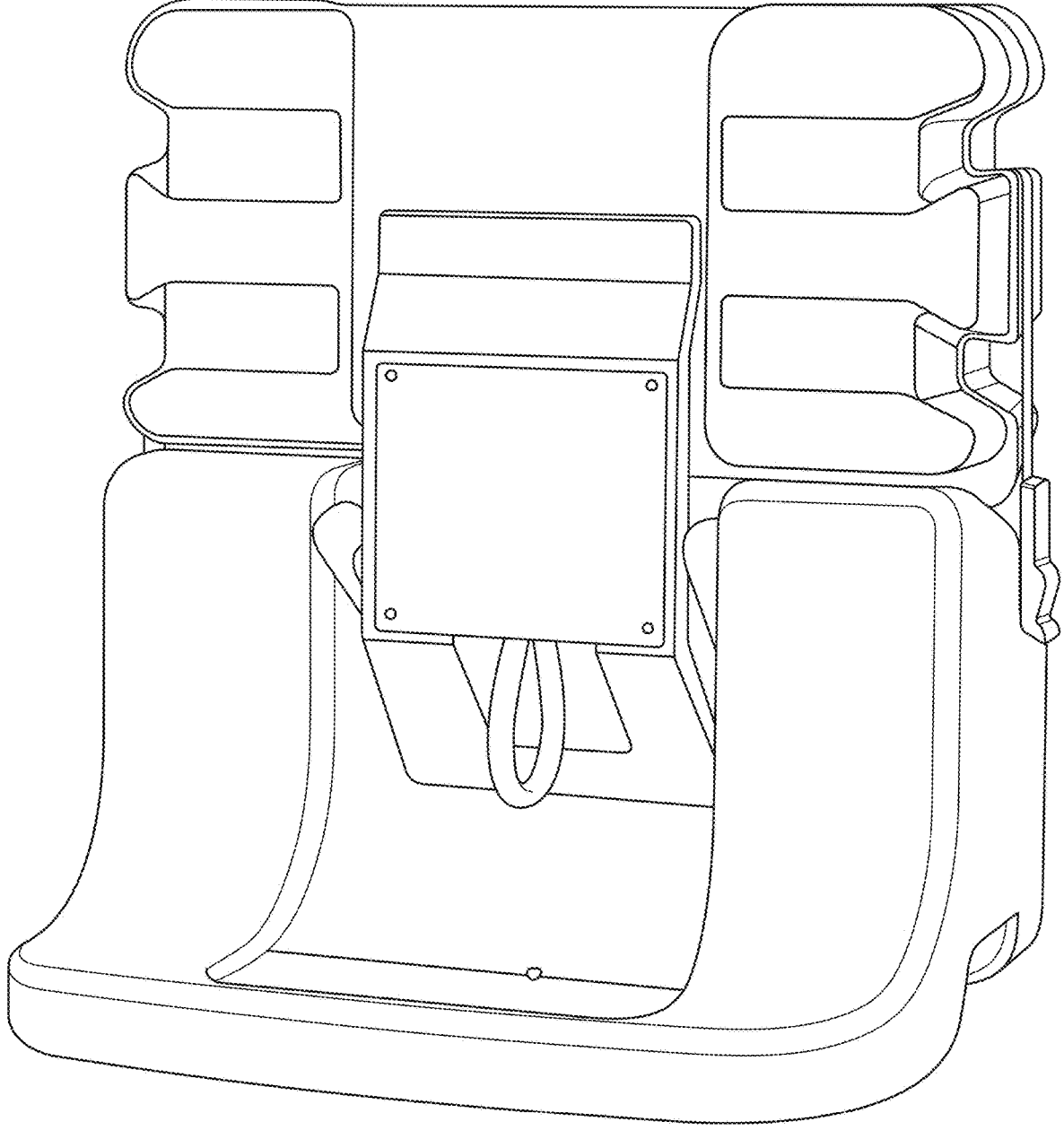
FIG. 5: depicts an example of an on-site eyewash station (see Reference: https://www.zoro.com/bradley-on-site-eye-wash-station-in-yellow-s19-921/i/G1626387/?msclkid=55e74ec4f0661d61fb042b09de329095&utm_source-bing&utm_medium=cpc&utm_campaign=ml_all_dyn_na_ssc_Bing%20core&utm_term=4585788126739859&utm_content=Core&gclid=55e74ec4f0661d61fb042b09de329095&gclsrc=3p.ds).
Figure 6:
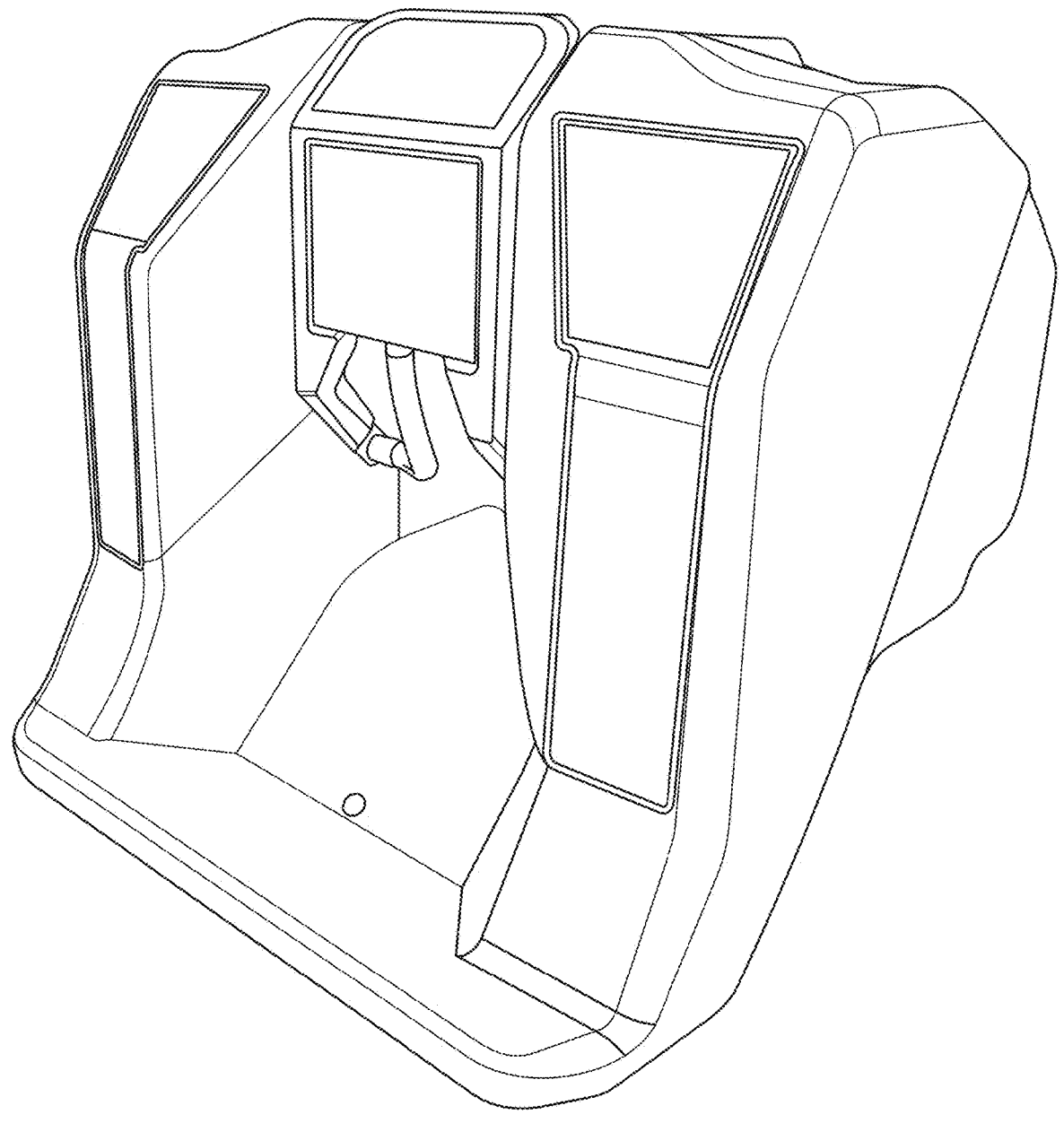
FIG. 6: depicts an example of an emergency on-site eyewash station. (See Reference: https://www.industrial-safetyproducts.com/radians-rew01116-visionaid-16-gallon-emergency-eyewash-station/
?gad_source=1&gclid=EAIaIQobChMI-
MyVjIqshAMVjS7UAR094QgaEAYYBiABEglbgvD_
BwE).
Figure 7:
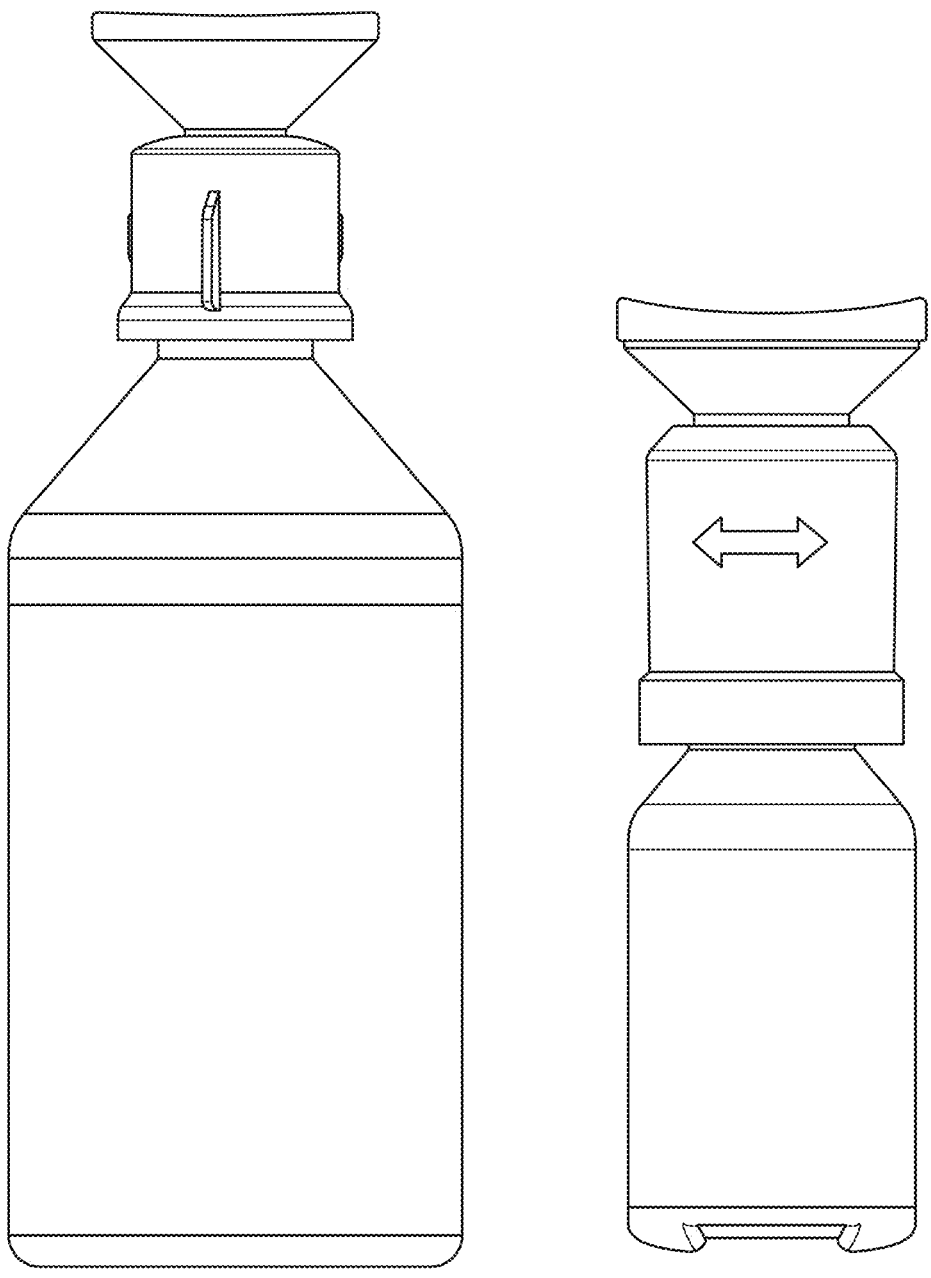
FIG. 7: depicts an example of an eyewash bottle pack. (See Reference: https://www.accidental.com.au/first-aid-supplies/eye-care/eye-irrigation/eye-shower-emergency-pack.html).
Figure 8:
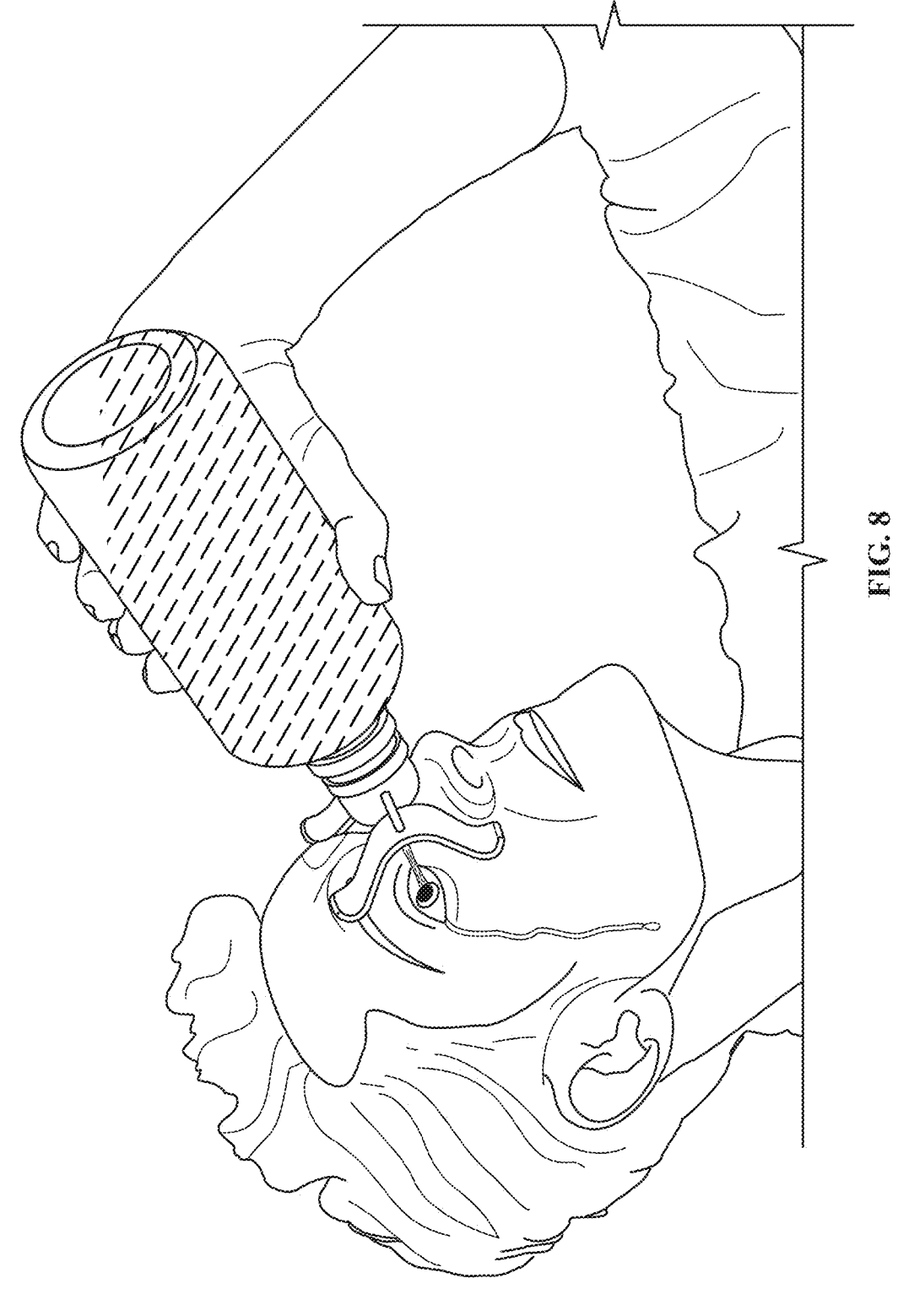
FIG. 8: depicts an example of a single bottle personal eyewash. (See Reference: https://iqsafetyproducts.com.au/single-bottle-personal-eyewash-station)
Figure 9:
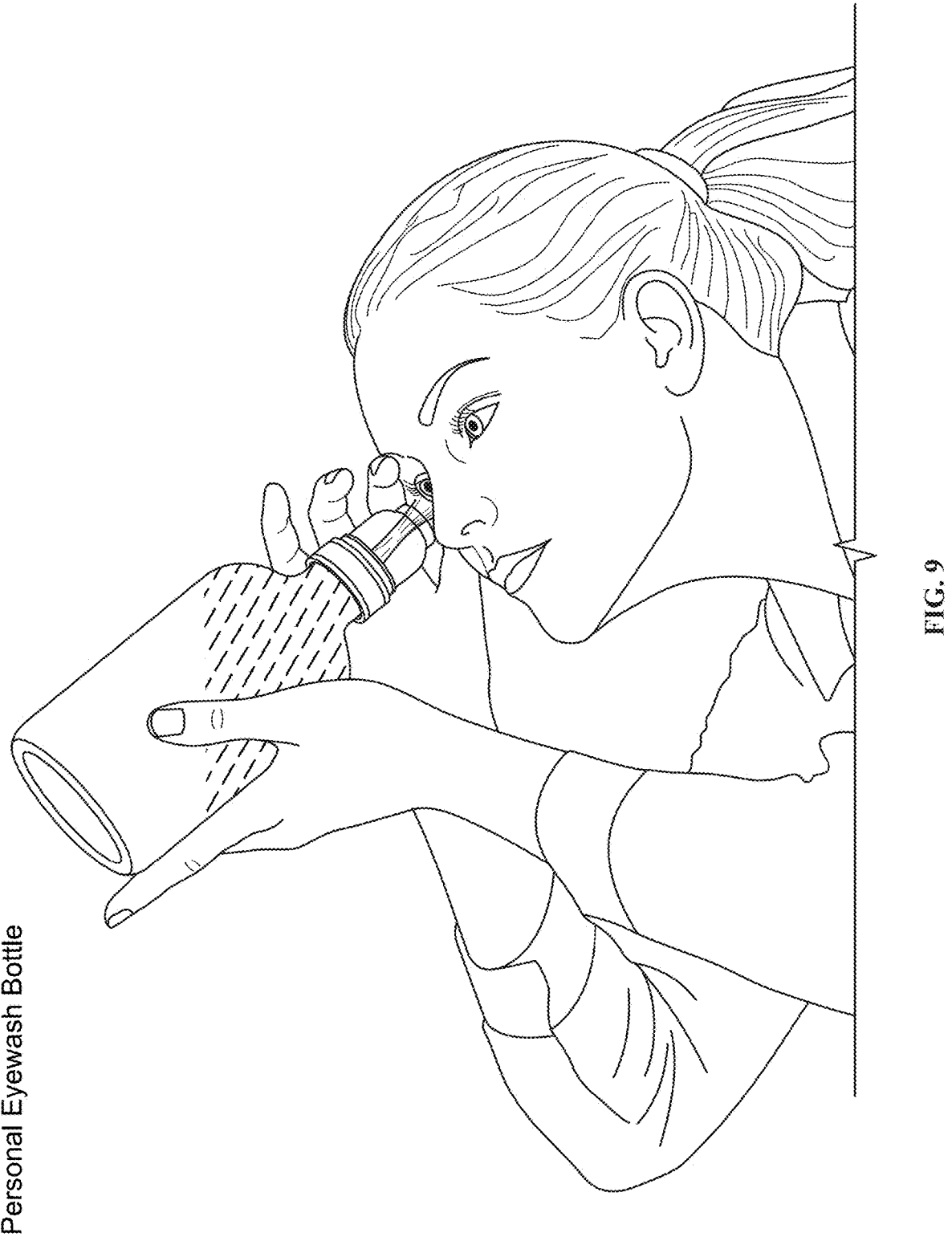
FIG. 9: depicts an example of a personal eyewash bottle. (see Reference: https://www.chinalongbow.com/eye-wash/)
Figure 10:
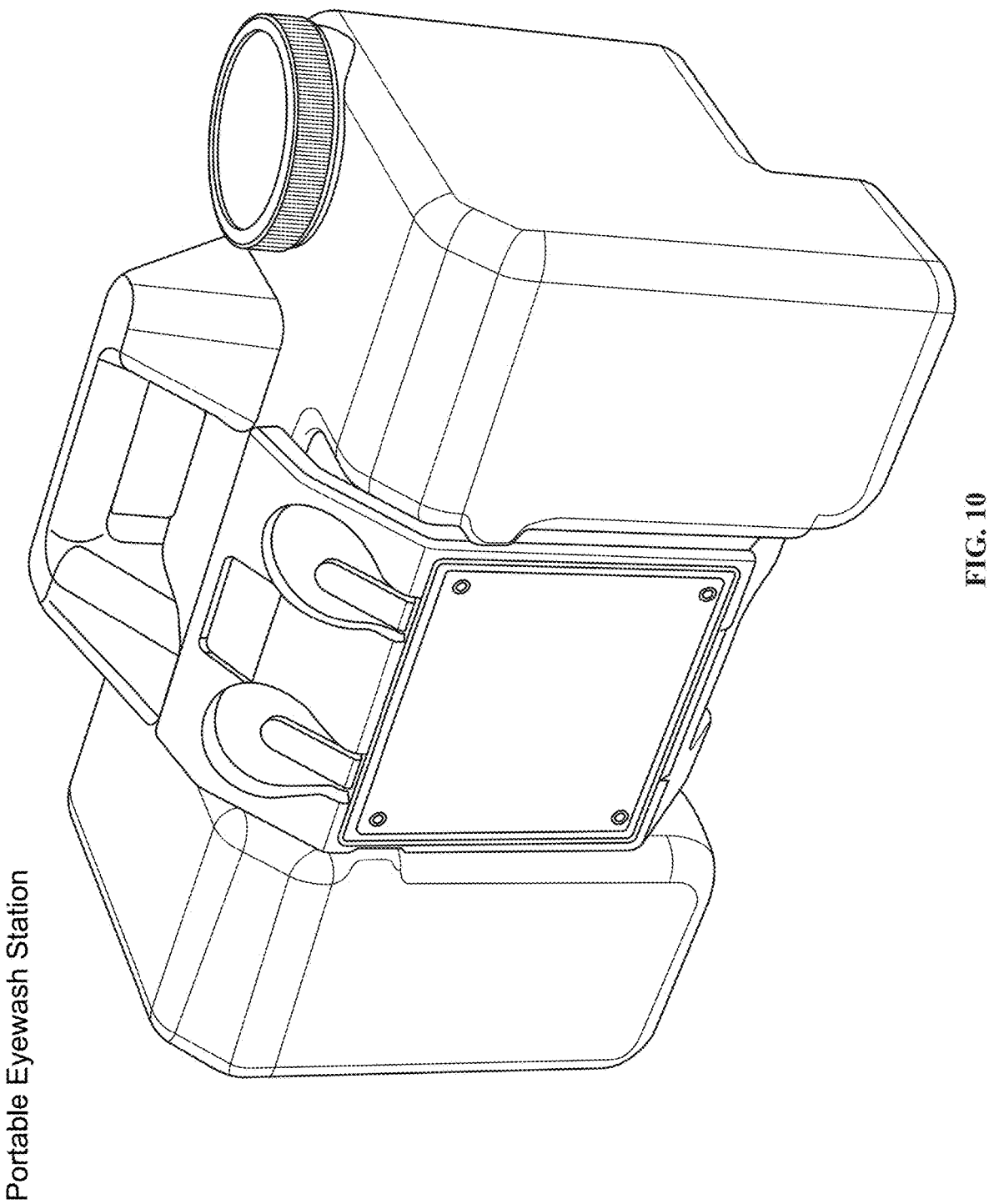
FIG. 10: depicts an example of a portable eyewash station. (See Reference: https://redasafe.com/sa_en/haws-portable-7501-gravity-fed-heewash-9-gallon).
Figure 11:
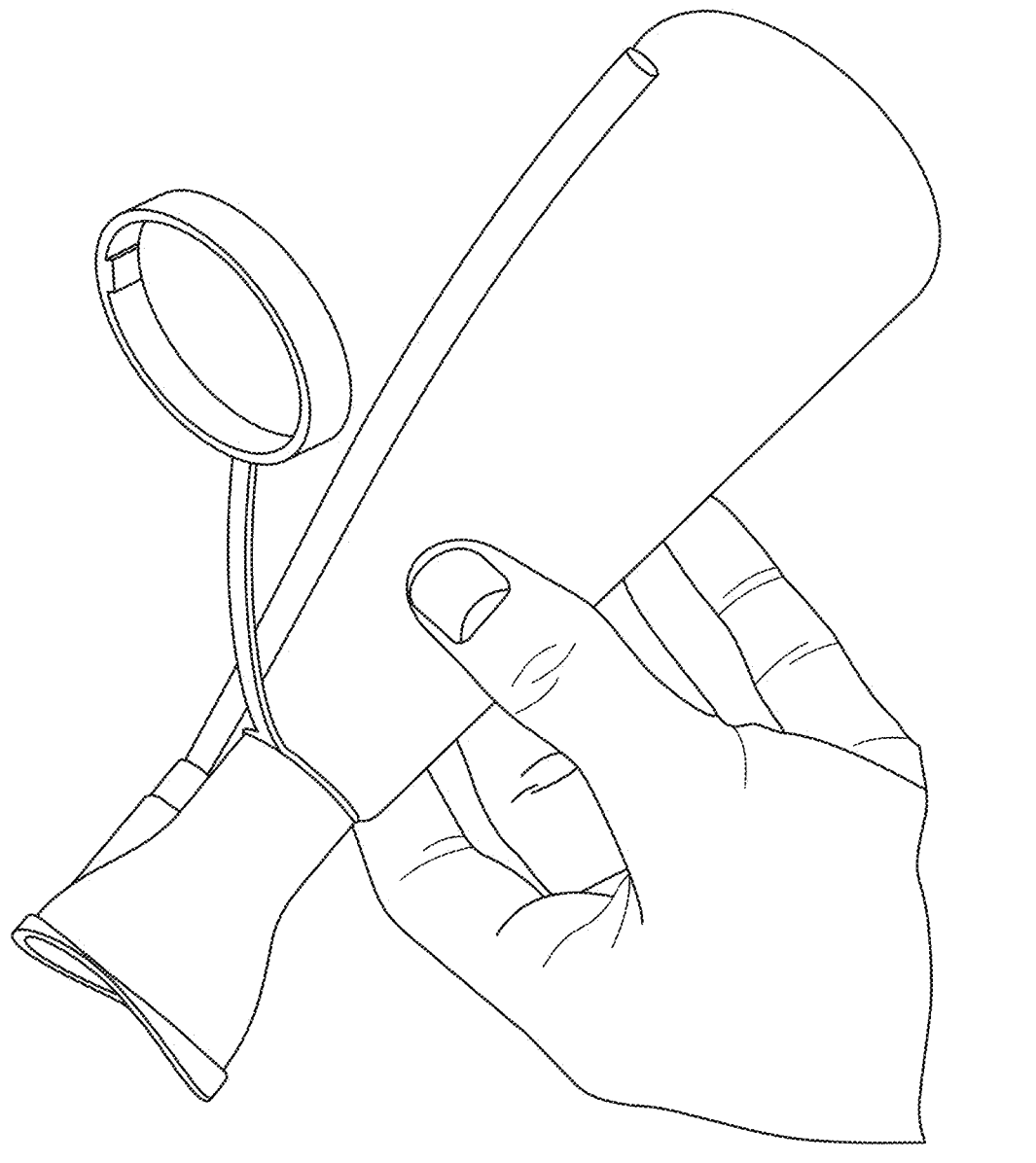
FIG. 11: depicts an example of an eyewash bottle that covers the eye. (See Reference: https://koreaemarket.com/product/eye-wash-cup-300 ml-capacity-for-eye-cleanin-gremoving-dirtforeign-subsances-while-working-bpa-free-portable-emergency-removal-foreign-matter-eye-clean-removal-system-with- pressing-pipet-eye-wash/).

In another study, how quickly washing must be initiated was studied. AA wash was formulated as described above and used just after injury, 10 minutes after injury or 2 hours after injury. In addition, a second solution of 10% ascorbic acid (10 g/100 ml) was made. However this solution took 3.5 hours of rapid mixing to fully go into solution and the another 1.5 hours to adjust the pH which initially feel below to a pH of 3.25. FIG. 5 shows the images while FIG. 6 shows the averages±SD for triplicate results for eyes exposed to 32% NaOCl, and then washed immediately, after 10 minutes, or after 2 hours for 15 minutes with wash buffer, C wash buffer, AA wash buffer, or wash buffer with 10% AA. Corneas immediately washed with AA had significantly less TUNEL staining (shown in white) than those washed with buffer alone.

Figure 3B:
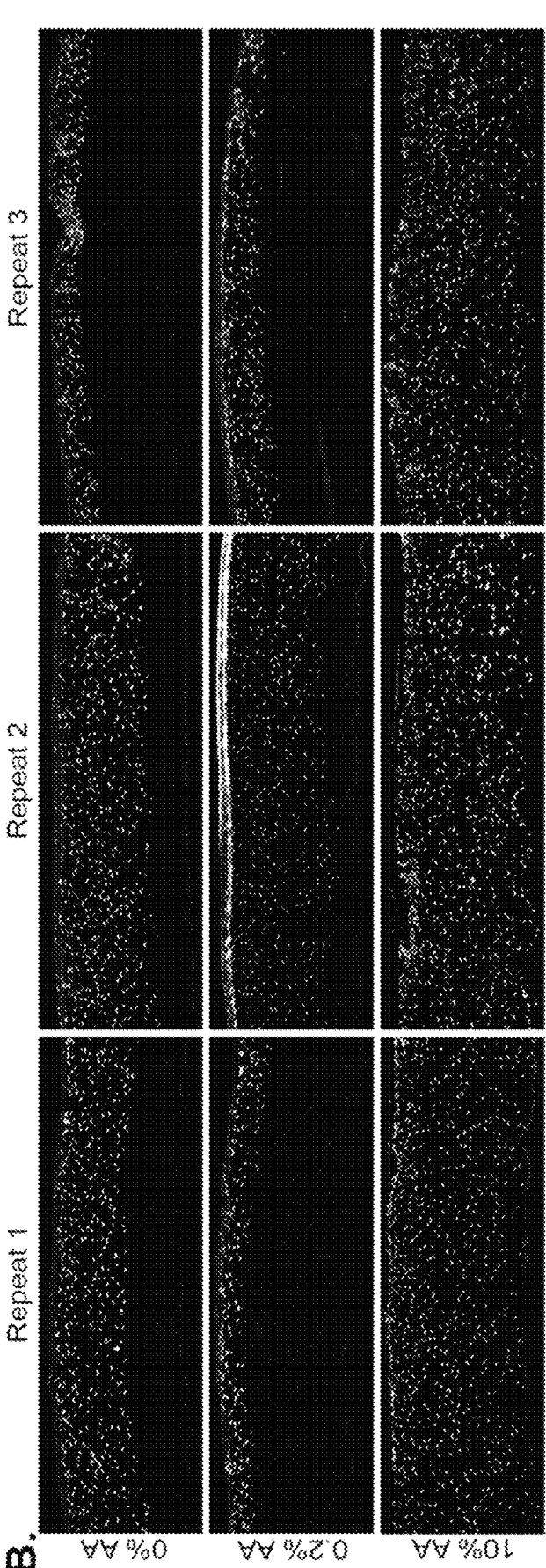
Figure 3C:
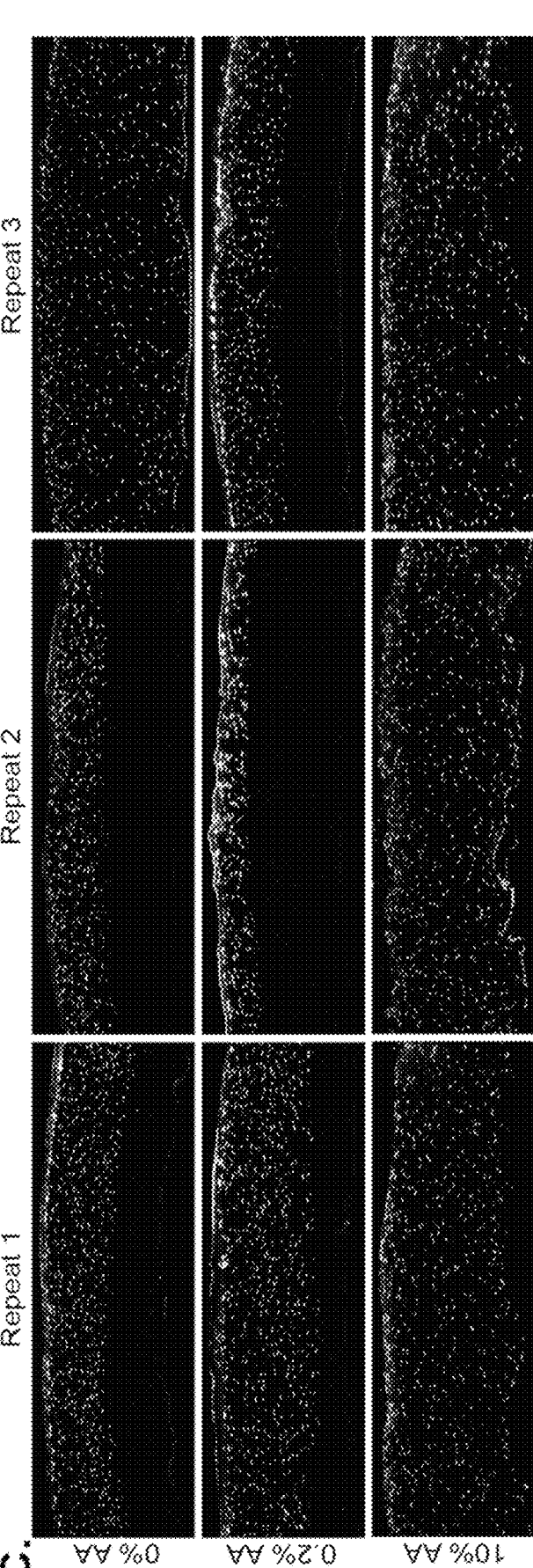
Figure 4A:
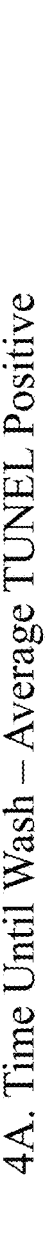
FIGS. 4A-4B: depicts the results from FIGS. 3A-3C and compares the control wash with the 0.2% Ascorbic acid wash.
Figure 4B:
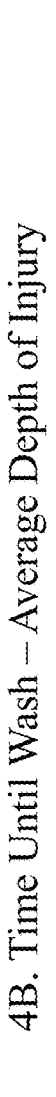

As shown in FIGS. 3A and 3B, the number of stromal TUNEL-positive nuclei significantly decreased from an average of 306.4±28.4 in the control group to an average of 69.2±7.4 for the 0.2% AA group after immediate washing (P<0.001). Likewise, the stromal DoI significantly decreased from an average of 34.9±2.2 for the control group to an average of 9.9±1.3 for the 0.2% AA group (P<0.001). When washing was initiated 10 minutes after NaOCl exposure, the control group had an average number of TUNEL-positive nuclei of 294.7±67.7 while the 0.2% AA group had a significantly lower average of 199.7±75.3 (P<0.05). There was also a decrease in the stromal DoI between the control, with an average of 44.4±20.7, and the 0.2% AA group, with an average of 37.4±21.1 (P<0.05), but both were above 20% DoI, which predicts severe eye injury. When washing is initiated after 120 minutes, the average number of TUNEL-positive nuclei was 512.1±71.8 for the 0.2% AA group, which was significantly lower than the average of 401.4±77.1 for the control (P<0.05). There was also a decrease in the DoI for the 0.2% AA group (average DoI of 42.8±19.3) compared to the control group (average DoI of 65.4±25.2; P<0.001); however, there was an increase in DoI in both the control and AA treatment groups, resulting in a treatment group DoI significantly above 20%, which unlike the other conditions, is predicted to cause severe eye injury. It is unclear why the DoI for both the control and AA groups were so high after 2 hours.

As disclosed herein, the inventors have discovered that immediate (within 10 minutes) high volume (more than 10 mls, 100-1000 mls preferred) washing of the eye for 1-15 minutes with a low concentration (5-17 mM) of a freshly made ascorbate solution with a pH between 6 and 6.99 after chemical exposure, for example after accidental or malicious splash or spray, results in significantly reduced eye damage. Disclosed is a product and device to make such a mediating procedure readily available, by overcoming the inherent decay and loss of activity with time of ascorbate n solution, and the inherent toxicity of buffered ascorbate which results pH in an acid range that can cause acid burn to the cornea.

As shown in the examples, a 10% AA (57 mM) results in total death of the cornea for all time points using our device and procedure. Hence we strongly teach away from 10% ascorbate. In fact anything we teach away from above 3% (17 mM), which can be considered the absolute upper concentration limit. In addition, concentration above 17 mM will not readily go into solution, and will buffer into the extreme acid pH range if not well mixed. For these reasons the applicable range of AA is 5.7-17 mM.

As shown in the examples, waiting for longer than 10 minutes results in results in more eye damage. For this reason, time is of the essence and the eye wash station is highly useful because it can rapidly mix, account for pH near neutral and be dispensable very rapidly for real world situations. Since ascorbates are highly unstable in solution, they cannot be store ready to use for eye washing. This device should be readily available in chemical or military settings for immediate medial use; such use can potentially save vision. As shown by the use examples, the device and method reduce depth of injury below the crucial 20% depth of injury to the cornea associated with permeant eye damage and vision degradation or loss.

While various aspects and embodiments have been disclosed herein, other aspects and embodiments will be apparent to those skilled in the art.

The various aspects and embodiments disclosed herein are for purposes of illustration and are not intended to be limiting, with the true scope and spirit being indicated by the following claims.

One skilled in the art will appreciate that this and other processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

BIBLIOGRAPHY

Adedara I A., Farombi E O. (2014). "Kolaviron protects against ethylene glycol monoethyl ether-induced toxicity in boar spermatozoa". Andrologia. 46(4): 399-407. doi: 10.1111/and.12095.

Babizhayev M A. (2016). "Generation of reactive oxygen species in the anterior eye segment. Synergistic codrugs of N-acetylcarnosine lubricant eye drops and mitochondria-targeted antioxidant act as a powerful therapeutic platform for the treatment of cataracts and primary glaucoma". open-angle BBA Clin. 6:49-68. doi: 10.1016/j.bbacli.2016.04.004.

Behndig A., Svensson B., Marklund S L., Karlsson K. (1998). "Superoxide dismutase isoenzymes in the human eye". Invest Ophthalmol Vis Sci. 39(3): 471-5.

Belvedere G., Tursi F. (1981). "Styrene oxidation to styrene oxide in human blood erythrocytes and lymphocytes". Research Communications in Chemical Pathology and Pharmacology. 33(2): 273-282.

Bodin A., Linnerbord M., Nilsson J L G., Karlberg A T. (2003). "Structure elucidation, synthesis, and contact allergen activity of a major hydroperoxide formed at autoxidation of the ethoxylated surfactant C12E5". Chem Res Toxicol. 16(5): 575-82. doi: 10.1021/tx025609n Cabrera M P., Chihuailaf R H. (2011). "Antioxidants and the integrity of ocular tissues". Vet Med Int. 905153. doi: 10.4061/2011/905153.

Carlson G P., Turner M., Mantick N A. (2006). "Effects of styrene and styrene oxide on glutathione-related antioxidant enzymes". Toxicology. October 29; 227(3): 217-26. doi: 10.1016/j.tox.2006.08.006.

Carr A C., Maggini S. (2017). "Vitamin C and Immune Function". Nutrients. 9(11): 1211. doi: 10.3390/nu9111211

Chen C., Jiang X. (2019). "Transport property prediction and inhomogeneity analysis of supercritical n-Dodecane by molecular dynamics simulation". Fuel. 244: 48-60. doi: 10.1016/j.fuel.2019.01.181.

Chen Y., Mehta G., Vasiliou V. (2009). "Antioxidant defenses in the ocular surface". Ocul Surf. 7(4): 176-185. doi: 10.1016/s1542-0124(12) 70185-4.

Chirila T V., Walker L N., Constable I J., Thompson D E., Barrett G D. (1991). "Cytotoxic effects of residual chemicals from polymeric biomaterials for artificial soft intraocular lenses". J Cataract Refract Surg. 17(2): 154-62. doi: 10.1016/s0886-3350(13) 80245-3

Choksi N., Lebrun S., Nguyen M., Daniel A., DeGeorge G., Willoughby J., Layton A., Lowther D., Merrill J., Matheson J., Barroso K., Yozzo K., Casey W., Allen D. (2020). "Validation of the OptiSafe™ eye irritation test". Cutan Ocul Toxicol. 39(3): 180-192. doi: 10.1080/15569527.2020.1787431

Clark D E. (2001). "Peroxides and peroxide-forming compounds". Chem. Health Saf. 8(5): 12-22. doi: 10.1021/acs.chas.8b08507.

Conrady C D., Joos Z P., Patel B C. (2016). "Review: The Lacrimal Gland and Its Role in Dry Eye". Journal of ophthalmology. 7542929. doi: 10.1155/2016/7542929 de Berardinis E., Tieri O., Polzella A., luglio N. (1965). "The chemical composition of the human aqueous humour in normal and pathological conditions". Experimental Eye Research. 4(3): 179-186. doi: 10.1016/S0014-4835(65) 80030-6.

Di Tommaso S., Rotureau P., Crescenzi O., Adamo C. (2011). "Oxidation mechanism of diethyl ether: a complex process for a simple molecule". Physical Chemistry Chemical Physics. 13:14636-14645. doi: 10.1039/C1CP21357A.

Draize J H., Woodard G., Calvery H O. (1944). "Methods for the study of irritation and toxicity of substances applied topically to the skin and mucous membranes". J. Pharmacol. And Exp. Therapeutics. 82:377-390.

Dwarakanath V., Pope G A. (1998). "New Approach for Estimating Alcohol Partition Coefficients between Nonaqueous Phase Liquids and Water". Environ. Sci. Technol. 32(11): 1662-1666. doi: 10.1021/es9707441

EC. (2001). Commission Directive 2001/59/EC of 6 Aug. 2001 adapting to technical progress for the 28th time Council Directive 67/548/EEC on the approximation of the laws, regulations and administrative provisions relating to the classification, packaging and labelling of dangerous substances. Official Journal of the European Communities L225, 1-333.

EC. (2008a). Classification, Regulation and Packaging (CLP): Regulation (EC) No. 1272/2008. Available: [http://echa.europa.eu/web/guest/regulations/clp].

EC. (2008b). Regulation (EC) No 1272/2008 of the European Parliament and of the Council of 16 Dec. 2008 on Classification, Labelling and Packaging of substances and mixtures, amending and repealing Directives 67/548/EEC and 1999/45/EC, and amending Regulation (EC) No 1907/2006. Official Journal of the European Union L353, 1-1355.

Faraguna F., Siuc V., Vidović E., Jukic A. (2015). "Reactivity ratios and properties of copolymers of 2-ethoxyethyl methacrylate with dodecyl methacrylate or styrene". J Polym Res. 22(245). doi: 10.1007/s10965-015-0890-4.

Fisher W B., VanPeppen J F. (2000). "Cyclohexanol and Cyclohexanone". Kirk-Othmer Encyclopedia of Chemical Technology. doi: 10.1002/0471238961.0325031206091908.a01

Frater R. (2009). "Neutralization of Acid in Glycol Methacrylate and the Use of Cyclohexanol as a Plasticizer". Stain Technology. 56(2): 99-101. doi: 10.3109/10520298109067290.

Garcia F., Garcia J M., Rubio F., de la Pena J L., Guzman J., Riande E. (2002). "Reaction kinetics and gel effect on the polymerization of 2-ethoxyethyl methacrylate and 2(2-ethoxyethoxy) ethyl methacrylate". Journal of Polymer Science Part A: Polymer Chemistry. 40(22). doi: 10.1002/pola.10480

Gierke J S., Sanders D L., Perram D L. (1999). "Laboratory Studies of Aqueous Partitioning Tracer Tests for Measuring Nonaqueous Phase Liquid Volumes". Water Environment Research. 71(4). doi: 10.2175/106143097X122202.

Grobe G M., Reichl S. (2013). "Characterization of vitamin C-induced cell sheets formed from primary and immortalized human corneal stromal cells for tissue engineering applications". Cells Tissues Organs. 197 (4): 283-97. doi: 10.1159/000346172.

Gulcin İ. (2020). "Antioxidants and antioxidant methods: an updated overview". Arch Toxicol. 94(3): 651-715. doi: 10.1007/s00204-020-02689-3.

Han Z., Zhang Z., Guan Y., Chen B., Yu M., Zhang L., Fang J., Gao Y., Guo Z. (2021). "New insights into Vitamin C function: Vitamin C induces JAK2 activation through its receptor-like transporter SVCT2". Int J Biol Macromol. 15; 173:379-398. doi: 10.1016/j.ijbiomac.2021.01.120.

H.R.4148. (2014). Humane Cosmetics Act 113th Congress (2013-2014). Rep. Moran, James P. [D-VA-8] (Introduced Mar. 5, 2014). beta.congress.gov/bill/113th-congress/house-bill/4148/

Huber M L., Laesecke A., Perkins R. (2004). "Transport Properties of n-Dodecane". Energy Fuels. 18(4): 968-975. doi: 10.1021/ef034109e.

Humane Society. (2017). Timeline: Cosmetics Testing on Animals: The Humane Society of the United States. [online] Available at: http://www.humanesociety.org/issues/cosmetic_testing/timelines/timeline-cosmetics-testing-on-animals.html [Accessed 27 Dec. 2017].

ICCVAM. (2009). Independent Scientific Peer Review Panel Report: Evaluation of the Validation Status of Alternative Ocular Safety Testing Methods and Approaches. Available at: iccvam.niehs.nih.gov/docs/ocutox_docs/OcularPRPRept2009.pdf ICCVAM. (2010). "ICCVAM-Recommended Test Method Protocol: Hen's Egg Test—Chorioallantoic Membrane (HET-CAM) Test Method". Available at: ntp.niehs.nih.gov/iccvam/docs/protocols/ivocular-het-cam.pdf ICCVAM-NICEATM. (2013). "Short Time Exposure (STE) Test Method Summary Review Document", National Toxicology Program. Available at: www.ntp.niehs.nih.gov/iccvam/docs/ocutox_docs/STE-SRD-NICEATM-508.pdf.

Jomova K., Valko M. (2011). "Advances in metal-induced oxidative stress and human disease". Toxicology. 283 (2-3): 65-87. doi: 10.1016/j.tox.2011.03.001.

Kanter J. (2017). E.U. Bans Cosmetics With Animal-Tested Ingredients. [online] Nytimes.com. Available at: http://www.nytimes.com/2013/03/11/business/global/eu-to-ban-cosmetics-with-animal-tested-ingredients.html [Accessed 31 Dec. 2017].

Kay J H., Calandra J C. (1962). "Interpretation of eye irritation tests". J. Soc. Cosmet. Chem. 13:281-289.

Kim Y H., Graham A D., Li W., Radke C J., Lin M C. (2019). "Human lacrimal production rate and wetted length of modified Schirmer's tear test strips". Trans Vis Sci Tech. 8(3): 40.

Kovacs E., Wolkober Z. (1973). "Effectivity of organic phosphites". Journal of Polymer Science: Polymer Symposia. 40(1): 73-78. doi: 10.1002/polc.5070400110.

Lebrun S., Choksi N., Daniel A., Allen D., Casey W. (2019). "Prevalidation of the OptiSafe Ocular Irritation Assay for the Detection of Ocular Corrosives". SOT 2020 Annual Meeting.

Lebrun S., Nguyen L., Chavez S., Chan R., Le D., Nguyen M., Jester J V. (2020). "Same-chemical comparison of nonanimal eye irritation test methods: Bovine corneal permeability, EpiOcular™, isolated chicken eye, ocular Irritection®, OptiSafe™, and short time exposure". Toxicol In Vitro. 2020:105070. doi: 10.1016/j.tiv.2020.105070.

Levene C I., Bates C J. (1975). "Ascorbic acid and collagen synthesis in cultured fibroblasts". Ann N Y Acad Sci. 258:288-306. doi: 10.1111/j.1749-6632.1975.tb29289.x.

Liu R., Mabury S A. (2019). "Organophosphite Antioxidants in Indoor Dust Represent an Indirect Source of Organophosphate Esters". Environ Sci Technol. 53(4): 1805-1811. doi: 10.1021/acs.est.8b05545.

MatTek Corporation. (2021). Protocol: "EpiOcular™ Eye Irritation Test (OCL-200-EIT) For the prediction of acute ocular irritation of chemicals: Identification of chemicals not requiring classification and labeling for eye irritation or serious eye damage". Available at: www.mattek.com/wp-content/uploads/OCL-200-EIT-Eye-Irritation-Test-Protocol-MK-24-007-0055_02_02_2021.pdf Medscape. (2017). "Vitamin C (Ascorbic Acid)". Available at: emedicine.medscape.com/article/2088649-overview Mikulás K., Hermann P., Gera I., Komlódi T., Horváth G., Ambrus A., Tretter L. (2018). "Triethylene glycol dimethacrylate impairs bioenergetic functions and induces oxidative stress in mitochondria via inhibiting respiratory Complex I". Dent Mater. 34(7): e166-e181. doi: 10.1016/j.dental.2018.03.012

Mottley C., Robinson R E., Mason R P. (1991). "Free radical formation in the oxidation of malondialdehyde and acetylacetone by peroxidase enzymes". Archives of Biochemistry and Biophysics. 289(1): 153-160. doi: 10.1016/0003-9861(91) 90455-R.

Nakchat O., Nalinratana N., Meksuriyen D., Pongsamart S. (2014). "Tamarind seed coat extract restores reactive oxygen species through attenuation of glutathione level and antioxidant enzyme expression in human skin fibroblasts in response to oxidative stress". Asian Pac J Trop Biomed. 4(5): 379-385. doi: 10.12980/APJTB.4.2014C806.

Niaz K., Mabqool F., Khan F., Hassan F I., Baeeri M., Navaei-Nigjeh M., Hassani S., Gholami M., Abdollahi M. (2017). "Molecular mechanisms of action of styrene toxicity in blood plasma and liver". Environmental Toxicology. 32:2256-2266. doi: 10.1002/tox.22441

Nita M., Grzybowski A. (2016). "The Role of the Reactive Oxygen Species and Oxidative Stress in the Pathomechanism of the Age-Related Ocular Diseases and Other Pathologies of the Anterior and Posterior Eye Segments in Adults". Oxid Med Cell Longev. 2016: 3164734. doi: 10.1155/2016/3164734

Njie-Mbye Y F., Kulkarni-Chitnis M., Opere C A., Barrett A., Ohia S E. (2013). "Lipid peroxidation: pathophysiological and pharmacological implications in the eye". Front Physiol. 4:366. doi: 10.3389/fphys.2013.00366.

OECD. (2018). "Test No. 438: Isolated Chicken Eye Test Method for Identifying i) Chemicals Inducing Serious Eye Damage and ii) Chemicals Not Requiring Classification for Eye Irritation or Serious Eye Damage". OECD Guidelines for the Testing of Chemicals, Section 4, OECD Publishing, Paris, doi.org/10.1787/9789264203860-en.

OECD. (2019a). "Test No. 492: Reconstructed human Cornea-like Epithelium (RhCE) test method for identifying chemicals not requiring classification and labelling for eye irritation or serious eye damage". OECD Guidelines for the Testing of Chemicals, Section 4, OECD Publishing, Paris, doi.org/10.1787/9789264242548-en.

OECD. (2019b). "Test No. 496: in vitro Macromolecular Test Method for Identifying Chemicals Inducing Serious Eye Damage and Chemicals not Requiring Classification for Eye Irritation or Serious Eye Damage. OECD Guidelines for the Testing of Chemicals, Section 4, OECD Publishing, Paris, doi.org/10.1787/970e5cd9-en OECD. (2020a). "Test No. 437: Bovine Corneal Opacity and Permeability Test Method for Identifying i) Chemicals Inducing Serious Eye Damage and ii) Chemicals Not Requiring Classification for Eye Irritation or Serious Eye Damage". OECD Guidelines for the Testing of Chemicals, Section 4, OECD Publishing, Paris, doi.org/10.1787/9789264203846-en OECD. (2020b). "Test No. 491: Short Time Exposure In Vitro Test Method for Identifying i) Chemicals Inducing Serious Eye Damage and ii) Chemicals Not Requiring Classification for Eye Irritation or Serious Eye Damage". OECD Guidelines for the Testing of Chemicals, Section 4, OECD Publishing, Paris, doi.org/10.1787/9789264242432-en.

Palmlof M., Hjertbeg T. (2000). "Chemical and mechanical changes in poly(ethylene-co-1,9-decadiene) following crosslinking induced by peroxides". Polymer. 41(17): 6497-6505. doi: 10.1016/S0032-3861(99)00881-2.

Paterson C A., O'Rourke M. (1987). "Vitamin C Levels in Human Tears". Arch Opthalmol. 105(3): 376-377. doi: 10.1001/archopht. 1987.01060030096034.

Peterkofsky B. (1972). "The effect of ascorbic acid on collagen polypeptide synthesis and proline hydroxylation during the growth of cultured fibroblasts". Arch Biochem Biophys. 152(1): 318-28. doi: 10.1016/0003-9861(72) 90221-4.

Rodrigues A P., da Fonseca L M., de Faria Oliveira O M., Brunetti I L., Ximenes V F. (2006). "Oxidation of acetylacetone catalyzed by horseradish peroxidase in the absence of hydrogen peroxide". Biochim Biophys Acta. 1760(12): 1755-61. doi: 10.1016/j.bbagen.2006.09.008.

S.697. (2016). Frank R. Lautenberg Chemical Safety for the 21st Century Act. 114th Congress (2015-2016) www.congress.gov/bill/114th-congress/senate-bill/697.

Schwetlick K., Pionteck T J., Habicher W D. (1987). "Organophosphorus antioxidants—VIII. Kinetics and mechanism of the reaction of organic phosphites with peroxy radicals". European Polymer Journal. 23(5): 383-388. doi: 10.1016/0014-3057(87) 90167-4.

Schwetlick K., Habicher W D. (1995). "Organophosphorus antioxidants action mechanisms and new trends". Die Angewandte Makromolekular Chemie. 232(1): 239-246. doi: 10.1002/apmc.1995.052320115.

Senate Joint Resolution 22. (2014). Introduced by Senator Block. Mar. 24, 2014. leginfo.legislature.ca.gov/faces/billNavClient.xhtml?bill_id=201320140SJR22&search_key words=

Smedberg A., Hjertberg T., Gustafsson B. (1997). "Crosslinking reactions in an unsaturated low density polyethylene". Polymer. 38(16): 4127-4138. doi: 10.1016/S0032-3861(96) 00994-9.

Su L J., Zhang J H., Gomez H., Murugan R., Hong X., Xu D., Jiang F., Peng Z Y. (2019). "Reactive Oxygen Species-Induced Lipid Peroxidation in Apoptosis, Autophagy, and Ferroptosis". Oxid Med Cell Longev. 2019:5080843. doi: 10.1155/2019/5080843.

Suksomtip M., Ukrisdawithid S., Bhusawang P., Pongsamart S. (2010). "Phenolic compound content, antioxidant and radical-scavenging properties of methanolic extracts from the seed coat of certain thai tamarind culivars". Journal of Food Biochemistry. 34(5). doi: 10.1111/j.1745-4514.2009.00323.x.

Tei T., Sato Y., Hagiya K., Tai A., Okuyama T., Sugimura T. (2002). "'Chiral perturbation factor' approach reveals importance of entropy term in stereocontrol of the 2,4-pentanediol-tethered reaction". J Org Chem. 67(19): 6593-8. doi: 10.1021/jo025937s.

Tangvarasittichai O., Tangvarasittichai S. (2018). "Oxidative Stress, Ocular Disease and Diabetes Retinopa-

US 12,648,892 B2

27 thy". Curr Pharm Des. 24(40): 4726-4741. doi: 10.2174/1381612825666190115121531.

Umapathy A., Donaldson P., Lim J. (2013). "Antioxidant Delivery Pathways in the Anterior Eye". Biomed Research International, 10 pages. doi: 10.1155/2013/207250.

UN (2011). United Nations Globally Harmonized System of Classification and Labelling of Chemicals (GHS), ST/SG/AC.10/30 Rev 4, Part 3 Health Hazards—Chapter 3.3 Serious eye damage/eye irritation. New York & Geneva: United Nations Publications. pp. 133-144. Available: [http://www.unece.org/trans/danger/publi/ghs/ghs_rev04/04files_e.html].

Ung L., Pattamatta U., Carnt N., Wilkinson-Berka J L., Liew G., White A J R. (2017). "Oxidative stress and reactive oxygen species: a review of their role in ocular disease". Clin Sci. 131(24): 2865-2883. doi: 10.1042/CS20171246.

US EPA (1998). Health Effects Test Guideline, OPPTS 870.2400 Acute Eye Irritation. EPA 712-C-98-195. US Environmental Protection Agency, Washington, DC, USA.

US EPA (2003). Label Review Manual. 3rd Edition. EPA 735-B-03-001. US Environmental Protection Agency, Washington, DC, USA.

Wang K., Hawley M C., Furney T D. (2003). "A selectivity study of 2,4-pentanediol hydrogenolysis combining experiments and computer simulation". Chemical Engineering Science. 58(18): 4271-4285. doi: 10.1016/S0009-2509(03) 00285-9.

Wilson S L., Ahearne M., Hopkinson A. (2015). "An overview of current techniques for ocular toxicity testing". Toxicology. 327:32-46.

Winterbourn C C. (1995). "Toxicity of iron and hydrogen peroxide: the Fenton reaction". Toxicol Lett. 82-83: 969-74. doi: 10.1016/0378-4274(95) 03532-x.

Zhang L., Zhang Z., He X., Zhang F., Zhang Z. (2017). "Regulation of the products of styrene oxidation". Chemical Engineering Research and Design. 120:171-178. doi: 10.1016/j.cherd.2017.02.012.

Zhu T., Lim B S., Park H C., Son K M., Yang H C. (2012). "Effects of the iron-chelating agent deferoxamine on triethylene glycol dimethacrylate, 2-hydroxyethyl methacrylate, hydrogen peroxide-induced cytotoxicity". J Biomed Mater Res B Appl Biomater. 100(1): 197-205. doi: 10.1002/jbm.b.31939

Section #2

Abbreviations: AA: ascorbic acid, CASRN: Chemical Abstracts Service registry number, DNA: deoxyribonucleic acid, DoD: depth of damage, EDTA: ethylenediaminetetraacetic acid, EIT: Eye Irritation Test, EWB: eye wash buffer, FDA: U.S. Food and Drug Administration, FP: false positive, IVD: in vitro depth of damage, NaCl: sodium chloride, NaOCl: sodium hypochlorite, NaOH: sodium hydroxide, OM: ocular medium, OS: OptiSafe EIT, ROS: reactive oxygen species, SE: standard error, SM: sulfur mustard, TED: topical eye drop, TGF: transforming growth factor, TRAM-34: triarylmethane-34, TUNEL: terminal deoxynucleotidyl transferase dUTP nick-end labeling 1. Introduction Chemical eye injuries account for up to 22% of clinically reported ocular trauma cases (Kuckelkorn, 2002; Clare, 2012; Dua et al., 2020). Chemicals that cause eye injury include alkalis, acids, and strongly oxidative chemicals that form reactive oxygen species (ROS) (Bunker et al., 2014; Ung et al., 2017; Dua et al., 2020).

While numerous hazardous chemicals can form ROS and injure the eye (Banin et al., 2003; Corrales et al., 2017; Ung et al., 2017), what may be less widely recognized is that a number of chemicals associated with oxidation and ROS do not injure the eye in vivo (Lebrun et al., 2021a, 2022). During the development of the OptiSafe™ eye irritation test (OS EIT), an in chemico eye safety test used to classify ocular irritants (Lebrun et al., 2021a, 2023a, 2023b), we found that a high percentage of OS EIT false-positive (FP) results were associated with chemicals identified by database searches as oxidizers that generate ROS (Lebrun et al., 2021a, 2022). Based on these findings, we hypothesized that the addition of tear antioxidants to nonanimal eye safety tests might lower the FP rate (Lebrun et al., 2021b, 2021c, 2021d, 2021e; Lebrun and Nguyen, 2022). To test this hypothesis, tear-related antioxidants were systematically titrated, and their effects on chemicals associated with such FP results were assessed (Lebrun et al., 2021a). A screen of the five most abundant antioxidants found in human and rabbit tears was performed. Antioxidants were added directly to the OS EIT test matrix. The tear antioxidants evaluated included tyrosine, uric acid, ascorbic acid (AA), cysteine, and glutathione (Lebrun et al., 2021a). Based on this evaluation, we found that AA results in a specific reduction of the FP rate with no change in the false-negative rate (Lebrun et al., 2022, 2023a, 2023b). This effect of AA was pronounced at the approximate mean human physiological tear concentration of 0.1 mg/mL (0.01%) (Chen et al., 2009; Lebrun et al., 2021a, 2022), supporting the hypothesis that AA in tears reduces corneal damage by inactivating chemicals that cause ROS generation before they have a chance to damage the eye (Lebrun et al., 2021a, 2022).

We hypothesized that the addition of AA at higher-than-tear concentrations to a wash solution might reduce eye damage caused by strong chemical oxidants; testing this hypothesis is detailed below.

In vivo AA is found in mammalian tears (Chen et al., 2009) and the aqueous humor (Chen et al., 2009; Reiss et al., 1986). Levels of AA in the aqueous humor are about 15 times higher than those in plasma (Dua et al., 2020); levels in "basal" tears are similar to those in the aqueous humor, in the range of 220 µM to 1,310 µM. Reflex tears induced by ammonia inhalation exposure can result in decreased AA concentrations to about 110 µM (Paterson and O'Rourke, 1987).

There are a limited number of studies on the effects of AA following eye injury. In the 1970s, Pfister et al. (1977, 1978, 1980) identified a reduction in aqueous humor AA concentrations following severe alkali burns in rabbits (35-second eye exposure to 1 N NaOH). They hypothesized that restoring aqueous humor levels of AA would reduce this damage. Their study compared the subcutaneous injection of a 15% AA solution (within 3 h of the burn) once daily compared with a topical 10% AA eye drop (hydroxyethyl cellulose with polyvinylpyrrolidone, thimerosal, and EDTA) adjusted to pH 7.2 and administered 2 h after the burn and at hourly intervals for 14 h per day. They found that the eye drops reduced corneal ulceration, but subcutaneous injections were ineffective (Levinson et al., 1976; Pfister and Paterson, 1977; Pfister et al., 1978, 1980). Pfister et al. (1977, 1978, 1980) proposed that the observed AA-related reduction in corneal ulceration was based on its involvement in proline and lysine hydroxylation and fibroblast collagen extrusion (Levinson et al., 1976; Lee and Chung, 2012). However, in some studies, AA did not seem to have much effect on epithelial migration/wound closure (Levinson et al., 1976).

A more current study tested a topical eye drop (TED) formulation of FDA-approved drugs [25 μM suberoylanilide hydroxamic acid (Vorinostat), 25 μM enalapril, 0.5% ketoro-lac] in combination with 10% vitamin C on rabbit eyes after exposure to the alkylating agent sulfur mustard (SM) (Trip-athi et al., 2020). Two drops of the TED solution were applied to the eye, twice per day, starting 2 h after SM exposure. The authors concluded that the TED treatment after SM exposure improved clinical symptoms by reducing corneal edema, central corneal thickness, corneal haze, and inflammatory and profibrotic marker levels, including trans-forming growth factor (TGF)-β1 and cyclooxygenase-2 (Tripathi et al., 2020).

In another recent study, corneal fibrosis was induced by alkali injury with 0.5 N sodium hydroxide solution (Fuchs et al., 2022; Gupta et al., 2018). A topical eye drop solution formulated with 10% AA combined with TRAM-34, a selective inhibitor of intermediate-conductance calmodulin/ calcium-activated K+ channels, was shown to reduce mark-ers of corneal fibrosis/haze and downregulate various fibrotic markers associated with TGF-β1-mediated fibrosis (Fuchs et al., 2022; Mohan et al., 2022).

These prior studies all used drops containing 10% AA starting 2 h after sodium hydroxide or SM injury. In contrast, the study described here uses a high-volume (100-500 mL) of buffered wash solution, which differs from the recom-mended postexposure wash procedure.

The most commonly suggested treatment immediately after chemical exposure of the eye is washing with tap water for 15 min (Hall and Maibach, 2006; Rihawi et al., 2007). Additional reported washing strategies include keeping the eye open for as long as possible while looking in different directions (up, down, left, right) to allow the water to reach all parts of the eye (OSHA, 2009). Others suggest washing the eye with normal saline, Ringer's lactate solution or saline with sodium bicarbonate, with volumes up to 20 L (Herr et al., 1991; Chau et al., 2012).

The purpose of the current study is to test the inventor's hypothesis that eye washing with a buffered AA solution after strong oxidizer exposure [sodium hypochlorite (NaOCl): "chlorine bleach"] reduces death of the corneal stroma. To evaluate and explore this hypothesis, different conditions were studied, including duration of washing, and a comparison of active washing with tap water, buffer alone, or buffer with 0.2% AA.

2. Methods 2.1 Eyes

Whole New Zealand White rabbit eyes were used Prior to exposure a 10-mm internal dosing ring (FIG. 12A, part of the IVD kit) was placed over the central cornea that was then exposed to NaOCl.

2.2 NaOCl Exposure and Rinsing

Prior to each experiment (<1 h), NaOCl (CASRN 7681-52-9, Sigma-Aldrich, St. Louis, MO) was freshly diluted in sterile deionized water, mixed by five tube inversions prior to each application, and applied directly to the eyes (cor-neas) by transferring 100 μL with a micropipette into the dosing ring (FIG. 12A); the corneas were then exposed to this solution for exactly 1 min. Immediately after exposure, corneas were rinsed for exactly 30 s by forcefully dispensing 20 mL saline (9 g/L NaCl) from an eye rinsing syringe (part of the IVD kit). The pH of the 32% NaOCl was measured using a Fisherbrand™ Accumet™ AB150 pH benchtop meter (Fisher Scientific, Waltham, MA).

2.3 Washing

A 100-ml beaker or 500-mL emergency eye wash bottle (FIG. 12B) was used to prepare the AA solution and wash the eyes (Lebrun and Nguyen, 2024). These containers hold a ready-to-use eye wash buffer (EWB) solution composed of potassium chloride (CASRN 7447-40-7, 2.7 mM; Fisher Scientific), potassium phosphate monobasic (CASRN 7778-77-0, 1.5 mM; Fisher Scientific), sodium chloride (CASRN 7647-14-5, 137.9 mM; Fisher Scientific), sodium phosphate dibasic (CASRN 7782-85-6, 8.1 mM; Sigma Aldrich), deionized water (ReadyRefresh, Stamford, CT), 1% dextran (CASRN 9004-54-0; Sigma Aldrich), and 1% bovine serum albumin (CASRN 9048-46-8; Sigma Aldrich). Before use, different amounts of powdered AA (CASRN 50-81-7; Sigma Aldrich) are dispersed into the liquid component and rapidly mixed to achieve a predefined concentration (Lebrun et al., 2021c, 2021d, 2021e) to form complete EWB+AA. The two-part formulation procedure reduces AA oxidation and ensures consistent activity because AA stored as a dry powder was found to be considerably more stable than AA in solution (Lebrun and Nguyen, 2024). The pH of the liquid portion of the wash solution is adjusted to 7.2 with HCl to ensure that the final wash solution for the 0.2% powdered AA reaches a pH of 6.99±0.5. For the 10% AA condition, the pH was further adjusted to 6.99±0.5 with 1 N NaOH. For the EWB only condition, the pH was adjusted to 6.99±0.5 with 1 N HCl. For the wash step, eyes were either passively soaked in beakers (100-mL conditions) or washed with an eyewash bottle (500-mL conditions) for the indicated times. The eyewash bottle allows for forceful spraying and recy-cling of the 500-mL solution (Lebrun and Nguyen, 2024). While this bottle can be used in vivo or in vitro, for the in vitro study described here, the eyes were placed cornea-side down in the well at the top of the bottle, and the bottles were compressed so that a jet of solution washed over the eye (see FIG. 12B).

2.4 NaOCl Titration Study

Corneas were exposed to 100 μL of 0, 8%, 16%, or 32% NaOCl for 1 min. After exposure, corneas were rinsed with 20 mL saline, and eyes were further washed by placing in a beaker containing 100 mL EWB for 30 min without agita-tion. After "washing," eyes were processed following the "postexposure" steps described below. The pH of 32% NaOCl was 12.04.

2.5 Wash Duration Study

The corneas of whole eyes were exposed to 100 μL of 32% NaOCl within a dosing ring for 1 min, rinsed with 20 mL saline, and washed without agitation in beakers for 1, 15, or 30 min with either 100 mL EWB or EWB+0.2% AA. "Washed" eyes were processed following the "postexpo-sure" steps described below.

2.6 Repeat and 10% AA Study

The corneas of whole eyes were exposed to 100 μL of 32% NaOCl within a dosing ring for 1 min, rinsed, and washed for 15 min. Washing was with EWB, EWB+0.2% AA, or EWB+10% AA. After "washing," eyes were pro-cessed following the "postexposure" steps described below.

2.7 Wash Bottle Study

Figures 12A, 12B:
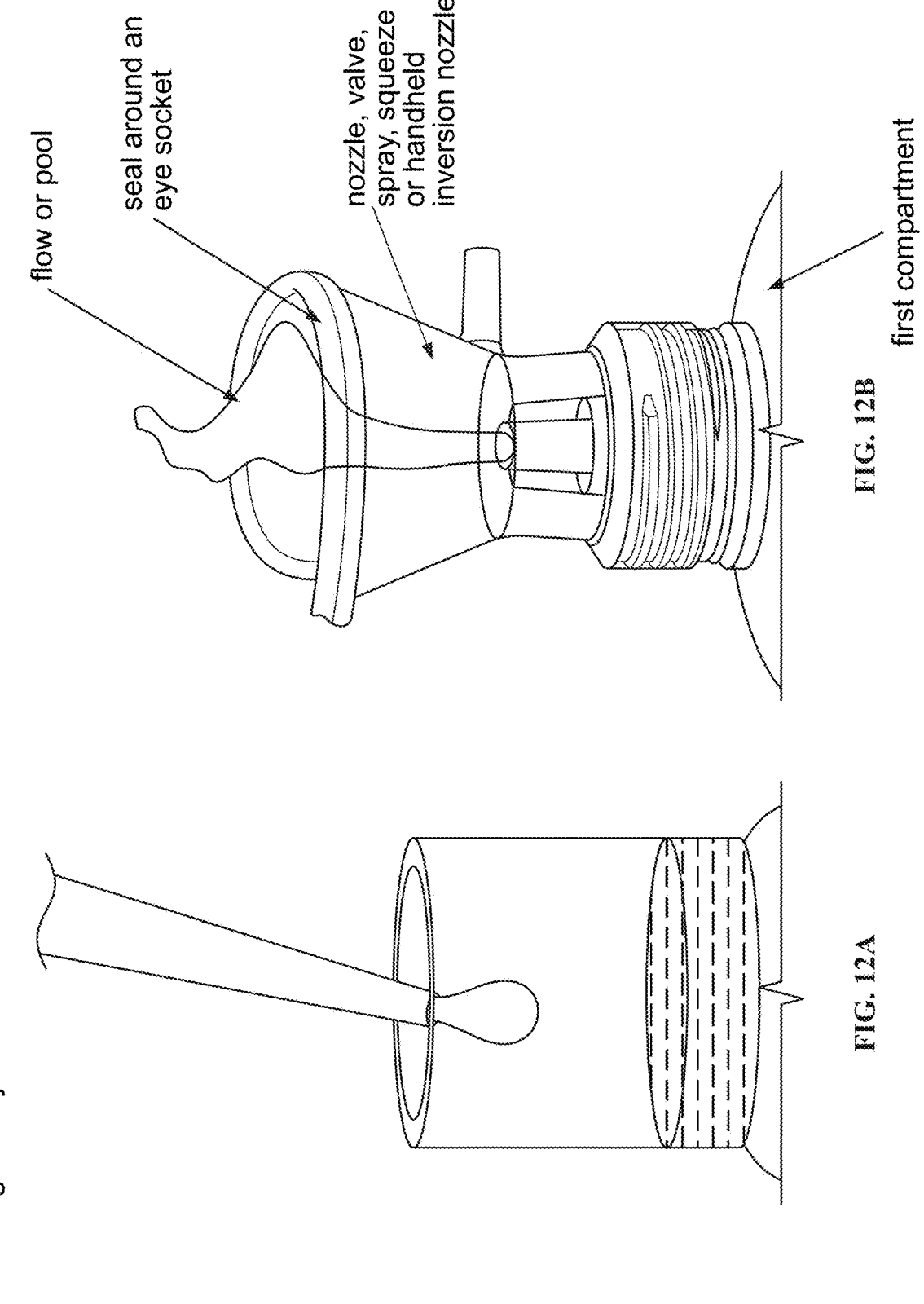
FIGS. 12A-12B: 12A shows the dosing ring and an eye being dosed with 100 μL of test material. 12B shows the 500-mL EWB. The 500-ml bottle has a cap that allows a spray of wash solution to be forced onto the cornea when the bottle is squeezed (eye not shown in 12B so that fluid jet can be observed).

The corneas of whole eyes were exposed to either 100 μL of 32% NaOCl for 1 min or 100 μL deionized sterile water for 1 min (control condition) in a dosing ring. Eyes were then rinsed, and all eyes were washed using 500-mL wash bottles (FIG. 12B). Washing was with sterile tap water (municipal water, Anaheim, CA, 0.22-micron pore size filtered), EWB, or EWB+0.2% AA. After "washing," eyes were processed following the "postexposure" steps described below.

2.7 Postexposure

After washing, eyes were placed in fresh postexposure wells (part of the IVD kit) containing approximately 1.5 mL OM added to the level of the limbus. Eyes were then placed back into a humidified, 5% $CO_2$, 37° C. incubator for 24 h. Corneas were then removed by dissection, placed in 4% paraformaldehyde in phosphate-buffered saline (fixative; Boston BioProducts, Inc., Milford, MA), and stored at 4° C.

2.8 Tissue Processing

After a minimum of 24 h in fixative, corneas were cut in half and infiltrated with 30% sucrose (Capella et al., 1965), and the tissues were then embedded in Tissue-Tek® O.C.T. compound (Sakura Finetek, Torrance, CA), snap frozen in liquid nitrogen, and stored in an ultralow freezer (−80° C., New Brunswick Scientific, Hamburg, Germany). Using a cryostat (Leica CM 1900 UV, Leica Biosystems, Deer Park, USA), nine 8-μm-thick tissue sections were collected at 100-μm intervals and placed onto glass slides (Superfrost Plus Microscope Slides White Tab, Fisher Scientific, Pittsburgh, PA), alternating between slides so that the greatest depth of sampling was achieved (three sections/slide).

Three sections per eye were then stained for apoptosis- and necrosis-related DNA fragmentation (Stadelmann and Lassmann, 2000) with terminal deoxynucleotidyl transferase dUTP nick-end labeling (TUNEL) of the 3'-hydroxyl termini of double-stranded DNA breaks using a TUNEL labeling kit (part of the IVD kit). Prior to imaging, coverslips were applied to the slides using a mounting solution (part of the IVD kit).

2.9 Data Collection and Analysis

Stained sections were viewed using a Leica DMRE fluorescence microscope (Leica Microsystems Inc., Buffalo Grove, IL). Images were collected using a low-light-level camera (Kiralux 2.3 MP Monochrome CMOS Camera, Thorlabs, Newton, NJ) and Leica 5×/0.15 HC PL Fluotar objective (Leica Microsystems Inc., Buffalo Grove, IL). An L5 Fluorescence Filter Cube (Leica Microsystems Inc., Buffalo Grove, IL) was used for TUNEL and DoD imaging. Images were processed and analyzed using ImageJ software, version 1.54 (Schneider et al., 2012). TUNEL positive nuclei are represented in white. Three corneal cryosections, each approximately 2.3 mm long and 0.5-0.9 mm wide (depending on swelling), were measured for each eye. To count TUNEL-positive nuclei, the number of discrete TUNEL-positive nuclei in the stroma that meet the size parameters associated with a keratocyte nucleus were recorded for each section using ImageJ software. Each TUNEL-positive nucleus counted is assumed to be from one dead cell. The term "fragmented DNA" is used interchangeably with the term "TUNEL-positive nucleus." For depth of damage (DoD) calculations, the thickness of the entire stroma from the end of the corneal epithelium (Epithelium) to the beginning of the corneal endothelium (Endothelium) was measured. The percentage of stromal death was determined by calculating the depth of the TUNEL-positive stroma divided by the total stromal thickness. The average number of dead cells and average stromal DoD were then calculated for each section, and the averages of three sections were recorded for each eye. All reported TUNEL-positive counts and DoD measurements are for a standardized 2.3 mm long×0.5-0.9 mm thick (thickness depends on swelling, noting that corneal swelling occurs after some toxin exposure) section.

3.0 Database Search to Estimate the Percentage of Ocular Corrosive Chemicals that are Acids, Bases, or Associated with ROS Chemicals We compiled a list of 108 chemicals that cause extreme/irreversible damage to the eye in vivo from existing publicly available sources for chemicals that have corresponding CASRN and GHS classifications (Supplementary Table 1). We then determined which of these were associated with ROS or were strong acids (pH 5 or less) or bases (pH 9 or greater).

Extreme/Irreversible Damage to the Eye Association with ROS Chemistry Search Criteria A standardized search procedure was used to identify chemicals associated with strong oxidation and ROS: The NIH PubMed database, Multidisciplinary Digital Publishing Institute (MDPI), Chemistry Europe, and Egyptian Journal of Agricultural Research (EJAR) were used as peer-reviewed and trusted sources. The NIH PubMed database (NIH, 2024) and the OECD website (OECD, 2024) were used to search for publications and documentation. The following keywords were used for each test chemical: "chemical name, CASRN, reactive oxygen species, ROS." Each result was individually read and evaluated by a qualified chemist to make sure the methods used were appropriate and met criteria for ROS. Studies were required to explicitly state the association between the chemical and ROS and prove the direct or indirect cause of ROS with experimental data. The first 100 results from each of the search criteria above were analyzed.

Extreme/irreversible damage to the eye association with pH search criteria A standardized search procedure was used to identify the pH for chemicals that were not found to be associated with strong oxidation or ROS (ROS chemicals were not used for the pH analysis to avoid overinflating the prediction with duplicates for chemicals positive for both). The pH values reported reflect the most extreme pH value found for each chemical. The NIH PubMed/PubChem database and Millipore Sigma, Fisher Scientific were used as sources. The following keywords were used for each test chemical: "chemical name, CASRN, pH." Chemicals with pH values less than or equal to 5 or greater than or equal to 9 were identified as biologically significant acids or bases, respectively.

2.10 Statistics

Data were statistically analyzed using Microsoft Excel™ software. Differences between groups were assessed for significance with analysis of variance, and P values are shown for each comparison to indicate significant differences between the treatment and control groups. P values were reported as P<0.001 when the test group and the control group were significantly different. Throughout the text, numbers are represented as averages±SE.

As shown in Supplementary Table 2, the percentage of ROS-associated chemicals is calculated by dividing the ROS-associated chemicals by the total number chemicals identified that cause extreme/irreversible damage to the eye in vivo. The pH values are then searched for the remaining non-ROS-associated chemicals. A statistical sample is taken for the chemicals with identified pH values and applied (multiplied by) to the entire non-ROS-associated population (to normalize for chemicals with unknown pH values); this value was converted to a percentage to estimate the rate of occurrence of ROS or acids/bases.

3. Results

Results for four experiments are presented: 1) NaOCl titration, 2) washing duration, 3) repeat and 10% AA, 4) 500-mL wash bottle study.

3.1 NaOCl Titration

Figure 13:
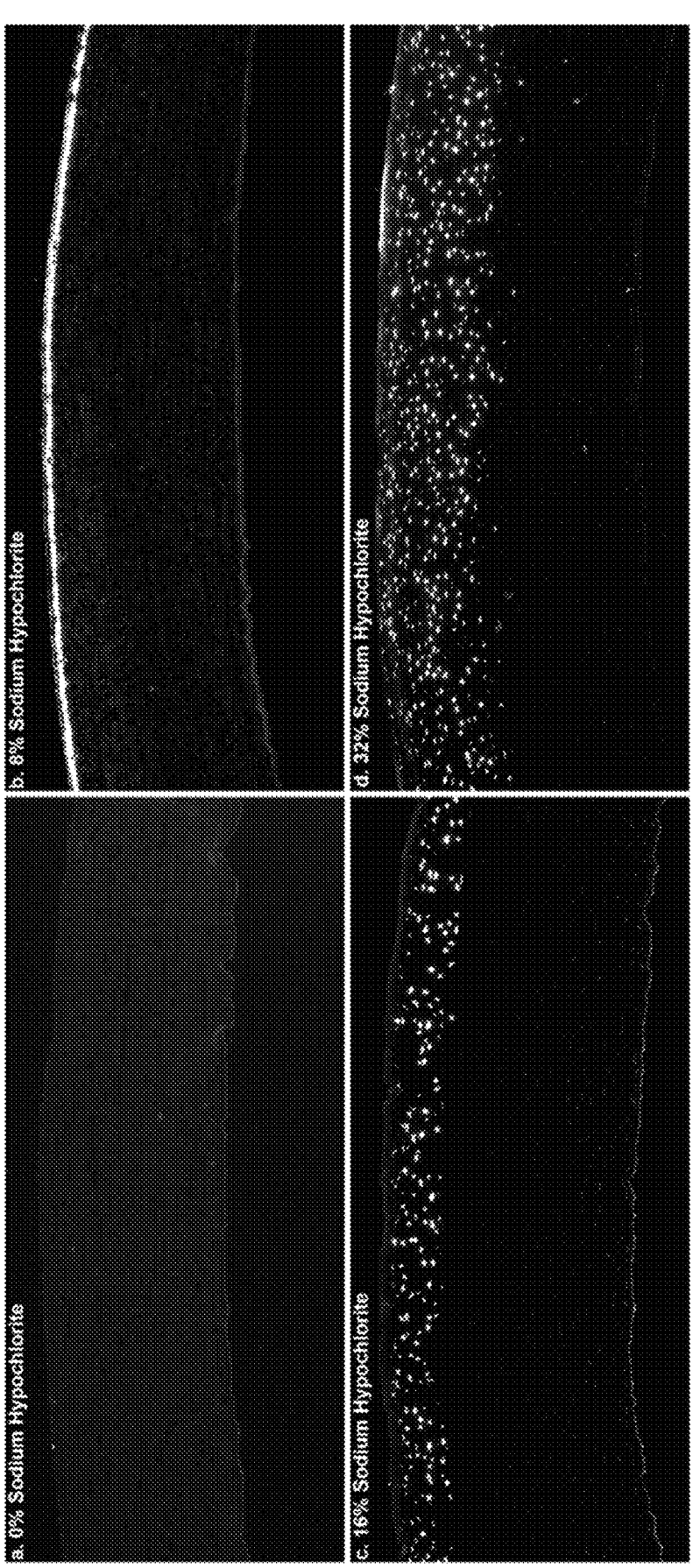
FIG. 13: DNA fragmentation pattern of the cornea 24 h after exposure to NaOCl. Corneas exposed to 100 μL of 0%, 8%, 16%, or 32% NaOCl for 1 min, then passively washed for 30 min by placing in a beaker with 100 mL of EWB and then incubated for 24 h. Corneas were removed, fixed, frozen, sectioned, and labeled for dead cell fragmented DNA by TUNEL staining (white). See Table 1 for quantification of triplicate sections.

FIG. 13 and Table 1 show a comparison of eyes exposed to 0 (a), 8% (b), 16% (c), or 32% (d) NaOCl. TUNEL nuclear staining (shown in white) is absent in 0% NaOCl but increases in the epithelium at 8% NaOCl. The specificity of epithelial cell staining with TUNEL does not appear to have a clear dose-response relationship. In particular, the TUNEL epithelial staining pattern is difficult to interpret because at higher toxin concentrations, more cell death, and hence more TUNEL staining, is expected but not observed. We conclude that with TUNEL staining, epithelial effects cannot be interpreted at 32% NaOCl using this approach.

TABLE 1

TUNEL Positive Nuclei Counts for Sodium Hypochlorite Titration

| Condition | E | Section | S. AVG ± SE | AVG ± SE |
|---|---|---|---|---|
| 0% NaOCl | 1 | A = 0.0; B = 0.0; C = 0.0 | 0.0 ± 0.0 | 0.0 ± 0.0 |
| | 2 | A = 0.0; B = 0.0; C = 0.0 | 0.0 ± 0.0 | |
| | 3 | A = 0.0; B = 0.0; C = 0.0 | 0.0 ± 0.0 | |
| 8% NaOCl | 1 | A = 0.0; B = 0.0; C = 0.0 | 0.0 ± 0.0 | 3.1 ± 3.1 |
| | 2 | A = 12.0; B = 13.0; C = 3.0 | 9.3 ± 3.2 | |
| | 3 | A = 0.0; B = 0.0; C = 0.0 | 0.0 ± 0.0 | |
| 16% NaOCl | 1 | A = 137.0; B = 164.0; C = 172.0 | 157.7 ± 10.6 | 139.9 ± 20.7 |
| | 2 | A = 104.0; B = 77.0; C = 115.0 | 98.7 ± 11.3 | |

TABLE 1-continued

TUNEL Positive Nuclei Counts for Sodium Hypochlorite Titration

| Condition | E | Section | S. AVG ± SE | AVG ± SE |
|---|---|---|---|---|
| | 3 | A = 126.0; B = 191.0; C = 173.0 | 163.3 ± 19.4 | |
| 32% NaOCl | 1 | A = 214.0; B = 236.0; C = 196.0 | 215.3 ± 11.6 | 193.7 ± 35.5 |
| | 2 | A = 85.0; B = 116.0; C = 172.0 | 124.3 ± 25.5 | |
| | 3 | A = 211.0; B = 246.0; C = 267.0 | 241.3 ± 16.3 | |

NaOCl = Sodium Hypochlorite;
R = Repeat;
E = Eye Number;
S. AVG ± SE = Section Average ± Standard Error;
AVG ± SE = Overall Average ± Standard Error On the other hand, the corneal stromal cell (keratocytes) nuclei show a dose-dependent increase in the number of TUNEL-positive nuclei (punctate white spots) at 16% and 32% NaOCl. The number of stromal TUNEL-positive nuclei increased from an average of 139.9±20.7 with 16% NaOCl to an average of 193.7±35.5 with 32% NaOCl. Table 1 shows the TUNEL positive nuclei counts for each section (A, B, or C) for each individual eye (1, 2, or 3), the section average±SE, and overall average±SE.

3.2 AA Washing Study

FIG. 14 and Table 2A-2B show the results for eyes exposed to 32% NaOCl followed by washing for 1, 15, or 30 minutes with EWB or with EWB+0.2% AA. Corneas washed with AA have fewer TUNEL-stained nuclei (shown in white) at each wash duration, although there was variability [see SE values for individual eye section results and average eye results (Table 2).

TABLE 2A

TUNEL Positive Nuclei Counts for Wash Study
A. Individual Sections and Eyes

| Wash Time | E | EWB Section | S. AVG ± SE | EWB ± 0.2% Ascorbic Acid Section | S. AVG ± SE |
|---|---|---|---|---|---|
| 1 Minute | 1 | A = 153.0; B = 188.0; C = 222.0 | 187.7 ± 19.9 | A = 131.0; B = 115.0; C = 109.0 | 118.3 ± 6.6 |
| | 2 | A = 246.0; B = 203.0; C = 160.0 | 203.0 ± 24.8 | A = 97.0; B = 139.0; C = 130.0 | 122.0 ± 12.8 |
| | 3 | A = 201.0; B = 137.0; C = 164.0 | 167.3 ± 18.6 | A = 118.0; B = 82.0; C = 103.0 | 101.0 ± 10.4 |
| 15 Minutes | 1 | A = 243.0; B = 255.0; C = 245.0 | 247.7 ± 3.7 | A = 101.0; B = 83.0; C = 86.0 | 90.0 ± 5.6 |
| | 2 | A = 203.0; B = 211.0; C = 224.0 | 212.7 ± 6.1 | A = 82.0; B = 58.0; C = 64.0 | 68.0 ± 7.2 |
| | 3 | A = 238.0; B = 245.0; C = 229.0 | 237.3 ± 4.6 | A = 99.0; B = 89.0; C = 78.0 | 88.7 ± 6.1 |
| 30 Minutes | 1 | A = 234.0; B = 275.0; C = 218.0 | 242.3 ± 17.0 | A = 137.0; B = 141.0; C = 149.0 | 142.3 ± 3.5 |
| | 2 | A = 316.0; B = 342.0; C = 278.0 | 312.0 ± 18.6 | A = 109.0; B = 71.0; C = 86.0 | 88.7 ± 11.1 |
| | 3 | A = 147.0; B = 105.0; C = 158.0 | 136.7 ± 16.1 | A = 56.0; B = 67.0; C = 44.0 | 55.7 ± 6.6 |

Table 2A shows the TUNEL Counts for each individual section.

E = Eye Number; EWB = Eye Wash Buffer; S. AVG ± SE = Section Average ± Standard Error.

TABLE 2B

TUNEL Positive Nuclei Counts for Wash Study
B. Average of 9 Sections (3 Eyes) Per Condition

| | AVG ± SE | |
|---|---|---|
| Wash Time | EWB | EWB + 0.2% AA |
| 1 Minute | 186.0 ± 10.3 | 113.8 ± 6.5 |
| 15 Minutes | 232.6 ± 10.4 | 82.2 ± 7.1 |
| 30 Minutes | 230.3 ± 51.0 | 95.6 ± 25.3 |

Table 2B shows the three-eye summary. E = Eye Number; EWB = Eye Wash Buffer; S. AVG ± SE = Section Average ± Standard Error.

Figure 14A:
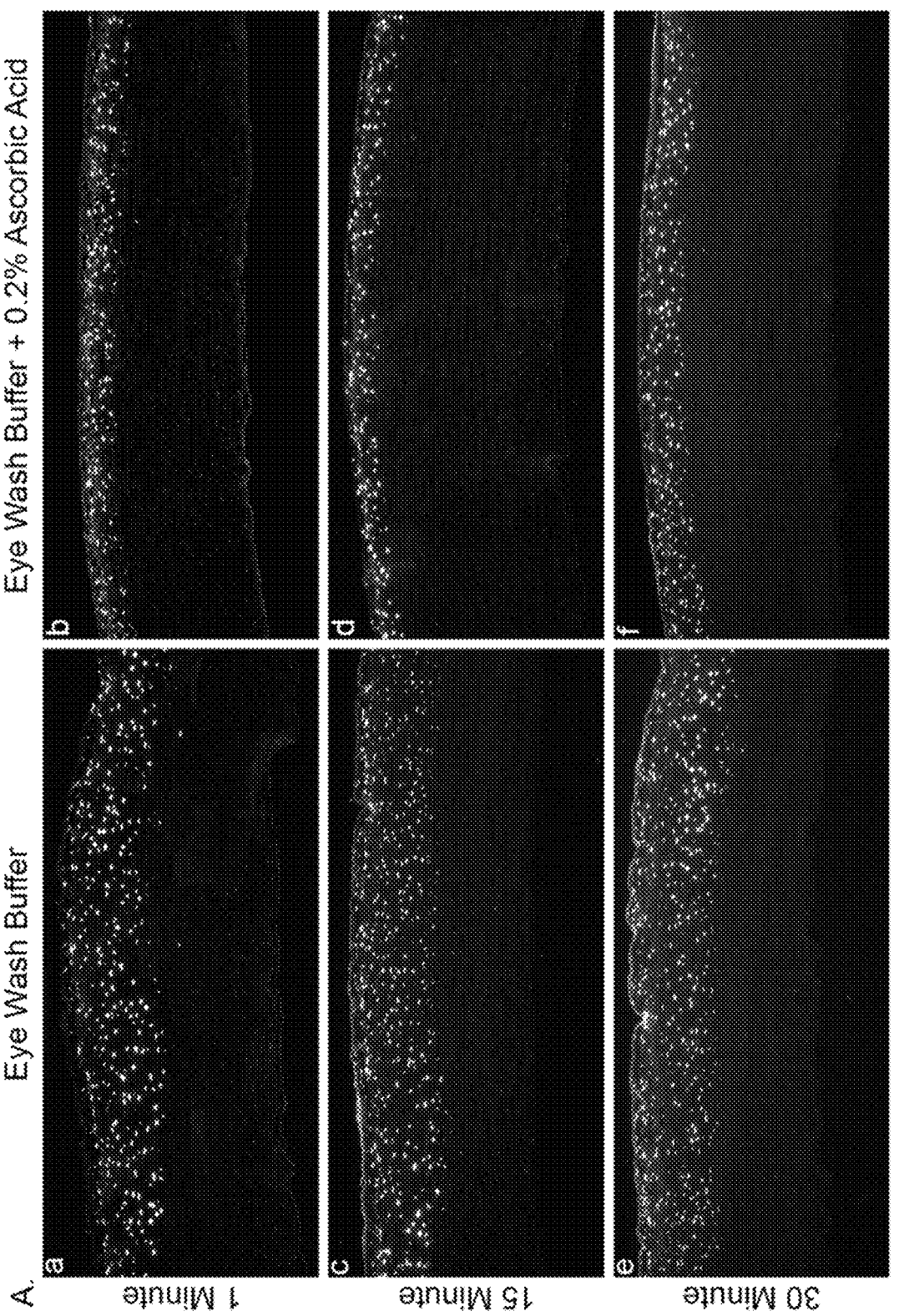
FIGS. 14A-14B: DNA fragmentation pattern of eyes washed with EWB or EWB+0.2% AA following 32% sodium hypochlorite 14A shows corneas exposed to 100 μL of 32% NaOCl and then passively washed by placing in a beaker for 1 min (a), 15 min (b), and 30 min (c) with 100 mL EWB or EWB+0.2% AA. Tissues were fixed, sectioned, and labeled for fragmented DNA with TUNEL (white). 14B and Table 1 show the TUNEL-positive counts for three eyes (three sections per eye) dosed with 32% NaOCl and washed for 1, 15, and 30 min. Error bars indicate the SE for the three independent repeats. EWB=Eye wash buffer.
Figure 14B:
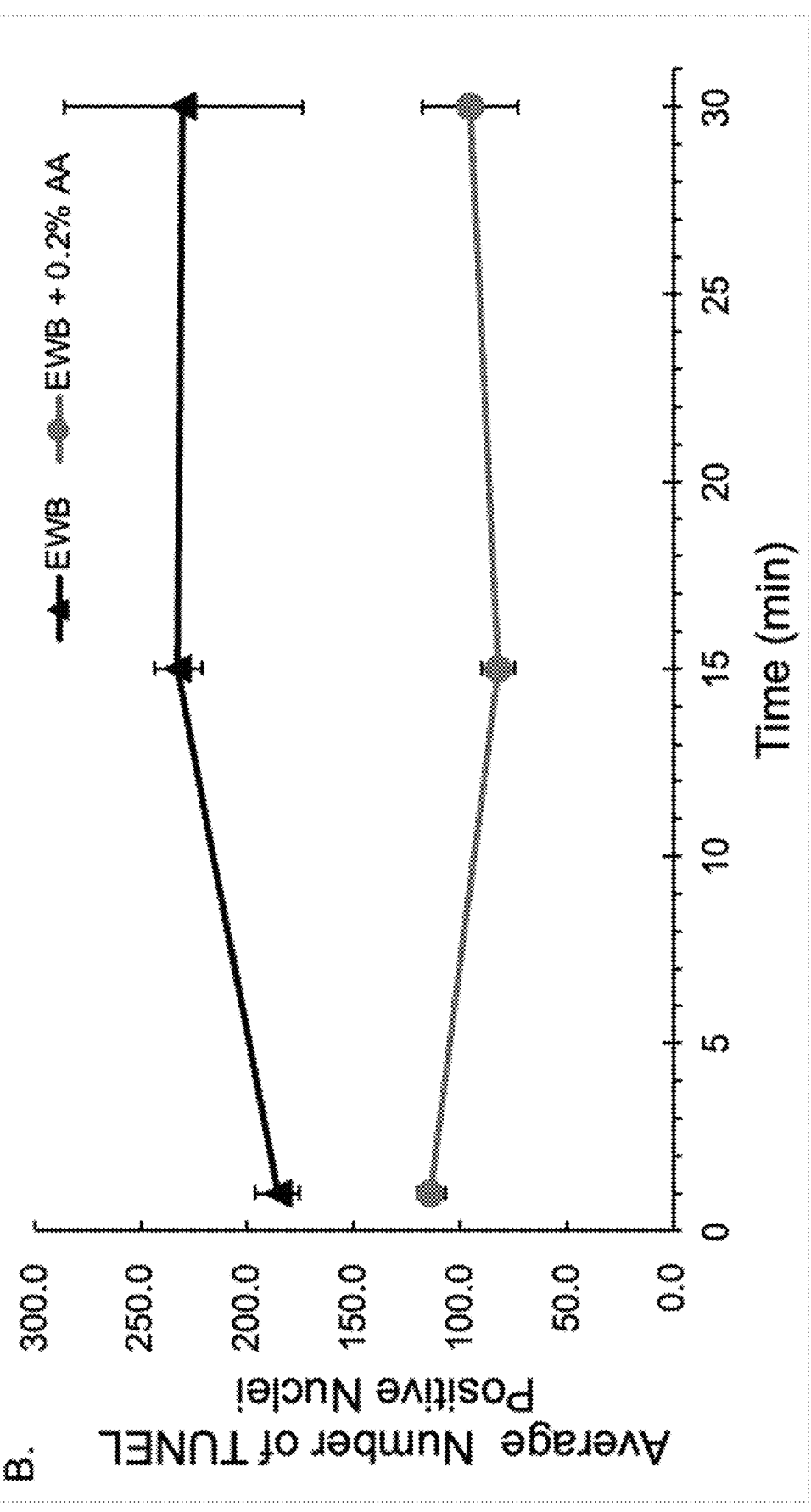

FIG. 14B shows that eyes washed with AA for 15 min had considerably less TUNEL staining than controls. In fact, even a 1-min wash resulted in a considerable reduction in TUNEL staining (FIG. 14A). As shown in FIG. 14B and Table 2, with a 1-min wash, the average number of TUNEL-positive nuclei decreased significantly from 186.0±10.3 in the EWB group to 113.8±6.5 in the 0.2% EWB+AA group (P<0.001). With a 15-min wash, the EWB+0.2% AA group had an average number of TUNEL-positive nuclei of 82.2±7.1, which was significantly less than the EWB control of 232.6±10.4 (P<0.001). TUNEL results are more varied after 30 minutes. For example, in the EWB group, the section average of Eye 1 was 242.3±17.0, 312.0±18.6 for Eye 2, and 136.7±16.1 for Eye 3, while in the EWB+0.2% group the section average of Eye 1 was 142.3±3.5, 88.7±11.1 for Eye 2, and 55.7±6.6 for Eye 3.

3.3 Wash Repeat and 10% AA Study

Figure 15:
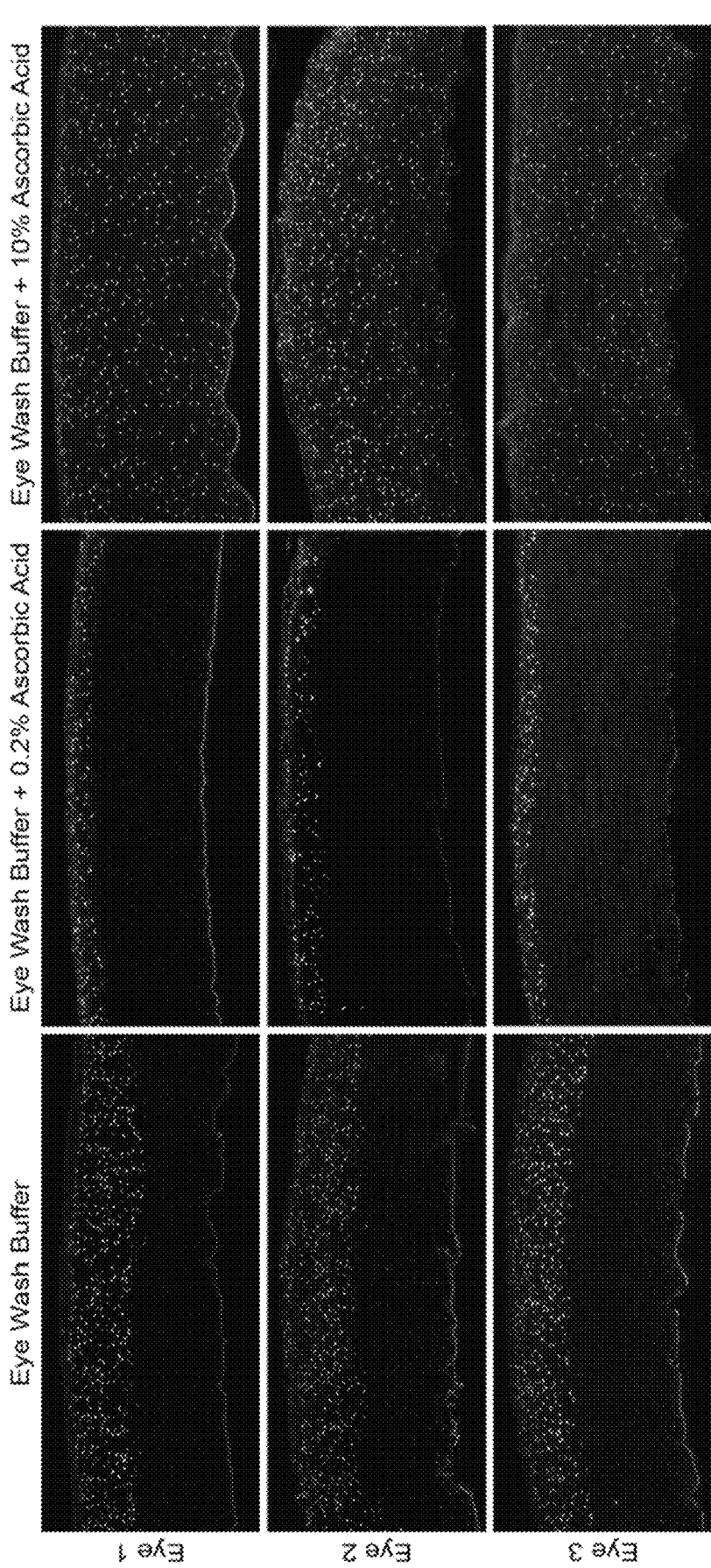
FIG. 15: Corneas were exposed to 100 μL of 32% NaOCl and then washed with EWB plus 0, 0.2%, or 10% AA. Eyes were passively washed by placing in a 100-mL beaker. Tissues were sectioned and labeled with TUNEL (white).

FIG. 15 shows example images and Table 3 shows the averages±SE for triplicate results for all eyes (three eyes) and sections (three sections per eye) exposed to 32% NaOCl, rinsed with 20 mL saline, and then washed for 15 min with EWB or EWB+0.2% AA, or EWB+10% AA. As shown in Table 3, the number of stromal TUNEL-positive nuclei significantly decreased from an average of 256.0±14.4 in the control group to an average of 69.2±5.2 in the 0.2% AA group after washing (P<0.001). The 10% AA group TUNEL positive nuclei were all close to 500, indicating total death of the cornea.

TABLE 3

TUNEL Positive Nuclei Counts for wash repeat and 10% AA study

| Condition | E | Section | S. AVG ± SE | AVG ± SE |
|---|---|---|---|---|
| EWB | 1 | A = 265.0; B = 314.0; C = 260.0 | 279.7 ± 17.2 | 256.0 ± 14.4 |
| | 2 | A = 233.0; B = 241.0; C = 216.0 | 230.0 ± 7.4 | |
| | 3 | A = 277.0; B = 248.0; C = 250.0 | 258.3 ± 9.4 | |
| EWB + | 1 | A = 71.0; B = 73.0; C = 74.0 | 72.7 ± 0.9 | 69.2 ± 5.2 |
| 0.2% AA | 2 | A = 76.0; B = 49.0; C = 52.0 | 59.0 ± 8.5 | |
| | 3 | A = 80.0; B = 77.0; C = 71.0 | 76.0 ± 2.6 | |

TABLE 3-continued

TUNEL Positive Nuclei Counts for wash repeat and 10% AA study

| Condition | E | Section | S. AVG ± SE | AVG ± SE |
|---|---|---|---|---|
| EWB + | 1 | A = 398.0; B = 495.0; C = 404.0 | 432.3 ± 31.4 | 493.0 ± 42.8 |
| 10% AA | 2 | A = 611.0; B = 570.0; C = 546.0 | 575.7 ± 19.0 | |
| | 3 | A = 523.0; B = 456.0; C = 434.0 | 471.0 ± 26.8 | |

EWB = Eye Wash Buffer;
E = Eye Number;
AA = Ascorbic Acid;
S. AVG ± SE = Section Average ± Standard Error;
AVG ± SE = Overall Average ± Standard Error of all 3 sections In the initial wash study (FIG. 14 and Table 2), for the 15 minute wash time, the overall average TUNEL positive nuclei count was 232.6±10.4 for the EWB group and 82.2±7.1 for the EWB+0.2% AA group. For the wash study repeat (FIG. 15 and Table 3), the overall average TUNEL positive nuclei count was 256.0±14.4 for the EWB group and 69.2±5.2 for the EWB+0.2% AA group. Comparing the average TUNEL positive nuclei counts between the two studies, the EWB averages were 232.6±10.4 vs. 256.0±14.4 and the EWB+0.2% AA averages were 82.2±7.1 vs. 69.2±5.2.

Figure 16A:
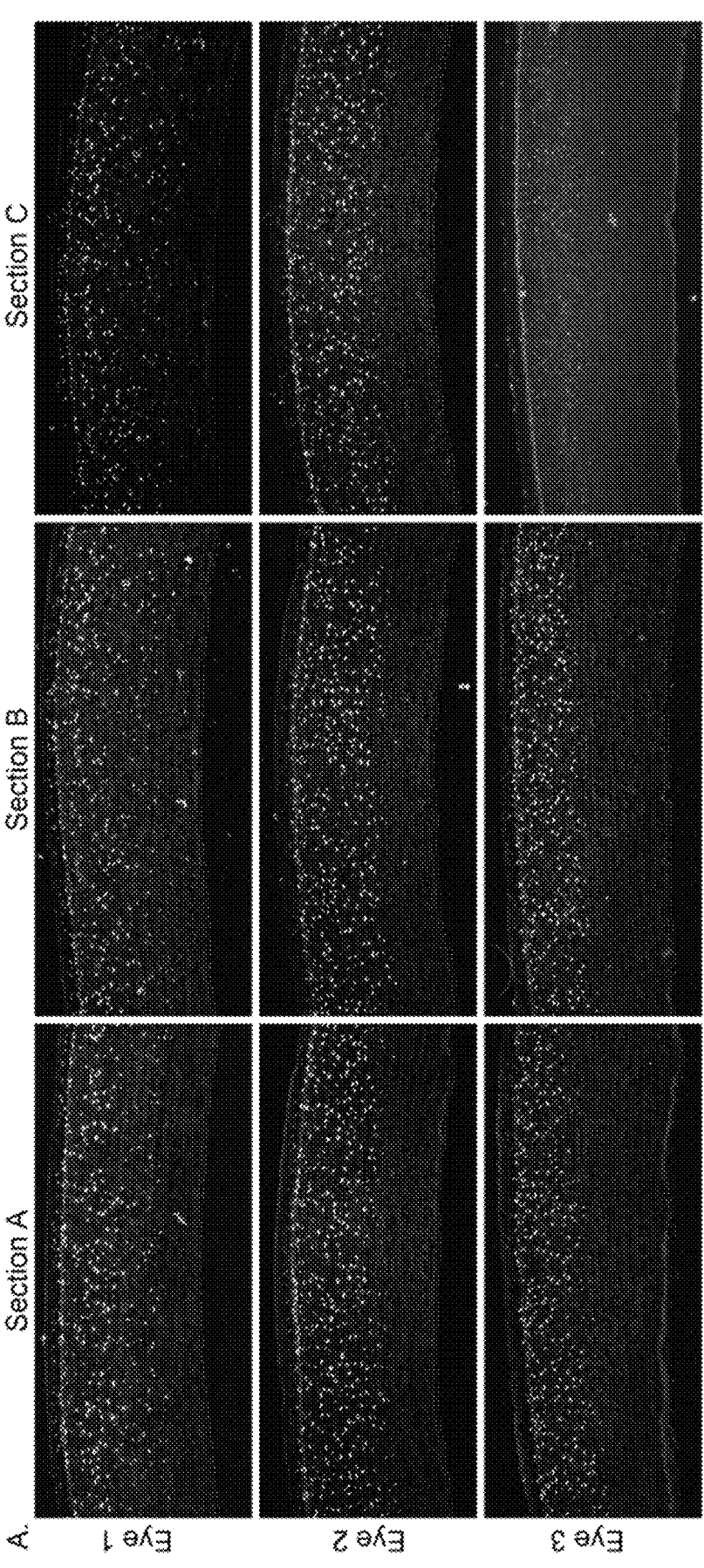
FIGS. 16A-16B: 16A: DNA fragmentation pattern of the cornea of eyes dosed with 32% sodium hypochlorite and then actively washed for 15 minutes with 500 mL tap water. 16B: DNA fragmentation of the cornea of eyes dosed with 32% sodium hypochlorite and then actively washed for 15 minutes with 500 mL eye wash buffer.
Figure 16B:
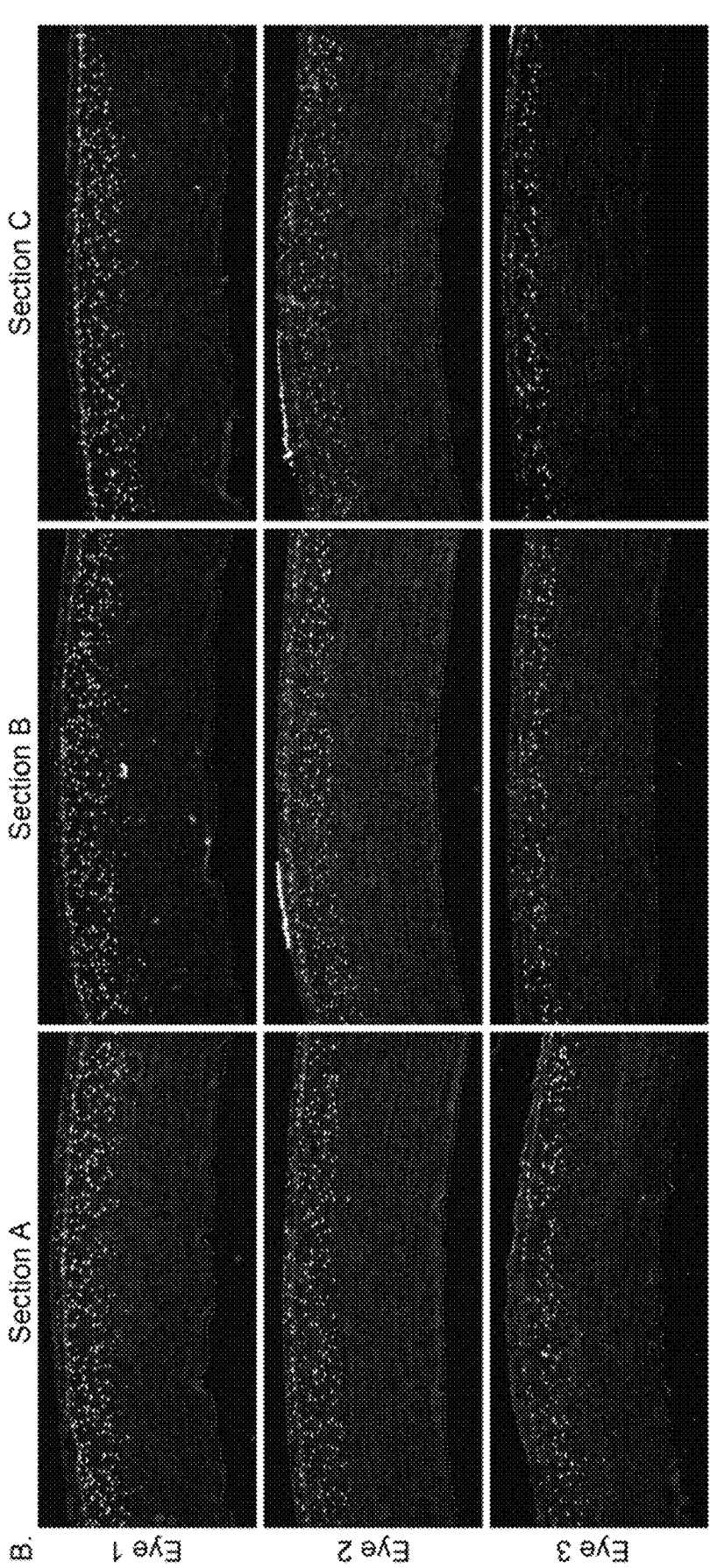
Figure 16C:
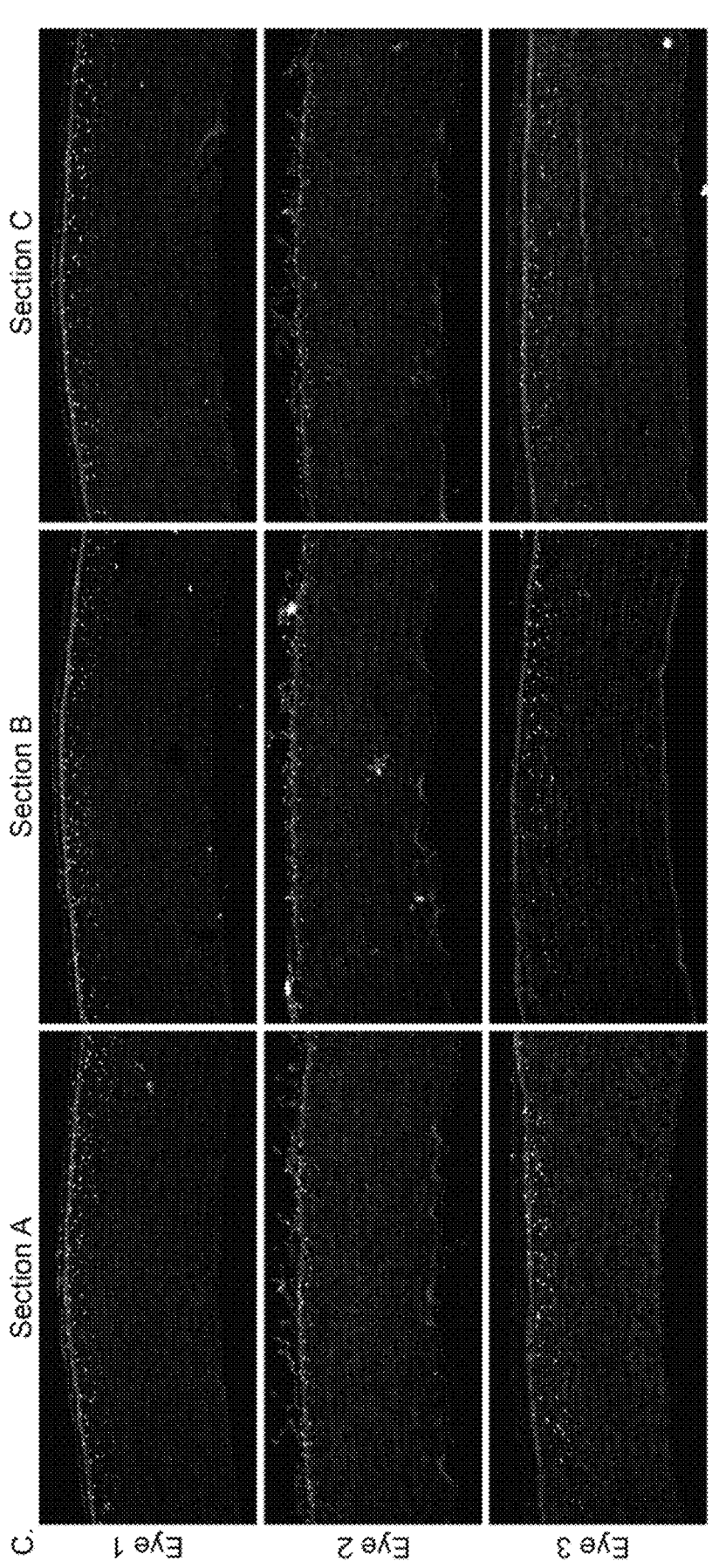
FIGS. 16C-16D: 16C. DNA fragmentation of the cornea of eyes dosed with 32% sodium hypochlorite and then actively washed for 15 minutes with 500 mL eye wash buffer+0.2% ascorbic acid. 16D. DNA fragmentation of the cornea of eyes dosed with 100 μL sterile water and then actively washed for 15 minutes with 500 mL tap water, EWB or EWB+0.2%. Fragmented corneal DNA for eyes dosed with 100 μL of 32% NaOCl or sterile water, rinsed with 20 mL saline, and then actively washed 15 min using the 500-mL wash bottle (shown in FIG. 1B). After washing, eyes were incubated for 24 h under tissue culture conditions, and corneas were removed, fixed, and then frozen. Corneas were then sectioned and labeled with TUNEL (white punctate spots). All three eyes (nine sections) are shown for each wash condition. Fragmented DNA counts are provided in Table 4.
Figure 16D:
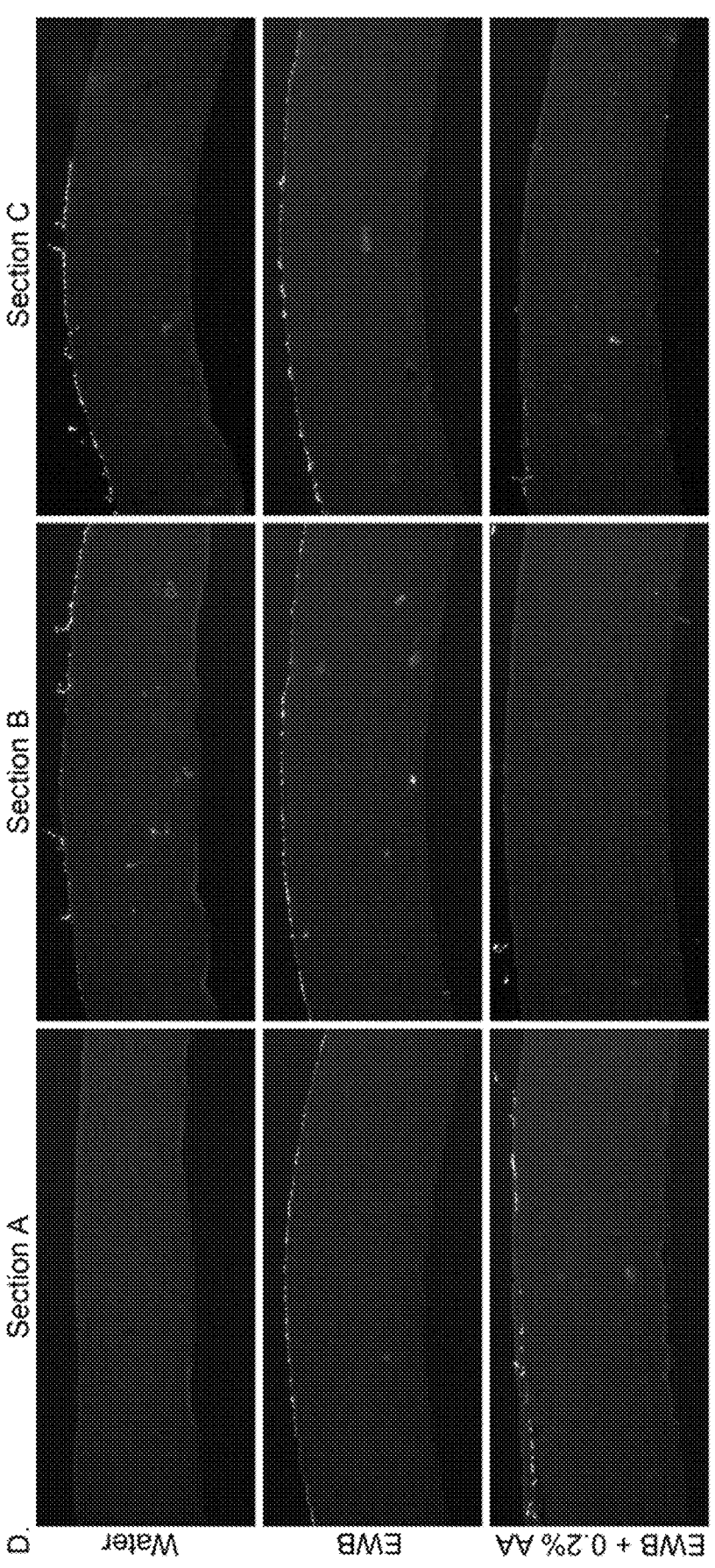

3.4 Fragmented Corneal DNA for Eyes Dosed with 32% Sodium Hypochlorite and then Actively Washed with Water, EWB or EWB+0.2% AA, Using the 500-mL Wash Bottle FIGS. 16A, B and C show TUNEL stained images for corneal sections of eyes exposed to 32% NaOCl, rinsed with 20 mL saline, and then actively washed with 500 mL tap water, EWB, or EWB+0.2% AA. Control eyes exposed to water only (no NaOCl) and then washed with water, EWB, or EWB+0.2% AA are shown in FIG. 16D.

Table 4A-4B shows the TUNEL positive nuclei counts for each section (A, B, and C) for each individual eye (1, 2, or 3), the section average±SE, and overall average±SE for the 500-mL wash bottle study shown in FIG. 16. For the water wash condition (FIG. 16A), the overall TUNEL positive nuclei average was 254.9±17.8 and the individual TUNEL positive nuclei counts for Eye 1 had a section average of 238.0±2.6 (A=234.0 per section, B=243.0 per section, C=237.0 per section), Eye 2 had a section average of 287.7±4.1 (A=289.0 per section, B=280.0 per section, C=294.0 per section), and Eye 3 had a section average of 231.0±4.0 (A=227.0 per section, B=235.0 per section, C=Not used for data analysis due to poor staining). For the EWB wash condition (FIG. 16B), the overall TUNEL positive nuclei average was 167.3±33.5 and the individual TUNEL positive nuclei counts for Eye 1 had a section average of 228.3±9.9 (A=217.0 per section, B=248.0 per section, C=220.0 per section), Eye 2 had a section average of 161.0±6.7 (A=160.0 per section, B=173.0 per section, C=150.0 per section), and Eye 3 had a section average of 112.7±11.9 (A=130.0 per section, B=118.0 per section, C=90.0 per section). For the EWB+0.2% AA wash condition (FIG. 16C), the overall TUNEL positive nuclei counts was 45.6±15.5 and the individual TUNEL positive nuclei counts for Eye 1 had a section average of 70.7±1.8 (A=68.0 per section, B=70.0 per section, C=74.0 per section), Eye 2 had a section average of 17.3±2.9 (A=22.0 per section, B=12.0 per section, C=18.0 per section), and Eye 3 had a section average of 48.7±1.2 (A=48.0 per section, B=51.0 per section, C=47.0 per section).

TABLE 4A

TUNEL Positive Nuclei Counts for 500 mL Wash Bottle Study
A. Treatment groups: Eyes exposed to 32% Sodium Hypochlorite then washed

| Wash | E | Section | S. AVG ± SE | AVG ± SE | P-Values |
|---|---|---|---|---|---|
| Water | 1 | A = 234.0; B = 243.0; C = 237.0 | 238.0 ± 2.6 | 254.9 ± 17.8 | n/a |
| | 2 | A = 289.0; B = 280.0; C = 294.0 | 287.7 ± 4.1 | | |
| | 3 | A = 227.0; B = 235.0; C = *N/A | 231.0 ± 4.0 | | |
| EWB | 1 | A = 217.0; B = 248.0; C = 220.0 | 228.3 ± 9.9 | 167.3 ± 33.5 | P < 0.001 |
| | 2 | A = 160.0; B = 173.0; C = 150.0 | 161.0 ± 6.7 | | |
| | 3 | A = 130.0; B = 118.0; C = 90.0 | 112.7 ± 11.9 | | |
| EWB + 0.2% AA | 1 | A = 68.0; B = 70.0; C = 74.0 | 70.7 ± 1.8 | 45.6 ± 15.5 | P < 0.001 |
| | 2 | A = 22.0; B = 12.0; C = 18.0 | 17.3 ± 2.9 | | |
| | 3 | A = 48.0; B = 51.0; C = 47.0 | 48.7 ± 1.2 | | |

E = Eye Number;
S. AVG ± SE = Section Average ± Standard Error;
AVG ± SE = Overall Average ± Standard Error of all 3 sections;
EWB = Eye Wash Buffer;
AA = Ascorbic Acid;
*N/A = Poor staining (not used)

TABLE 4

TUNEL Positive Nuclei Counts for 500 mL Wash Bottle Study
B. Controls: Eyes exposed to water then washed

| Wash | E | Section | S. AVG ± SE |
|---|---|---|---|
| Water | 1 | A = 0.0; B = 0.0; C = 0.0 | 0.0 ± 0.0 |
| EWB | 2 | A = 0.0; B = 0.0; C = 0.0 | 0.0 ± 0.0 |
| EWB + 0.2% AA | 3 | A = 0.0; B = 0.0; C = 0.0 | 0.0 ± 0.0 |

E = Eye Number;
S. AVG ± SE = Section Average ± Standard Error;
AVG ± SE = Overall Average ± Standard Error of all 3 sections;
EWB = Eye Wash Buffer;
AA = Ascorbic Acid Table 5A-5B shows the Depth of Damage (DoD) measurements for each section (A, B, or C) for each individual eye (1, 2, or 3), the section average±SE, and overall average #SE for the 500-mL wash bottle study shown in FIG. 16. For the water wash condition (FIG. 16A), the overall DoD average was 59.6±3.6% and the individual DoD for Eye 1 had a section average of 68.5±0.5% (A=68.4%, B=69.4%, C=67.6%), Eye 2 had a section average of 60.9±0.7% (A=62.3%, B=59.8%, C=60.7%), and Eye 3 had a section average of 44.2±2.8% (A=47.0%, B=41.4%, C=Not used for data analysis due to poor staining). For the EWB wash condition (FIG. 16B), the overall DoD average was 30.9±1.6, which is significantly different than the water wash condition of 59.6±3.6% (P<0.001). The individual DoD for the EWB was: Eye 1 had a section average of 34.7±2.5 (A=32.6, B=39.6, C=32.0), Eye 2 had a section average of 29.4±1.0 (A=28.1, B=28.7, C=31.4), and Eye 3 had a section average of 26.2±2.4 (A=31.0, B=23.9, C=23.6). For the EWB+0.2% AA wash condition (FIG. 16C), the overall DoD average was 13.8±1.4 which was significantly different than 30.9±1.6 for the EWB condition (P<0.001). The individual AA+0.2% AA DoD results were: Eye 1 had a section average of 16.8±0.2 (A=16.4, B=16.9, C=17.0), Eye 2 had a section average of 9.1±0.4 (A=8.7, B=9.9, C=8.5), and Eye 3 had a section average of 16.4±0.1 (A=16.7, B=16.2, C=16.4).

TABLE 5A

Depth of Damage (%) Measurements for 500 mL Wash Bottle Study
A. Treatment groups: Eyes exposed to 32% Sodium Hypochlorite then washed

| Wash | E | Section | S. AVG ± SE | AVG ± SE | P-Values |
|---|---|---|---|---|---|
| Water | 1 | A = 68.4; B = 69.4; C = 67.6 | 68.5 ± 0.5 | 59.6 ± 3.6 | n/a |
| | 2 | A = 62.3; B = 59.8; C = 60.7 | 60.9 ± 0.7 | | |
| | 3 | A = 47.0; B = 41.4; C = *N/A | 44.2 ± 2.8 | | |
| EWB | 1 | A = 32.6; B = 39.6; C = 32.0 | 34.7 ± 2.5 | 30.9 ± 1.6 | P < 0.001 |
| | 2 | A = 28.1; B = 28.7; C = 31.4 | 29.4 ± 1.0 | | |
| | 3 | A = 31.0; B = 23.9; C = 23.6 | 26.2 ± 2.4 | | |

TABLE 5A-continued

Depth of Damage (%) Measurements for 500 mL Wash Bottle Study
A. Treatment groups: Eyes exposed to 32% Sodium Hypochlorite then washed

| Wash | E | Section | S. AVG ± SE | AVG ± SE | P-Values |
|---|---|---|---|---|---|
| EWB + | 1 | A = 16.4; B = 16.9; C = 17.0 | 16.8 ± 0.2 | 13.8 ± 1.4 | P < 0.001 |
| 0.2% AA | 2 | A = 8.7; B = 9.9; C = 8.5 | 9.1 ± 0.4 | | |
| | 3 | A = 16.7; B = 16.2; C = 16.4 | 16.4 ± 0.1 | | |

E = Eye Number;
Section = measurements for each section;
S. AVG ± SE = Section Average ± Standard Error;
AVG ± SE = Overall Average ± Standard Error of all 3 eyes;
EWB = Eye Wash Buffer;
AA = Ascorbic Acid;
*N/A = Poor staining (not used)

TABLE 5B

Depth of Damage (%) Measurements for 500 mL Wash Bottle Study
B. Controls: Eyes exposed to water then washed

| Wash | E | Section | S. AVG ± SE |
|---|---|---|---|
| Water | 1 | A = 0.0; B = 0.0; C = 0.0 | 0.0 ± 0.0 |
| EWB | 2 | A = 0.0; B = 0.0; C = 0.0 | 0.0 ± 0.0 |
| EWB + 0.2% AA | 3 | A = 0.0; B = 0.0; C = 0.0 | 0.0 ± 0.0 |

E = Eye Number;
Section = measurements for each section;
S. AVG ± SE = Section Average ± Standard Error;
EWB = Eye Wash Buffer;
AA = Ascorbic Acid The DoD for water vs. EWB+0.2% AA are significantly different. The water group had an average DoD of 59.6±3.6% vs. the EWB+0.2% AA group which had an average DoD of 13.8±1.4 (P<0.001). The difference in DoD is also obvious when looking at the TUNEL stained images (compare FIG. 16A with FIG. 16C).

ROS and extreme pH results Supplementary Table 1 shows the identified chemicals by name, CASRN, and in vivo results; references are shown in Supplementary Table 3 for ROS association (if found) and pH (if found). This list includes 108 chemicals that cause extreme or irreversible damage to the eye in vivo. Of these 108 chemicals and as detailed in Supplementary Table 1B, 38 (35.2%) were found to be associated with ROS. We were only able to identify 29 published pH values for chemicals that cause extreme or irreversible eye damage (Table 1). Of these 29 chemicals, 21 were identified in publications or supplier websites as either highly acidic or highly alkaline, indicating that 72.4% of the identified published pH values for chemicals that cause extreme or irreversible eye damage have extreme pH values. As shown in Supplementary Table 2, when ROS and estimates for the percentage with extreme pH rates are combined (ROS-associated chemicals and an estimate of the percentage of strong acids and bases not associated with ROS), the estimated rate of occurrence=82.4%. Although measuring actual pH values would improve the sample size and estimate, and some of the chemicals could be ROS but apparently not studied/published (or outside our search criteria), based on this analysis, we estimate that over 80% of the extreme and irreversible ocular toxins are associated with ROS and/or have extreme pH values.

Supplementary TABLE 1

| | | | | | |
|---|---|---|---|---|---|
| Chem. No. | Chemical Name | CASRN | in vivo GHS | ROS | ROS Ref. |
| 1 | Captan 90-concentrate | 133-06-2 | 1 | Identified | Scariot et al. 2017 |
| 2 | 4-(1,1,3,3-Tetramethylbutyl)phenol | 140-66-9 | 1 | Identified | Aydoğan et al. 2008; Olaniyan et al. 2022 |
| 3 | Quinacrine | 69-05-6 | 1 | Identified | Jing et al. 2018; Kumar et al. 2020 |
| 4 | Sodium oxalate | 62-76-0 | 1 | Identified | Kumar et al. 2023; Patel et al. 2018 |
| 5 | Hexadecyltrimethylammonium chloride (5%) | 112-02-7 | 1 | Identified | Zhang et al. 2019 |
| 6 | Glycolic acid | 79-14-1 | 1 | Identified | Lai et al. 2011 |
| 7 | Sodium lauryl sulfate (15%) | 151-21-3 | 1 | Identified | Mizutani et al. 2016 |
| 8 | Lauric Acid | 143-07-7 | 1 | Identified | Lappano et al. 2017 |
| 9 | Tributyltin oxide | 56-35-9 | 1 | Identified | Yang et al. 2019; Xiao et al. 2021 |

Supplementary TABLE 1-continued

Chemicals That Cause Extreme and Irreversible Damage to the Eye

| Chem. No. | Chemical Name | CASRN | in vivo GHS | ROS | ROS Ref. |
|---|---|---|---|---|---|
| 10 | Benzalkonium chloride (1%) | 63449-41-2/ 8001-54-5 | 1 | Identified | Rogov et al. 2020; Zhang et al. 2017; Clouzeau et al. 2012 |
| 11 | Acetic acid | 64-19-7 | 1 | Identified | Kurokawa et al. 2022; Terasaki et al. 2018 |
| 12 | Sodium lauryl sulfate | 151-21-3 | 1 | Identified | Mizutani et al. 2016 |
| 13 | Sodium salicylate | 54-21-7 | 1 | Identified | Chung et al. 2003; Wang et al. 2017 |
| 14 | Triton X-100 (10%) | 9002-93-1 | 1 | Identified | Li et al. 2020 |
| 15 | n-Butanol | 71-36-3 | 1 | Identified | Köktürk et al. 2020; Rutherford et al. 2010 |
| 16 | Benzyl alcohol | 100-51-6 | 1 | Identified | Chang et al. 2011 |
| 17 | Lactic Acid | 50-21-5 | 1 | Identified | Luo et al. 2017 |
| 18 | m-Phenylene diamine | 108-45-2 | 1 | Identified | Zanoni et al. 2015 |
| 19 | p-Tert-butylphenol | 98-54-4 | 1 | Identified | Cui et al. 2022; Manga et al. 2006 |
| 20 | Pyridine | 110-86-1 | 1 | Identified | Samantaray et al. 2017 |
| 21 | Promethazine hydrochloride | 58-33-3 | 1 | Identified | He et al. 2011 |
| 22 | Benzalkonium chloride (10%) | 63449-41-2/ 8001-54-5 | 1 | Identified | Rogov et al. 2020; Zhang et al. 2017; Clouzeau et al. 2012 |
| 23 | Benzalkonium chloride (100%) | 63449-41-2/ 8001-54-5 | 1 | Identified | Rogov et al. 2020; Zhang et al. 2017; Clouzeau et al. 2012 |
| 24 | Benzalkonium chloride (5%) | 63449-41-2/ 8001-54-5 | 1 | Identified | Rogov et al. 2020; Zhang et al. 2017; Clouzeau et al. 2012 |
| 25 | Ethylhexyl acid phosphate ester | 12645-31-7 | 1 | Identified | Saquib et al. 2022; Jin et al. 2024 |
| 26 | Domiphen bromide (10%) | 538-71-6 | 1 | Identified | Tits et al. 2021; Chen et al. 2024 |
| 27 | Chlorhexidine | 55-56-1 | 1 | Identified | Barbin et al. 2008; Yeung et al. 2007 |
| 28 | Cetyltrimethylammonium bromide (10%) | 57-09-0 | 1 | Identified | Nakata et al. 2011 |
| 29 | Cetyltrimethylammonium bromide | 57-09-0 | 1 | Identified | Nakata et al. 2011 |
| 30 | Hexadecyltrimethylammonium chloride (25%) | 112-02-7 | 1 | Identified | Zhang et al. 2019 |
| 31 | Benzethonium chloride (10%) | 121-54-0 | 1 | Identified | Gheorghe et al. 2020 |
| 32 | Benzoic acid | 65-85-0 | 1 | Identified | Niu et al. 2020 |
| 33 | Acetic Acid (10%) | 64-19-7 | 1 | Identified | Kurokawa et al. 2022; Terasaki et al. 2018 |
| 34 | Acid red 92 | 18472-87-2 | 1 | Identified | Goyal et al. 2016; Abd El Rahman et al. 2017 |

Supplementary TABLE 1-continued

Chemicals That Cause Extreme and Irreversible Damage to the Eye

| Chem. No. | Chemical Name | CASRN | in vivo GHS | ROS | ROS Ref. |
|---|---|---|---|---|---|
| 35 | Cetylpyridinium chloride | 6004-24-6 | 1 | Identified | Qiu et al. 2022 |
| 36 | Triton X-100 | 9002-93-1 | 1 | Identified | Li et al. 2020 |
| 37 | Nonylphenyl-polyethylene glycol | 9016-45-9 | 1 | Identified | Zerin et al. 2017 |
| 38 | 4-(1,1-Dimethylethyl)-α-methyl-benzenepropanal (Protectol PP) | 80-54-6 | 1 | Identified | Usta et al. 2013 |

| Chem. No. | Chemical Name | CASRN | in vivo GHS | pH | pH Ref. |
|---|---|---|---|---|---|
| 39 | Distearyldimethylammonium chloride | 107-64-2 | 1 | 5.5 | Ohno et al. 1999 |
| 40 | Paraformaldehyde | 30525-89-4 | 1 | 7.6 | Sigma Aldrich; Thermo Fisher Scientific |
| 41 | 2-Methylbutyric acid | 116-53-0 | 1 | 2.8 | Ohno et al. 1999 |
| 42 | Tetraethylene glycol diacrylate | 17831-71-9 | 1 | 5.2 | Eskes et al. 2014 |
| 43 | 1-Naphthalene acetic acid | 86-87-3 | 1 | 5.0 | PubChem |
| 44 | Calcium thioglycolate | 5793-98-6 | 1 | 11.6 | Ohno et al. 1999 |
| 45 | Sodium perborate tetrahydrate | 10486-00-7 | 1 | 10.4 | Sigma Aldrich |
| 46 | Butyl cellosolve | 111-76-2 | 1 | 7.0 | Sigma Aldrich |
| 47 | Cyclohexanol | 108-93-0 | 1 | 6.5 | Sigma Aldrich |
| 48 | Tetrahydrofuran | 109-99-9 | 1 | 8.0 | Sigma Aldrich |
| 49 | alpha-Ketoglutaric acid | 328-50-7 | 1 | 1.5 | Fisher Scientific |
| 50 | Parafluoraniline | 371-40-4 | 1 | 7.4 | Sigma Aldrich |
| 51 | 2-Hydroxy iso-butyric acid | 594-61-6 | 1 | 1.0 | Fisher Scientific |
| 52 | (3-Aminopropyl)triethoxy silane | 919-30-2 | 1 | 11.0 | Sigma Aldrich |
| 53 | Diethylethanolamine | 100-37-8 | 1 | 11.5 | Fisher Scientific |
| 54 | Imidazole | 288-32-4 | 1 | 10.5 | Sigma Aldrich |
| 55 | n-Octylamine | 111-86-4 | 1 | 11.8 | Sigma Aldrich |
| 56 | Sodium hydroxide (10%) | 1310-73-2 | 1 | 14.0 | Sigma Aldrich |
| 57 | Trichloroacetic acid (30%) | 76-03-9 | 1 | <1.0 | Sigma Aldrich |
| 58 | Butanedioic acid, sulfo-, 1,4-bis(2-ethylhexyl) ester, sodium salt | 577-11-7 | 1 | 6.5 | Ohno et al. 1999 |
| 59 | Potassium laurate | 10124-65-9 | 1 | 10.5 | Ohno et al. 1999 |
| 60 | Stearyltrimethylammonium chloride | 112-03-8 | 1 | 4.2 | Ohno et al. 1999 |
| 61 | Sodium hydroxide | 1310-73-2 | 1 | 14.0 | Sigma Aldrich |
| 62 | Lauryldimethylamine oxide | 1643-20-5 | 1 | 9.0 | Sigma Aldrich |
| 63 | 1-Naphthalene acetic acid (20%) | 86-87-3 | 1 | 5.0 | PubChem |
| 64 | beta-Resorcylic acid | 89-86-1 | 1 | 3.0 | Fisher Scientific |
| 65 | Sodium hydrogen sulfate | 7681-38-1 | 1 | <1.0 | Fisher Scientific |
| 66 | Tetraoctylammonium bromide | 14866-33-2 | 1 | 3.9 | Sigma Aldrich |
| 67 | Sodium hydroxide (1%) | 1310-73-2 | 1 | 14.0 | Sigma Aldrich |
| 68 | 2,5-Dimethyl-2,5-hexanediol (20%) | 110-03-2 | 1 | | |
| 69 | 1-Chloroctan-8-ol | 23144-52-7 | 1 | | |
| 70 | Triethanolamine orthovanadate | 13476-99-8 | 1 | | |
| 71 | 1-Dodecanaminium, N-(2-hydroxy-3-sulfopropyl)-N,N-dimethyl-, inner salt | 13197-76-7 | 1 | | |
| 72 | Butylnaphthalenesulfonic acid sodium salt | 25638-17-9 | 1 | | |
| 73 | Quaternary ammonium compounds, benzyl-C12-16-alkyldimethyl, chlorides | 68424-85-1 | 1 | | |
| 74 | Coco alkyldimethyl betaine | 68424-94-2 | 1 | | |
| 75 | Quaternary ammonium compounds, di-C12-15-alkyldimethyl, chlorides | 68910-56-5 | 1 | | |
| 76 | 3-Methyl-pentynol | 77-75-8 | 1 | | |
| 77 | 2-Naphthalenesulfonic acid, 6-hydroxy-,monosodium salt, polymer with formaldehyde and hydroxymethylbenzenesulfonic aid monosodium salt | 85255-76-1 | 1 | | |

Supplementary TABLE 1-continued

Chemicals That Cause Extreme and Irreversible Damage to the Eye

| Chem. No. | Chemical Name | CASRN | in vivo GHS | ROS | ROS Ref. |
|---|---|---|---|---|---|
| 78 | Sulfuric acid, ono-C12-14-alkyl | 90583-18-9 | 1 | | |
| 79 | Methoxyethyl acrylate | 3121-61-7 | 1 | | |
| 80 | Benzensulphonylchloride | 98-09-9 | 1 | | |
| 81 | Hydroxyethyl acrylate | 818-61-1 | 1 | | |
| 82 | 2-Benzyl-4-chlorophenol | 120-32-1 | 1 | | |
| 83 | 2-Hydroxy iso-butyric acid ethyl ester | 80-55-7 | 1 | | |
| 84 | Cetylpyridinium bromide (6%) | 140-72-7 | 1 | | |
| 85 | Cetylpyridinium bromide (10%) | 140-72-7 | 1 | | |
| 86 | 1-Naphthalene acetic acid Na salt | 61-31-4 | 1 | | |
| 87 | Dibenzoyl-L-tartaric acid | 2743-38-6 | 1 | | |
| 88 | n-Acetyl-DL-methionine | 1115-47-5 | 1 | | |
| 89 | 1,2-Benzisothiazol-3(2H)-one | 2634-33-5 | 1 | | |
| 90 | 4,4'-(4,5,6,7-Tetrabromo-3H-2,1-benzoxathiol-3-ylidene)bis[2,6-dibromophenol] S,S-dioxide | 4430-25-5 | 1 | | |
| 91 | bis-(3-Aminopropyl)-tetramethyldisiloxane | 2469-55-8 | 1 | | |
| 92 | N-(2-Methylphenyl)-iminodicarbonimidic diamide (1-(o-Tolyl)biguanide) | 93-69-6 | 1 | | |
| 93 | Methyl thioglycolate | 2365-48-2 | 1 | | |
| 94 | 2,2-Dimethylbutanoic acid | 595-37-9 | 1 | | |
| 95 | (Ethylenediamine propyl)trimethoxysilane | 1760-24-3 | 1 | | |
| 96 | 4-Tert-butylcatechol | 98-29-3 | 1 | | |
| 97 | Benzene, 1,1'-oxybis-, tetrapropylene derivatives, sulfonated, sodium salts | 119345-04-9 | 1 | | |
| 98 | Triethanolamine polyoxyethylene(3.0) lauryl ether sulfate | 27028-82-6 | 1 | | |
| 99 | Naphthalene-2,7-diol | 582-17-2 | 1 | | |
| 100 | 2-Methylresorcinol | 608-25-3 | 1 | | |
| 101 | TNO-35 (Propyl-lactate) | 616-09-1 | 1 | | |
| 102 | Polyoxyethylene(10) polyoxypropylene(1.5) lauryl-myristyl ether | 68439-51-0 | 1 | | |
| 103 | Sodium polyoxyethylene(3) lauryl ether sulfate | 9004-82-4 | 1 | | |
| 104 | Polyoxyethylene(20) hydrogenated tallow amine | 61790-82-7 | 1 | | |
| 105 | 1,2,4-Triazole sodium salt | 41253-21-8 | 1 | | |
| 106 | 2-Nitro-4-thiocyanatoaniline | 54029-45-7 | 1 | | |
| 107 | 3,4-Dichlorophenyl isocyanate | 102-36-3 | 1 | | |
| 108 | 3-Diethylaminopropionitrile | 5351-04-2 | 1 | | |

Chem. No. = Chemical Number; CASRN = Chemical Abstracts Service Registry Number; in vivo = GHS Category 1 (Chemicals that cause extreme and irreversible damage to the eye); ROS = Reactive Oxygen Species; Ref. = Reference; see Supplementary Table 3 for full references.
1 = Barroso et al., 2017

Supplementary TABLE 2

Results Summary
A. ROS

| n | # ROS | % ROS/n | # non-ROS |
|---|---|---|---|
| 108 | 38 | 35.2% (38/108) | 70 |

B. Extreme pH

| # pH | # XpH | % XpH | Corrected n | Corrected % XpH |
|---|---|---|---|---|
| 29 | 21 | 72.4% (21/29) | 51.0 {(70)*0.724} | 89.0 (38 + 51) |

C. ROS or Extreme pH

| Equation 1 | All Numbers Plugged into Equation 1 |
|---|---|
| [# ROS + {(# non ROS) × % XpH}] ÷ n= | [38 ± {(70) × 0.724}] ÷ 108 = 82.4% (89/108) |

ROS = Reactive oxygen species;
n = number of chemicals that cause extreme and irreversible damage to the eye (GHS Category 1);
ROS = number of ROS identified Category 1 chemicals;
non-ROS = number of Category 1 chemicals that were not identified to be ROS;
pH = number of non-ROS chemicals with a pH identified;
XpH = number of pH identified non-ROS chemicals with an extreme pH of less than 5 or greater than 9
*calculations include pH values for diluted chemicals In this study, we tested the hypothesis that washing with a buffered AA eyewash solution reduces eye damage caused by the strong oxidizer NaOCl. The use of food-source eyes versus in vivo eyes allowed for multiple conditions to be rapidly assessed, with greater dosing and washing precision, resulting in rapid discovery at lower cost than would have been possible with live animals. New Zealand White rabbits are the benchmark for ophthalmic research and regulatory testing (York and Steiling, 1998; Mapara et al., 2012; Zernii et al., 2016; Qin et al., 2022), and there are publicly available in vivo New Zealand White rabbit eye irritation databases for a broad range of chemicals (Barroso et al., 2017; ECETOC, 1998). The IVD kit prediction model was developed using New Zealand White rabbit eyes, testing a large number of chemicals with existing in vivo New Zealand White rabbit data, and correlating these data with IVD DoD results. For this model, a DoD greater than 20% predicts extreme, permanent eye injury or even blindness in vivo (extreme or irreversible injury, GHS category 1), and a DoD less than 20% predicts a minor amount of damage (GHS category 2, eye irritation) that will completely heal within 21 days in vivo (Lebrun et al., 2019).

The results indicate that a buffered eyewash solution with 0.2% AA was more effective at mitigating corneal damage after strong oxidizer exposure than washing with eye wash buffer alone (see FIGS. 14, 15, 16). However, since the current recommended treatment is flushing the eyes with tap water, water versus EWB+0.2% AA is a relevant comparison. As shown in FIG. 16 and Table 4, after washing with 500 mL tap water, the dead cell average was 254.9±17.8 but after washing with 500 mL EWB+0.2% AA the dead cell average was significantly reduced to 45.6±15.5 (P<0.001). Further, studies of washing with pH buffer and buffer with antioxidants might result better emergency eye wash treatments that reduce eye damage after toxic chemical exposure to the eyes. It should be noted that in this context washing with tap water will remove tears which contain antioxidants (including ascorbic acid) and have significant buffering capacity (Carney et al., 1989; Yamada et al., 1998); in some circumstances washing with specific buffered antioxidant formulations such as described here or possibly inducing tearing might be preferable to washing with tap water. These results suggest that new washing procedures that account for tear chemistry might result in improved outcomes compared with water irrigation. Specifically, these results indicate that after 32% chlorine bleach eye exposure, washing with water results in a DoD of 59.6±3.6%, which is >20% cell depth of death, a level of damage predicted to cause extreme/permanent eye injury or even blindness in vivo (extreme or irreversible injury, GHS category 1, see Lebrun et al., 2019) but washing with EWB+0.2% AA after bleach exposure reduces this damage to a DoD of 13.8±1.4, which is a depth of damage below 20%, a minor amount of damage (GHS category 2, eye irritation) which is predicted to completely heal within 21 days in vivo (Lebrun et al., 2019).

A notable observation is that after NaOCl eye exposure, TUNEL-positive and -negative regions (i.e., "dead and live zones") are separated by an apparent "line of demarcation," separating dead regions from live regions, shown in FIGS. 13-16. As NaOCl toxicity increases, the "line of demarcation" moves deeper into the stroma, and there is an increased depth of damage. As mentioned above, a depth greater than 20% marks the transition of damage that correlates with eye irritation (reversible injury; not GHS category 1) to permanent eye injury (extreme or irreversible injury, GHS category 1, see Lebrun et al., 2019). Washing with buffered 0.2% AA results in shifting of the depth of TUNEL-positive layer and "line of demarcation" toward the superficial cornea. In these studies, whole eyes were washed, and the AA diffusion gradient is from the outside in (superficial/epithelial side towards the deep corneal stroma/endothelial side). These results indicate that buffered AA protects the eye opposite of the diffusion gradient: buffered AA protection does not reflect its diffusion pathway from the epithelium into the stroma. One model to explain this assumes that NaOCl progressively/slowly corrodes the tissue more deeply with time and wash buffer can quickly penetrate "porous" tissue that has been corroded. pH/ROS neutralization would occur at whatever level was reached prior to the wash because the chemical toxin has corroded the tissue allowing for rapid diffusion/entry of the wash buffer. Therefore and theoretically, AA is effective at reducing damage because it inactivates the toxin (and stops further killing) at the current washing depth of corrosion. Nonetheless, the model assumes that washing and toxin inactivation cannot save the cells that have already been damaged ("killed"). Although it requires further evaluation, this model of damage and washing would account for the shift in line of demarcation opposite to the wash diffusion gradient. It's notable just how even and consistent the "line of demarcation" is, even when the number of dead cells is reduced with EWB+AA washing (see FIGS. 14-16).

Previous studies on the therapeutic effects of AA after chemical injury have evaluated 10% AA eye drops (alone and in combination with other drugs), which are applied as drops (typically 2 drops/eye=80 µL) 2 h after injury and regularly thereafter (Tripathi et al., 2020; Fuchs et al., 2022; Mohan et al., 2022). In contrast to those studies, our invention uses high-volume (100-500 mL) washing with a lower concentration (0.2%) of freshly formulated buffered AA wash solution, which may clear residual toxin from the cornea ("wash out") and surrounding areas and provide a more continuous and steady corneal exposure than eye drops and while EWB+0.2% AA significantly reduced toxicity compared with EWB alone, washing with a EWB+10% AA resulted in a very high level of cytotoxicity. Note that a 10% AA solution is a very high concentration (100 g/L), which is an unreasonably large amount for an eyewash product where 500 mL is used as a wash (but not an issue for eyedrops where only 80 µL is used; 10% of 80 µL is only 8 mg), making the potential price of a 10% wash untenable, production difficult (due to solubility, 10% AA takes a very long time to mix and pH adjust) and shelf life poor because 10% AA does not stay in solution, forms a precipitate, oxidizes and becomes inactive. Most importantly, our results indicate that when 10% AA is used as a wash, there is massive corneal keratocyte toxicity. Further studies are required to better understand why washing with 10% AA was so toxic to the cornea. As mentioned above, 10% eye drop solutions have been used 2 h after exposure by other groups; differences in volume and treatment method may impact efficacy and toxicity.

We also note that within hours of room temperature storage, a 10% AA solution oxidizes to form a yellow solution and within days turns deep orange with a precipitate. While the 0.2% AA solution did not change color as rapidly, after several days at room temperature, it also oxidized and turned yellow then orange. An advantage of a 0.2% AA solution is that AA oxidation can be reduced by making the wash solution from powder just prior to washing (versus a 10% AA solution, which takes hours to dissolve, and then pH adjusted to 6.99) (Lebrun and Nguyen, 2024).

As discussed above, our preliminary studies on tears and AA were focused on oxidation and ROS, and this study focuses on NaOCl, which is a strong oxidant but also an alkali (pH 12), similar in pH to the NaOH used for the AA studies by other groups described in the introduction. The reason EWB reduces cell killing compared with water is from a pH buffering effect, and the reason EWB+0.2% AA reduces cell killing compared with EWB alone is due to an antioxidant effect.

Summary: Buffered 0.2% AA significantly reduces keratocyte death as compared with the standard practice of washing with water. Our hypothesis is that washing with a buffer neutralizes pH imbalances that may increase cell death and adding AA reduces damaging ROS levels and potentially slows or stops redox ROS cycling, which is associated with extensive and continued tissue damage. Since an estimated greater than 80% of chemicals that cause extreme/irreversible damage to the eye are associated with ROS and/or extreme pH, this invention will reduce damage cause by the majority of ocular toxins including those shown in supplemental table 1.

A most differentiating and unexpected aspect of the invention is the disclosed effectiveness at reducing corneal keratocyte cell death after chemical injury. Results indicate that after toxic chemical eye exposure, washing with water resulted in a depth of keratocyte damage of 59.6±3.6%, which is >20% cell depth of death, a level of damage that results in extreme/permanent eye injury or even blindness in vivo but washing with the 0.2% buffered AA formulation after the same toxin exposure reduced the depth of damage to 13.8±1.4, which is a depth of damage below 20%, a minor amount of damage (eye irritation) which will completely heal in vivo within 21 days. The significant and unexpected effectiveness is attributed to the formulation and procedures of use that results in the specific and significant reduction in corneal keratocyte cell death, which differentiates it from the prior art.

The prior art uses a Pharmaceutical approach versus the washing strategy of this invention. The main differences between pharmaceutical and washing strategies are dose (volume), concentration and timing and duration of administration. The prior art uses 1 or 2 drops (40-80 µL) of 10% AA starting around 2 hours after or longer after exposure of the eye to a toxin. Versus, this invention, which uses 100-500 ml of 0.2% AA within 10 minutes after chemical eye exposure and administered continuously over the course of 1-30 minutes.

The 10% AA used by the prior art is too high of a concentration for a continuous 1-30 wash procedure because we identified that when 10% AA is used as a continuous wash it kills corneal keratocytes. The prior art does not measure or concern itself with corneal keratocyte survival rates. It is likely that the methods described by the prior art are killing keratocytes with 10% AA but since the mechanisms and procedures are different than this invention, keratocyte killing is likely a "side effect" for the prior art methods. Another explanation might be that the transient "pharmaceutical" use of 1-2 drops of 10% AA used in the prior art might be tolerated because it is a "short burst" exposure but, as discussed above is cytotoxic when used for the high volume continuous wash of this invention. In either case, the concentration of AA is a major differentiating feature between this invention and the prior art. We teach away from 10% AA because it is cytotoxic as a high volume wash and also will not make a good wash product because 10% AA is very slow to go into and difficult to stay in solution ("saturated": 10% is about the maximum water solubility of AA) and 10% (100 g/L) of AA is too expensive and wasteful for a high volume wash product.

Summary of why this Invention is Unexpected and Different than the Prior Art When used as described in the claims, washing the eye after chemical injury with buffered 0.2% AA has a remarkable ability to protect the cells of the cornea from chemically induced cytotoxicity. This is an unexpected and novel finding. There are 5 reasons the disclosed invention is unexpected and differs from the prior art:

1. Poor efficacy and different tissue effects not linked to keratocytes (prior art) vs unexpectedly good efficacy with a specific increase in corneal keratocyte survival rate and reduction in the depth of corneal keratocyte damage (this invention)
2. Treatment volume 80 µL (prior art) vs. 100-500 ml (this invention)
3. Ascorbic acid concentration 10% (prior art) vs. 0.2% (this invention)
4. Treatment initiation, 2 hours (prior art) vs. within 10 minutes (this invention).

5. Duration of treatment, transient drops (prior art) vs. continuous wash over the course of 1-30 minutes (this invention)

REFERENCES

Banin E., Morad Y., Berenshtein E., Obolensky A., Yahalom C., Goldich J., Adibelli F M., Zuniga G., DeAnda M., Pe'er J., Chevion M. (2003). "Injury induced by chemical warfare agents: characterization and treatment of ocular tissues exposed to nitrogen mustard". Invest Ophthalmol Vis Sci. 44(7): 2966-72. doi: 10.1167/iovs.02-1164. PMID: 12824239.

Barroso J., Pfannenbecker U., Adriaens E., Alépée N., Cluzel M., De Smedt A., Hibatallah J., Klaric M., Mewes K R., Millet M., Templier M., McNamee P. (2017). "Cosmetics Europe compilation of historical serious eye damage/eye irritation in vivo data analysed by drivers of classification to support the selection of chemicals for development and evaluation of alternative methods/strategies: the Draize eye test Reference Database (DRD)". Arch Toxicol. 91(2): 521-547. doi: 10.1007/s00204-016-1679-x. Epub 2016 Mar. 21. PMID: 26997338; PMCID: PMC5306081

Bunker D J., George R J., Kleinschmidt A., Kumar R J., Maitz P. (2014). "Alkali-related ocular burns: a case series and review". J Burn Care Res. May-June; 35(3): 261-8. doi: 10.1097/BCR.0b013e31829b0037. PMID: 2387713

Capella J. A., Kaufman H. E., Robbins J. E. (1965). "Preservation of viable corneal tissue". Cryobiology. 2(3): 116-21. doi: 10.1016/s0011-2240(65) 80096-7. PMID: 4159430.

Carney L G., Mauger T F., Hill R M. (1989). "Buffering in human tears: pH responses to acid and base challenge". Invest Ophthalmol Vis Sci. 1989 April; 30(4): 747-54. PMID: 2703317.

Chau J P., Lee D T., Lo S H. (2012). "A systematic review of methods of eye irrigation for adults and children with ocular chemical burns". Worldviews Evid Based Nurs. 9(3): 129-38. doi: 10.1111/j. 1741-6787.2011.00220.x. Epub 2011 Jun. 7. PMID: 21649853.

Chen Y., Mehta G., Vasiliou V. (2009). "Antioxidant defenses in the ocular surface". Ocul Surf. 7(4): 176-85. doi: 10.1016/s1542-0124(12) 70185-4. PMID: 19948101; PMCID: PMC4104792.

Clare G., Bunce C., Tuft S. (2022). "Amniotic membrane transplantation for acute ocular burns". Cochrane Database Syst Rev. 9(9): CD009379. doi: 10.1002/14651858.CD009379.pub3. PMID: 36047788; PMCID: PMC9435439.

Corrales J., Kristofco L A., Steele W B., Saari G N., Kostal J., Williams E S., Mills M., Gallagher E P., Kavanagh T J., Simcox N., Shen L Q., Melnikov F., Zimmerman J B., Voutchkova-Kostal A M., Anastas P T., Brooks B W. (2017). "Toward the Design of Less Hazardous Chemicals: Exploring Comparative Oxidative Stress in Two Common Animal Models". Chem Res Toxicol. 30(4): 893-904. doi: 10.1021/acs.chemrestox.6b00246. Epub 2016 Nov. 3. PMID: 27750016.

Dua H S., Ting D S J., Al Saadi A., Said D G. (2020). "Chemical eye injury: pathophysiology, assessment and management". Eye (Lond). 34(11): 2001-2019. doi: 10.1038/s41433-020-1026-6. Epub 2020 Jun. 22. PMID: 32572184; PMCID: PMC7784957.

ECETOC. (1998). "Technical Report No. 48(2), Eye Irritation: Reference Chemicals Data Bank (Second Edition)". European Centre for Ecotoxicology and Toxicology of Chemicals.

Fuchs A A., Balne P K., Giuliano E A., Sinha N R., Mohan R R. (2022). "Evaluation of a novel combination of TRAM-34 and ascorbic acid for the treatment of corneal fibrosis in vivo". PLOS One. 17(1): e0262046. doi: 10.1371/journal.pone.0262046. PMID: 35007294; PMCID: PMC8746773.

Gupta N., Kalaivani M., Tandon R. (2011). "Comparison of prognostic value of Roper Hall and Dua classification systems in acute ocular burns". Br J Ophthalmol. 95(2): 194-8. doi: 10.1136/bjo.2009.173724. Epub 2010 Aug. 30. PMID: 20805137.

Hall A H., Maibach H I. (2006). "Water decontamination of chemical skin/eye splashes: a critical review". Cutan Ocul Toxicol. 25(2): 67-83. doi: 10.1080/15569520600695520. PMID: 16835144

Herr R D., White G L Jr., Bernhisel K., Mamalis N., Swanson E. (1991). "Clinical comparison of ocular irrigation fluids following chemical injury". Am J Emerg Med. 9(3): 228-31. doi: 10.1016/0735-6757(91) 90082-u. PMID: 1850282.

Kuckelkorn R., Schrage N., Keller G., Redbrake C. (2002). "Emergency treatment of chemical and thermal eye burns". Acta Ophthalmol Scand. 80(1): 4-10. doi: 10.1034/j.1600-0420.2002.800102.x. PMID: 11906296.

Lebrun S., Xie Y., Chavez S., Chan R., Jester J V. (2019). "An in vitro depth of injury prediction model for a histopathologic classification of EPA and GHS eye irritants". Toxicol In Vitro. 61:104628. doi: 10.1016/j.tiv.2019.104628. Epub 2019 Aug. 13. PMID: 31419508; PMCID: PMC6922541.

Lebrun S J., Chavez S., Chan R., Nguyen L., Jester J V. (2021a). "Modeling the antioxidant properties of the eye reduces the false-positive rate of a nonanimal eye irritation test (OptiSafe)". Toxicol In Vitro. 76:105208. doi: 10.1016/j.tiv.2021.105208. Epub 2021 Jun. 30. PMID: 34216722; PMCID: PMC8522283.

Lebrun S., Nguyen L., Chavez S., Chan R., Le D., Nguyen M., Jester J V. (2021b). "Same-chemical comparison of nonanimal eye irritation test methods: Bovine corneal opacity and permeability, EpiOcular™, isolated chicken eye, ocular Irritection®, OptiSafe™, and short time exposure". Toxicol In Vitro.72:105070. doi: 10.1016/j.tiv.2020.105070. Epub 2020 Dec. 19. PMID: 33352259; PMCID: PMC8544240.

Lebrun S., Chan R., Chavez S., inventors. (2021c). "Formulations and Methods Related to Eye Irritation". patent application Ser. No. 17/203,467. In review. US Patent and Trademark Office.

Lebrun S., Chan R., Chavez S., inventors. (2021d). "Formulations and Methods Related to Eye Irritation and Related". patent application Ser. No. 18/348,193. In review. US Patent and Trademark Office.

Lebrun S., Chan R., Chavez S., inventors. (2021e). "Related Formulations and Methods Related to Eye Irritation". patent application Ser. No. 18/348,237. In review. US Patent and Trademark Office.

Lebrun S., Chavez S., Chan R., Nguyen L., Jester J V. (2022). "Ascorbic acid specifically reduces the misclassification of nonirritating reactive chemicals in the OptiSafe™ macromolecular eye irritation test". Toxicol In Vitro. 80:105313. doi: 10.1016/ j.tiv.2022.105313. Epub 2022 Jan. 13. PMID: 35033652; PMCID: PMC9590652.

Lebrun S., Nguyen L., inventors. (2022). "Method and Reagents to Improve Nonanimal Ocular Toxicity Tests." patent application Ser. No. 17/889,026. In review. US Patent and Trademark Office Lebrun S., Chavez S., Nguyen L., Chan R. (2023a). "Expansion of the application domain of a macromolecular ocular irritation test (OptiSafe™)". Toxicol In Vitro. 86:105515. doi: 10.1016/j.tiv.2022.105515. Epub 2022 Nov. 6. PMID: 36351539; PMCID: PMC9802687.

Lebrun S., Chavez S., Nguyen L., Chan R. (2023b). "Further optimisation of a macromolecular ocular irritation test (OptiSafe™)". Cutan Ocul Toxicol. 42(1): 38-48. doi: 10.1080/15569527.2023.2170067. Epub 2023 Jan. 28. PMID: 36669195; PMCID: PMC10381028.

Lebrun S., Nguyen L., inventors. (2024). "Emergency Eye Wash". Patent Application No. 63/553,989. Submitted. US Patent and Trademark Office.

Lee M Y., Chung S K. (2012). "Treatment of corneal neovascularization by topical application of ascorbic acid in the rabbit model". Cornea. 31(10): 1165-9. doi: 10.1097/ICO.0b013e318241433b. PMID: 22832865.

Levinson R A., Paterson C A., Pfister R R. (1976). "Ascorbic acid prevents corneal ulceration and perforation following experimental alkali burns". Invest Ophthalmol. 1976 December; 15(12): 986-93. PMID: 992963.

Mapara M., Thomas B S., Bhat K M. (2012). "Rabbit as an animal model for experimental research". Dent Res J (Isfahan). 9(1): 111-8. doi: 10.4103/1735-3327.92960. PMID: 22363373; PMCID: PMC3283968.

Mohan R R., Kempuraj D., D'Souza S., Ghosh A. (2022). "Corneal stromal repair and regeneration". Prog Retin Eye Res. 91:101090. doi: 10.1016/j.preteyeres.2022.101090. Epub 2022 May 29. PMID: 35649962.

NIH. (2024). "PubMed®". National Library of Medicine. National Center for Biotechnology Information. Available at: https://pubmed.ncbi.nlm.nih.gov OECD. (2024). "Better policies for better lives| OECD". Organisation for Economic Co-operation and Development. Available at: https://www.oecd.org/en.html OSHA. (2009). "1910.133—Eye and Face Protection". OSHA Regulations. Available at: https://www.osha.gov/laws-regs/regulations/standardnumber/1910/1910.133

Paterson C A., O'Rourke M C. (1987). "Vitamin C levels in human tears". Arch Ophthalmol. 105(3): 376-7. doi: 10.1001/archopht.1987.01060030096034. PMID: 3827714.

Pfister R R., Paterson C A. (1977). "Additional clinical and morphological observations on the favorable effect of ascorbate in experimental ocular alkali burns". Invest Ophthalmol Vis Sci. 16(6): 478-87. PMID: 863611.

Pfister R R., Paterson C A., Hayes S A. (1978). "Topical ascorbate decreases the incidence of corneal ulceration after experimental alkali burns". Invest Ophthalmol Vis Sci. 17(10): 1019-24. PMID: 700951.

Pfister R R., Paterson C A., Spiers J W., Hayes S A. (1980). "The efficacy of ascorbate treatment after severe experimental alkali burns depends upon the route of administration". Invest Ophthalmol Vis Sci. 19(12): 1526-9. PMID: 7440108.

Pennsylvania State University (PSU). (1994). "Agricultural Alternatives: Rabbit Production". Available at: https://animalscience.psu.edu/files/pdf/ua274.pdf Qin G., Zhang P., Sun M., Fu W., Cai C. (2022). "Comprehensive spectral libraries for various rabbit eye tissue proteomes". Sci Data. 9(1): 111. doi: 10.1038/s41597-022-01241-5. PMID: 35351915; PMCID: PMC8964796.

Reiss G R., Werness P G., Zollman P E., Brubaker R F. (1986). "Ascorbic acid levels in the aqueous humor of nocturnal and diurnal mammals". Arch Ophthalmol. 104(5): 753-5. doi: 10.1001/archopht.1986.01050170143039. PMID: 3707416.

Rihawi S., Frentz M., Becker J., Reim M., Schrage N F. (2007). "The consequences of delayed intervention when treating chemical eye burns". Graefes Arch Clin Exp Ophthalmol. 245(10): 1507-13. doi: 10.1007/s00417-007-0597-2. Epub 2007 May 10. PMID: 17492301.

Schneider C A., Rasband W S., Eliceiri K W. (2012). "NIH Image to ImageJ: 25 years of image analysis". Nat Methods. 9(7): 671-5. doi: 10.1038/nmeth.2089. PMID: 22930834; PMCID: PMC5554542.

Siddiqui S A., Gerini F., Ikram A., Saeed F., Feng X., Chan Y. (2023). "Rabbit Meat-Production, Consumption and Consumers' Attitudes and Behavior. Sustainability. doi: 10.3390/su15032008

Stadelmann C., Lassmann H. (2000). "Detection of apoptosis in tissue sections". Cell Tissue Res. 301(1): 19-31. doi: 10.1007/s004410000203. PMID: 10928278.

Szendrö K., Szabó-Szentgróti E., Szigeti O. (2020). "Consumers' Attitude to Consumption of Rabbit Meat in Eight Countries Depending on the Production Method and Its Purchase Form". Foods. 9(5): 654. doi: 10.3390/foods9050654. PMID: 32438696; PMCID: PMC7278728.

Tripathi R., Balne P K., Sinha N R., Martin L M., Kamil S., Landreneau J R., Gupta S., Rodier J T., Sinha P R., Hesemann N P., Hofmann A C., Fink M K., Chaurasia S S., Mohan R R. (2020). "A Novel Topical Ophthalmic Formulation to Mitigate Acute Mustard Gas Keratopathy In Vivo: A Pilot Study". Transl Vis Sci Technol. 9(12): 6. doi: 10.1167/tvst.9.12.6. PMID: 33200047; PMCID: PMC7645241.

Trocino A., Cotozzolo E., Zomeño C., Petracci M., Xiccato G., Castellini C. (2019). "Rabbit production and science: the world and Italian scenarios from 1998 to 2018". Italian Journal of Animal Science. 18(1): 1361-1371. doi: 10.1080/1828051X.2019.1662739

Ung L., Pattamatta U., Carnt N., Wilkinson-Berka J L., Liew G., White A J R. (2017). "Oxidative stress and reactive oxygen species: a review of their role in ocular disease". Clin Sci (Lond). 131(24): 2865-2883. doi: 10.1042/CS20171246. PMID: 29203723.

USDA. (2024). "Rabbit From Farm to Table". Available at: https://www.fsis.usda.gov/food-safety/safe-food-handling-and-preparation/meat-fish/rabbit-farm-table Yamada M., Kawai M., Mochizuki H., Hata Y., Mashima Y. (1998). "Fluorophotometric measurement of the buffering action of human tears in vivo". Curr Eye Res. 17(10): 1005-9. doi: 10.1076/ceyr.17.10.1005.5239. PMID: 9788303.

York M., Steiling W. (1998). "A critical review of the assessment of eye irritation potential using the Draize rabbit eye test". J Appl Toxicol. 18(4): 233-40. doi:

US 12,648,892 B2

55
56

10.1002/(sici) 1099-1263(199807/08) 18: 4<233::aid-jat496>3.0.co; 2-y. PMID: 9719422.

Zernii E Y., Baksheeva V E., Iomdina E N., Averina O A., Permyakov S E., Philippov P P., Zamyatnin A A., Senin I I. (2016). "Rabbit Models of Ocular Diseases: New Relevance for Classical Approaches". CNS Neurol Disord Drug Targets. 5(3): 267-91. doi: 10.2174/1871527315666151110124957. PMID: 26553163.

What is claimed is:

1. A shelf-stable device or product for reducing extent and depth of keratocyte injury in a stroma of a cornea of a mammal, which cornea has been exposed to a strong oxidizing and/or corrosive chemical, the device or product producing a buffered eye wash solution of 0.2% ascorbic acid buffered to a pH of 6.99±0.5 and in an amount of 100 mL to 500 mL, comprising a two-part formulation having (a) a 100 mL to 500 mL liquid portion in at least a first compartment, and (b) a solid portion, wherein the first compartment holds a the liquid portion comprising a predefined amount of water or aqueous solution, and wherein the solid portion consists of an amount of powder within a premeasured range which results in solution of 0.2% ascorbic acid when added to the 100 mL to 500 mL liquid portion; and wherein separate storage in the device or product of the solid portion consisting of an amount of powder and of the liquid portion comprising a predefined amount of water or aqueous solution in the first compartment results, when the solid portion and liquid portion are combined and used as an eyewash solution within 10 minutes or less from exposure, in an increase in keratocyte survival and reduction in depth of corneal injury over stabilized ascorbate storage or over 10% ascorbic acid solution, and wherein the liquid portion of the first compartment mixed with the solid portion makes the 100 mL to 500 mL of a eyewash of 0.2% ascorbic acid solution, also contains a pH buffer, effecting a pH of 6.99±0.5 in the eyewash;

and a nozzle, valve, spray, squeeze or handheld inversion nozzle for delivery to an eye or both eyes of a user subject the eyewash 0.2% ascorbic acid solution, wherein the nozzle, valve, spray, squeeze or handheld inversion nozzle allows application of a laminar flow across the eye or both eyes of the user subject when the eye or eyes are positioned within a predetermined range of distance from the nozzle, valve, spray, squeeze or handheld inversion nozzle, so as to wash the eye or eyes or wherein the device comprises an inverted eye gasket that permits incubation and/or bathing the eye or eyes of the user subject in a flow or a pool of the 100 mL to 500 mL eyewash 0.2% ascorbic acid solution by holding the device or product over the eye or eyes to form a seal around an eye socket with the eye gasket and raising the first compartment up so that the eyewash 0.2% ascorbic acid solution contacts the cornea of the eye or eyes, so as to wash the eye or eyes.

2. The device or product of claim 1, wherein the liquid portion can be mixed with the solid portion added thereto by shaking or inverting the device or product or portion thereof.

3. A device or product for reducing extent and depth of keratocyte injury in a stroma of a cornea of a mammal, which cornea has been exposed to a strong oxidizing and/or corrosive chemical, the drive or product producing a buffered eye wash solution of 0.1% to 0.3% ascorbic acid buffered to a pH of 6.0 to 6.99±0.5 and in an amount of 100 mL to 1000 mL comprising a two-part formulation having at least a first compartment and a solid portion consisting of an amount of powder, wherein the first compartment holds a liquid portion comprising a predefined amount of water or aqueous solution, and wherein the solid portion consists of an amount of powder within a premeasured range, and wherein the liquid portion mixes, or is capable of being mixed, with the solid portion so as to make the 100 mL to 1000 mL of a eyewash solution of 0.1% to 0.3% ascorbic acid, and wherein the eyewash solution also contains a pH buffer, effecting a pH of 6.0 to 6.99±0.5 in the eyewash solution of 0.1% to 0.3% ascorbic acid, and when used as an eyewash solution within 10 minutes or less from exposure, in an increase in keratocyte survival and reduction in depth of corneal injury over stabilized ascorbate storage or over 10% ascorbic acid solution, and a nozzle, valve, spray, squeeze or handheld inversion nozzle for delivery to an eye or both eyes of a user subject the eyewash 0.1% to 0.3% ascorbic acid solution;

wherein the nozzle, valve, spray, squeeze or handheld inversion nozzle allows application of a laminar flow across the eye or both eyes of the user subject when the eye or eyes are positioned within a predetermined range of distance from the nozzle, valve, spray, squeeze or handheld inversion nozzle and so as to wash the eye or eyes or wherein the device comprises an inverted eye gasket that permits incubation and/or bathing the eye or eyes of the user subject in a flow or a pool of the eyewash solution of 0.1% to 0.3% ascorbic acid by holding the device or product over the eye or eyes to form a seal around an eye socket with the eye gasket and raising the first compartment up so that the eyewash solution of 0.1% to 0.3% ascorbic acid contacts the cornea of the eye or eyes.

4. The device or product of claim 3, in which the solid portion is 5.7 mM- 17mg/ml ascorbic acid.

5. The device or product of claim 3, in which the solid portion is about 11.4 mM ascorbic acid.

6. The device or product of claim 3, in which a buffering capacity of the liquid portion, is such that the eyewash pH achieved is between 6 and 6.99.

7. A method comprising, within 10 minutes or less from exposure, administering to the cornea for a period of 1 minute to 15 minutes a buffered eyewash solution of 0.2% ascorbic acid buffered to a pH of 6.99+0.5 and in an amount of 100 mL to 500 mL as a flow or as a pool in contact with said cornea, using the shelf-stable device or product of claim 1.

8. A method comprising, within 10 minutes or less from exposure, administering to the cornea for a period of 1 minute to 15 minutes a buffered eye wash solution of 0.1% to 0.3% ascorbic acid buffered to a pH of 6.99+0.5 and in an amount of 100 mL to 1000 mL as a flow or as a pool in contact with said cornea, using the device or product of claim 3.

* * * * *